(12) United States Patent
Velazquez et al.

(10) Patent No.: US 7,485,625 B2
(45) Date of Patent: Feb. 3, 2009

(54) INHIBITORS OF HEPATITIS C VIRUS NS3/NS4A SERINE PROTEASE

(75) Inventors: Francisco Velazquez, Clinton, NJ (US); Srikanth Venkatraman, Woodbridge, NJ (US); Ashok Arasappan, Bridgewater, NJ (US); F. George Njoroge, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 391 days.

(21) Appl. No.: 11/007,910

(22) Filed: Dec. 9, 2004

(65) Prior Publication Data

US 2005/0153900 A1    Jul. 14, 2005

Related U.S. Application Data

(60) Provisional application No. 60/528,845, filed on Dec. 11, 2003.

(51) Int. Cl.
| | |
|---|---|
| A61K 38/00 | (2006.01) |
| A61J 38/06 | (2006.01) |
| C07K 5/00 | (2006.01) |
| C07K 7/00 | (2006.01) |
| C07K 16/00 | (2006.01) |
| C07K 17/00 | (2006.01) |
| C07D 401/00 | (2006.01) |

(52) U.S. Cl. .......................... 514/18; 530/331; 544/405
(58) Field of Classification Search ....................... None
See application file for complete search history.

(56) References Cited

U.S. PATENT DOCUMENTS 7,012,066 B2 * 3/2006 Saksena et al. ............... 514/18
2003/0216325 A1 * 11/2003 Saksena et al. ............... 514/18

FOREIGN PATENT DOCUMENTS

| WO | WO 01/74768 | 10/2001 |
| WO | WO 02/08244 | 1/2002 |
| WO | WO 02/18369 | 3/2002 |
| WO | WO 02/48172 | 6/2002 |
| WO | WO 03/062228 | 7/2003 |
| WO | WO 03/062265 | 7/2003 |

OTHER PUBLICATIONS

International Search Report for PCT/US2004/041579—4pgs.

* cited by examiner

*Primary Examiner*—Cecilia J Tsang
*Assistant Examiner*—Marcela M Cordero Garcia
(74) *Attorney, Agent, or Firm*—Palaiyur S. Kalyanaraman; Serena Farquharson-Torres

(57) ABSTRACT

The present invention discloses novel compounds which have HCV protease inhibitory activity as well as methods for preparing such compounds. In another embodiment, the invention discloses pharmaceutical compositions comprising such compounds as well as methods of using them to treat disorders associated with the HCV protease.

35 Claims, No Drawings

INHIBITORS OF HEPATITIS C VIRUS NS3/NS4A SERINE PROTEASE

FIELD OF THE INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention additionally discloses novel macrocyclic compounds as inhibitors of the HCV NS3/NS4a serine protease. This application claims priority from U.S. provisional patent application, Ser. No. 60/528845 filed Dec. 11, 2003.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH) (see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliary cirrhosis.

Recently, an HCV protease necessary for polypeptide processing and viral replication has been identified, cloned and expressed; (see, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy. The inventive compounds can inhibit such protease. They also can modulate the processing of hepatitis C virus (HCV) polypeptide.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) *Proc. Natl. Acad. Sci (USA)* 91:888-892, Failla et al. (1996) *Folding & Design* 1:35-42. The NS3/NS4a cleavage site is also more tolerant of mutagenesis than the other sites. See, e.g., Kollykhalov et al. (1994) *J. Virol.* 68:7525-7533. It has also been found that acidic residues in the region upstream of the cleavage site are required for efficient cleavage. See, e.g., Komoda et al. (1994) *J. Virol.* 68:7351-7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340-9348, Ingallinella et al. (1998) *Biochem.* 37:8906-8914, Llinàs-Brunet et al. (1998) *Bioorg. Med. Chem. Lett.* 8:1713-1718), inhibitors based on the 70-amino acid polypeptide eglin c (Martin et al. (1998) *Biochem.* 37:11459-11468, inhibitors affinity selected from human pancreatic secretory trypsin inhibitor (hPSTI-C3) and minibody repertoires (MBip) (Dimasi et al. (1997) *J. Virol.* 71:7461-7469), $cV_HE2$ (a "camelized" variable domain antibody fragment) (Martin et al. (1997) *Protein Eng.* 10:607-614), and α1-antichymotrypsin (ACT) (Elzouki et al.) (1997) *J. Hepat.* 27:42-28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30,1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

Reference is made to WO 00/59929 (U.S. Pat. No. 6,608, 027, Assignee: Boehringer Ingelheim (Canada) Ltd.; Published Oct. 12, 2000) which discloses peptide derivatives of the formula:

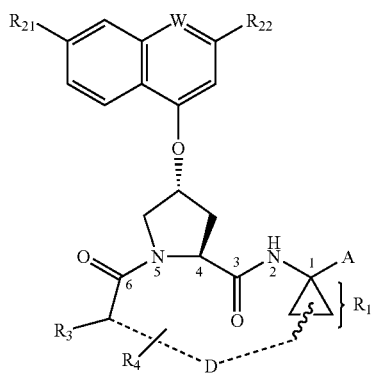

Reference is made to A. Marchetti et al, *Synlett*, S1, 1000-1002 (1999) describing the synthesis of bicylic analogs of an inhibitor of HCV NS3 protease. A compound disclosed therein has the formula:

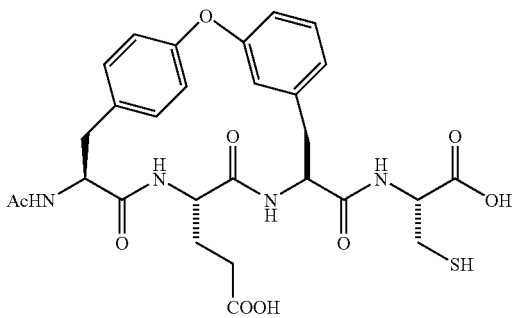

Reference is also made to W. Han et al, *Bioorganic & Medicinal Chem. Lett*, (2000) 10, 711-713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

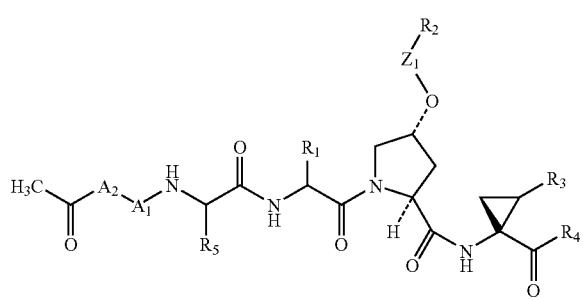

where the various elements are defined therein. An illustrative compound of that series is:

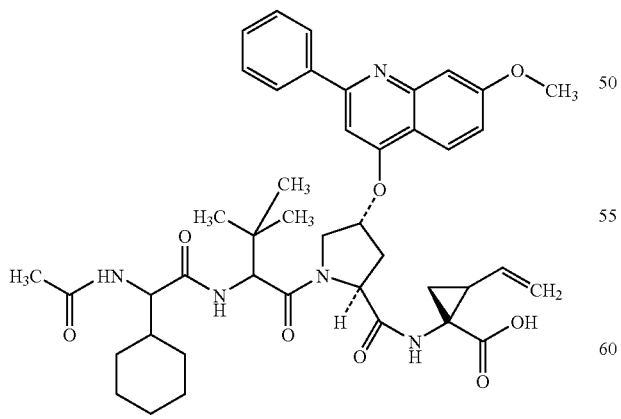

Reference is also made to WO 00/09543 (Assignee: Boehringer Ingelheim Limited; Published Feb. 24, 2000) which discloses peptide derivatives of the formula:

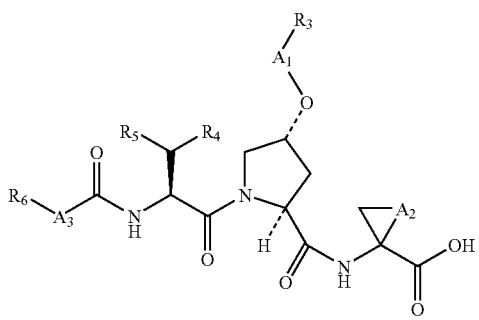

where the various elements are defined therein. An illustrative compound of that series is:

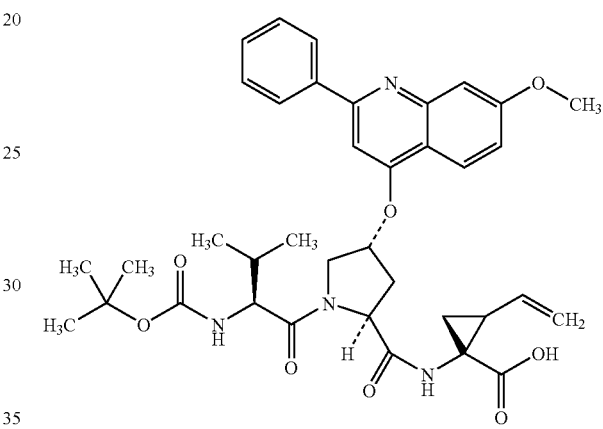

Reference is also made to U.S. Pat. No. 6,608,027 (Boehringer Ingelheim, Canada) which discloses NS3 protease inhibitors of the type:

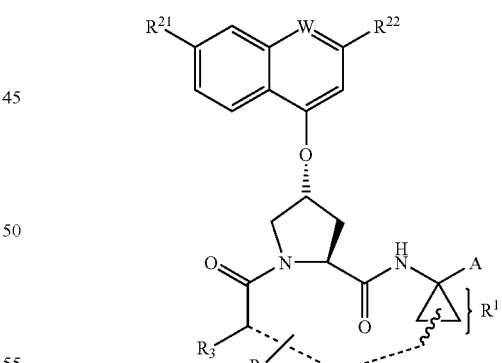

wherein the various moieties are defined therein.

Current therapies for hepatitis C include interferon-α (INF$_\alpha$) and combination therapy with ribavirin and interferon. See, e.g., Beremguer et al. (1998) *Proc. Assoc. Am. Physicians* 110(2):98-112. These therapies suffer from a low sustained response rate and frequent side effects. See, e.g., Hoofnagle et al. (1997) *N. Engl. J. Med.* 336:347. Currently, no vaccine is available for HCV infection.

Reference is further made to WO 01/74768 (Assignee: Vertex Pharmaceuticals Inc) published Oct. 11, 2001, which discloses certain compounds of the following general formula (R is defined therein) as NS3-serine protease inhibitors of Hepatitis C virus:

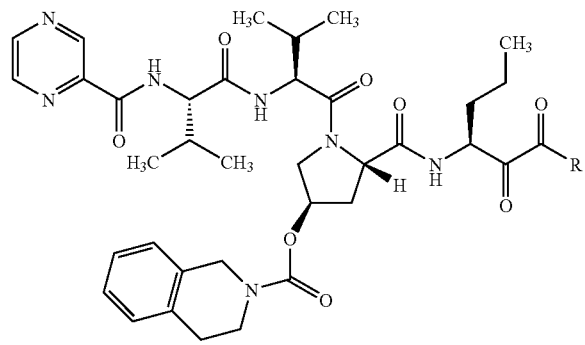

A specific compound disclosed in the afore-mentioned WO 01/74768 has the following formula:

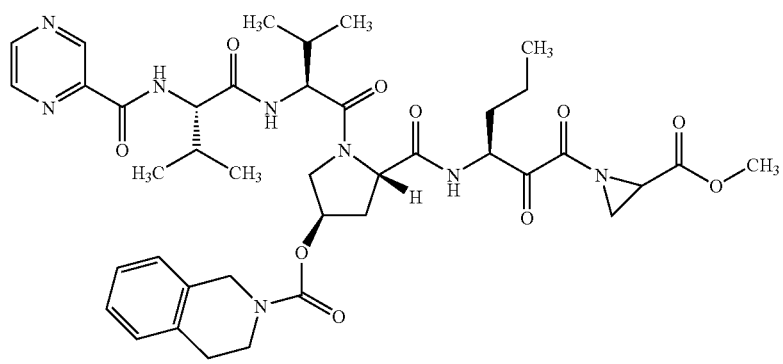

Reference is also made to WO02/18369 (Eli Lilly and Company) which discloses protease inhibitors. An illustrative compound disclosed therein has the structure:

Reference is also made to WO03/006490 (Vertex Pharmaceuticals) which discloses bridged bicyclic protease inhibitors. An illustrative compound disclosed therein has the structure:

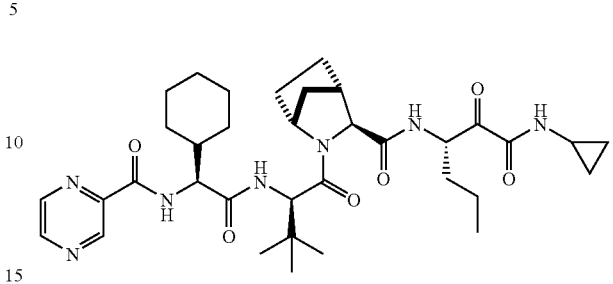

PCT Publications WO 01/77113; WO 01/081325; WO 02/08198; WO 02/08256; WO 02/08187; WO 02/08244; WO 02/48172; WO 02/08251; and pending U.S. patent application, Ser. No. 10/052,386, filed Jan. 18, 2002, disclose various types of peptides and/or other compounds as NS3/NS4a serine protease inhibitors of hepatitis C virus. Furthermore, pending U.S. applications Ser. No. 60/506,637 filed Sep. 26, 2003; 60/497,749 filed Aug. 26, 2003; and 60/523,715, filed

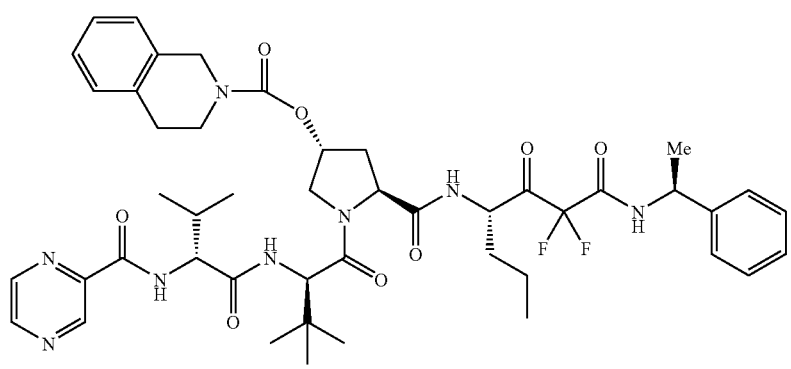

Nov. 20, 2003 disclose various types of protease inhibitors. The disclosures of those applications are incorporated herein by reference thereto.

There is a need for new treatments and therapies for HCV infection. There is a need for compounds useful in the treatment or prevention or amelioration of one or more symptoms of hepatitis C.

There is a need for methods of treatment or prevention or amelioration of one or more symptoms of hepatitis C.

There is a need for methods for modulating the activity of serine proteases, particularly the HCV NS3/NS4a serine protease, using the compounds provided herein.

There is a need for methods of modulating the processing of the HCV polypeptide using the compounds provided herein.

SUMMARY OF THE INVENTION

The afore-mentioned WO 02/08244 publication broadly discloses several compounds. Applicants found that a specific type of compounds surprisingly exhibits good HCV NS3/NS4a serine protease inhibitory activity. Thus, in its many embodiments, the present invention provides a novel class of inhibitors of the HCV protease, pharmaceutical compositions containing one or more of the compounds, methods of preparing pharmaceutical formulations comprising one or more such compounds, and methods of treatment or prevention of HCV or amelioration of one or more of the symptoms of hepatitis C using one or more such compounds or one or more such formulations. Also provided are methods of modulating the interaction of an HCV polypeptide with HCV protease. Among the compounds provided herein, compounds that inhibit HCV NS3/NS4a serine protease activity are preferred. The present invention thus discloses a compound, or enantiomers, stereoisomers, rotamers, tautomers, diastereomers, or racemates of said compound, or a pharmaceutically acceptable salt, solvate or ester of said compound, said compound having the general structure shown in Formula I:

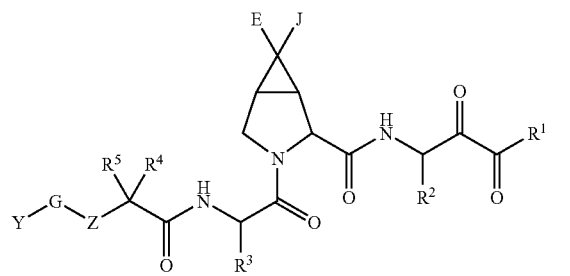

Formula I wherein:

$R^1$ is H, $OR^8$, $NR^9R^{10}$, or $CHR^9R^{10}$, wherein $R^8$, $R^9$ and $R^{10}$ can be the same or different, each being independently selected from the group consisting of H, alkyl-, aryl-, heteroalkyl-, heteroaryl-, cycloalkyl-, cycloalkyl-, arylalkyl-, and heteroarylalkyl;

E and J can be the same or different, each being independently selected from the group consisting of R, OR, NHR, $NRR^7$, SR, halo, and $S(O_2)R$, or E and J can be directly connected to each other to form either a three to eight-membered cycloalkyl, or a three to eight-membered heterocyclyl moiety;

Z is N(H), N(R), or O, with the proviso that when Z is O, G is present or absent and if G is present with Z being O, then G is C(=O);

G maybe present or absent, and if G is present, G is C(=O) or $S(O_2)$, and when G is absent, Z is directly connected to Y;

Y is selected from the group consisting of:

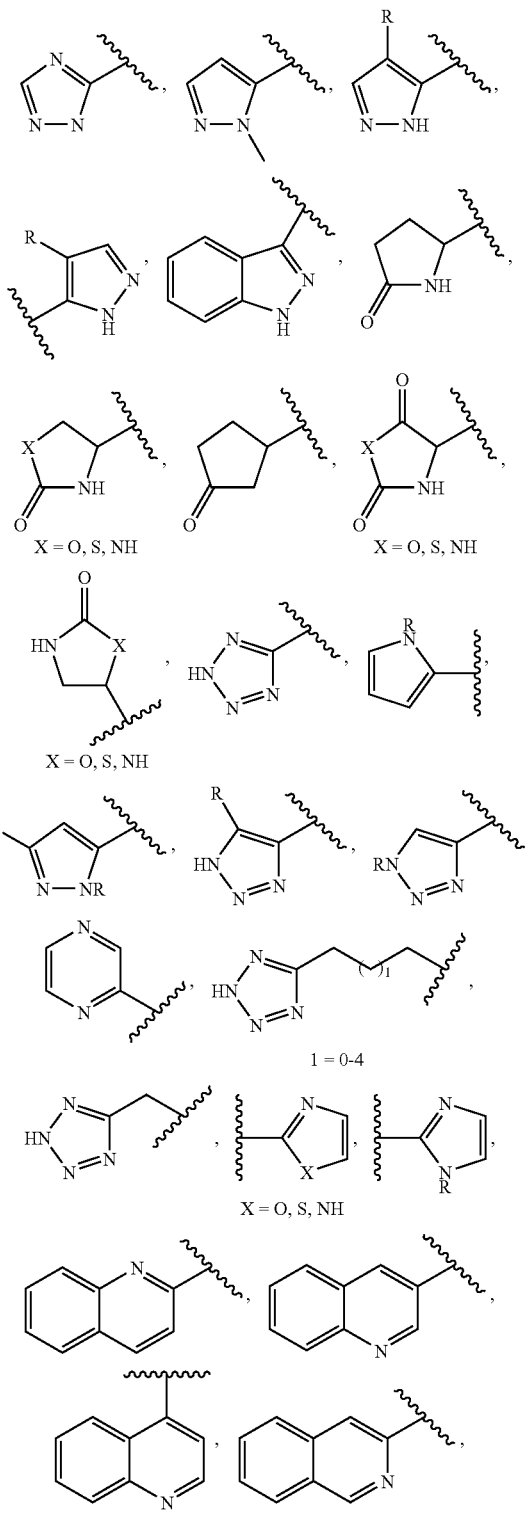

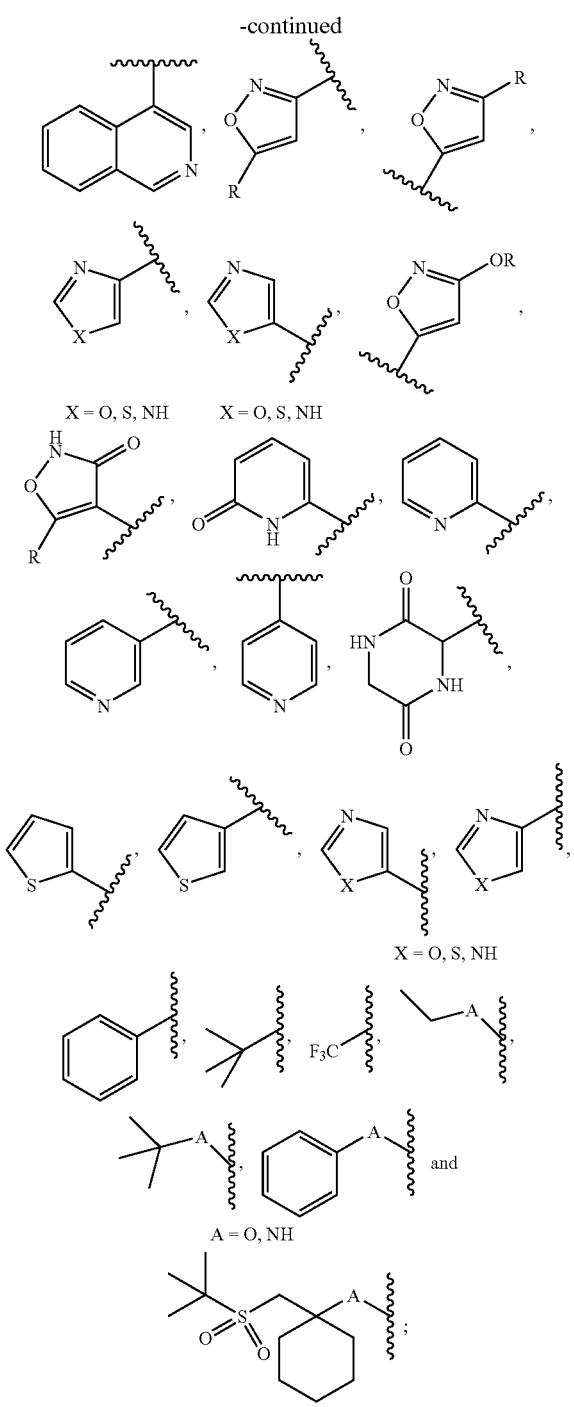

R, R[7], R[2], R[3], R[4] and R[5] can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-, wherein each of said heteroalkyl, heteroaryl and heterocyclyl independently has one to six oxygen, nitrogen, sulfur, or phosphorus atoms;
wherein each of said alkyl, heteroalkyl, alkenyl, alkynyl, aryl, heteroaryl, cycloalkyl and heterocyclyl moieties can be unsubstituted or optionally independently substituted with one or more moieties selected from the group consisting of alkyl, alkenyl, alkynyl, aryl, aralkyl, cycloalkyl, heterocyclyl, halo, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate.

The compounds represented by Formula 1, by themselves or in combination with one or more other additional suitable agents disclosed herein, can be useful for treating diseases such as, for example, HCV, HIV, (AIDS or Acquired Immune Deficiency Syndrome), and related disorders, as well as for modulating the activity of hepatitis C virus (HCV) protease, preventing HCV, or ameliorating one or more symptoms of hepatitis C. Such modulation, treatment, prevention or amelioration can be done with the inventive compounds as well as with pharmaceutical compositions or formulations comprising such compounds. Without being limited to theory, it is believed that the HCV protease may be the NS3 or NS4a protease. The inventive compounds can inhibit such protease. They can also modulate the processing of hepatitis C virus (HCV) polypeptide.

DETAILED DESCRIPTION

In an embodiment, the present invention discloses compounds which are represented by structural Formula 1 or a pharmaceutically acceptable salt, solvate or ester thereof, wherein the various moieties are as defined above.

In another embodiment, R[1] is NR[9]R[10], where R[9] is H, R[10] is H or R[14], wherein R[14] is alkyl, aryl, heteroalkyl, heteroaryl, cycloalkyl, alkyl-aryl-, alkyl-heteroaryl-, aryl-alkyl-, alkenyl, alkynyl or heteroaryl-alkyl-.

In another embodiment, R[14] is selected from the group consisting of:

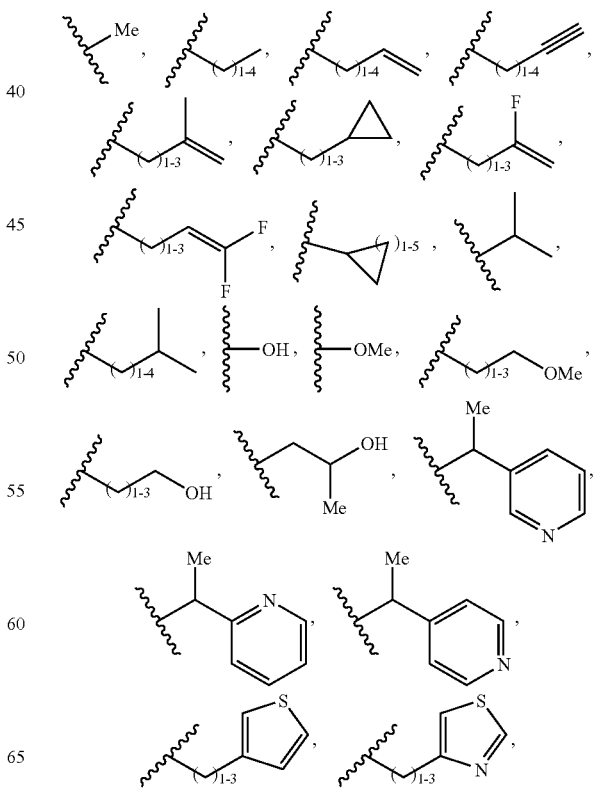

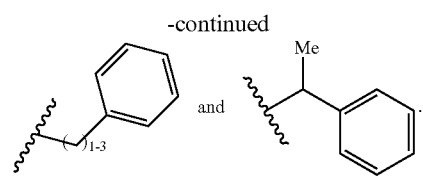
In another embodiment, $R^2$ is selected from the group consisting of the following moieties:
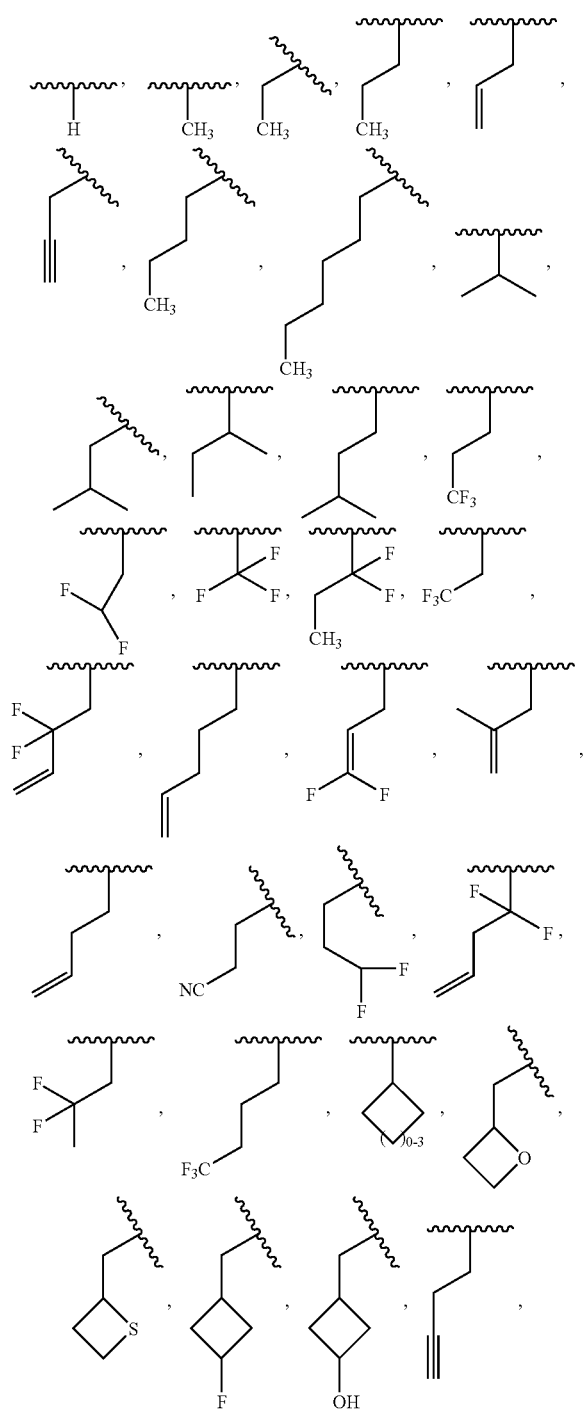
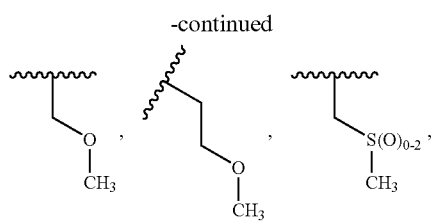
In another embodiment, $R^3$ is selected from the group consisting of:

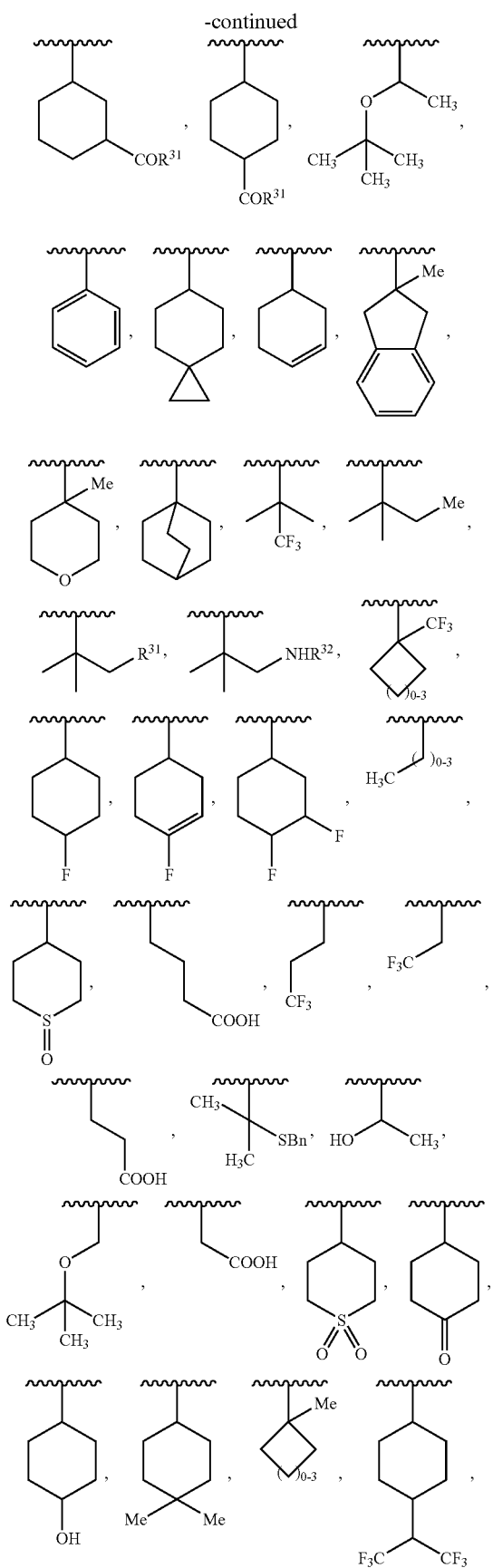
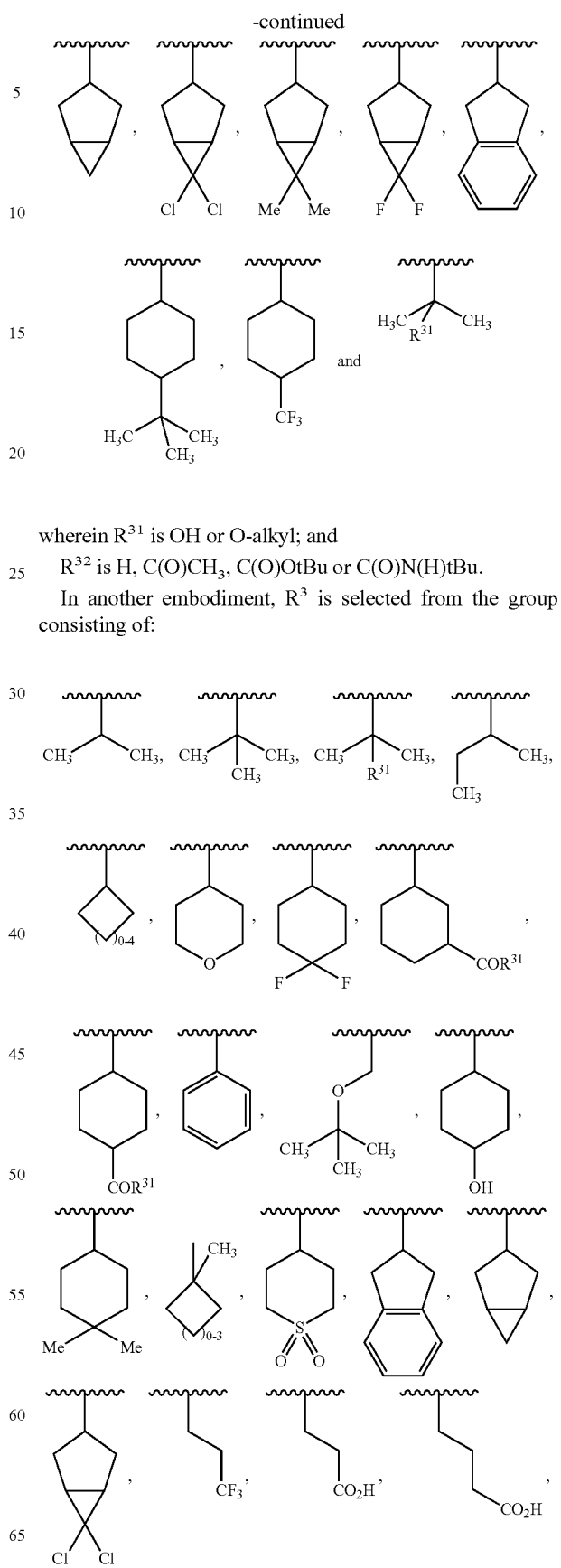
wherein $R^{31}$ is OH or O-alkyl; and
$R^{32}$ is H, C(O)CH$_3$, C(O)OtBu or C(O)N(H)tBu.
In another embodiment, $R^3$ is selected from the group consisting of:

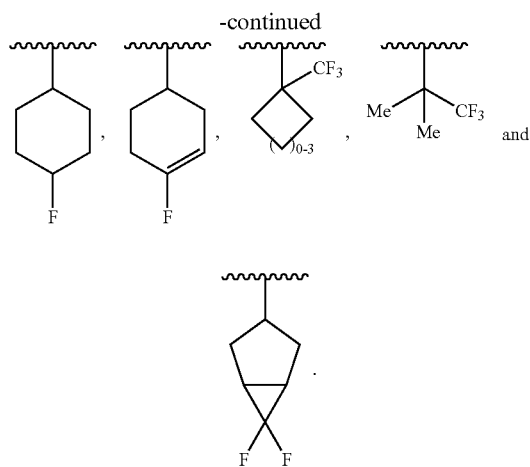
In another embodiment, the moiety
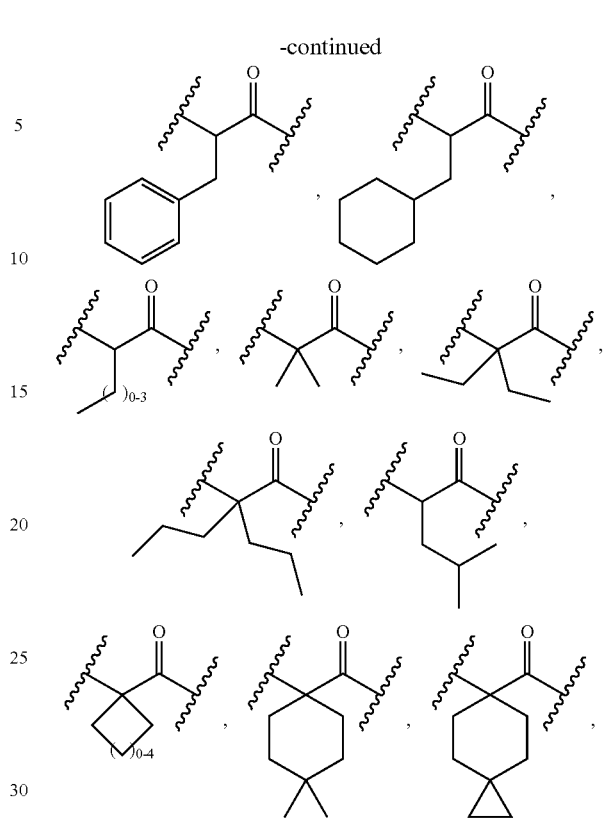
is selected from the group consisting of:
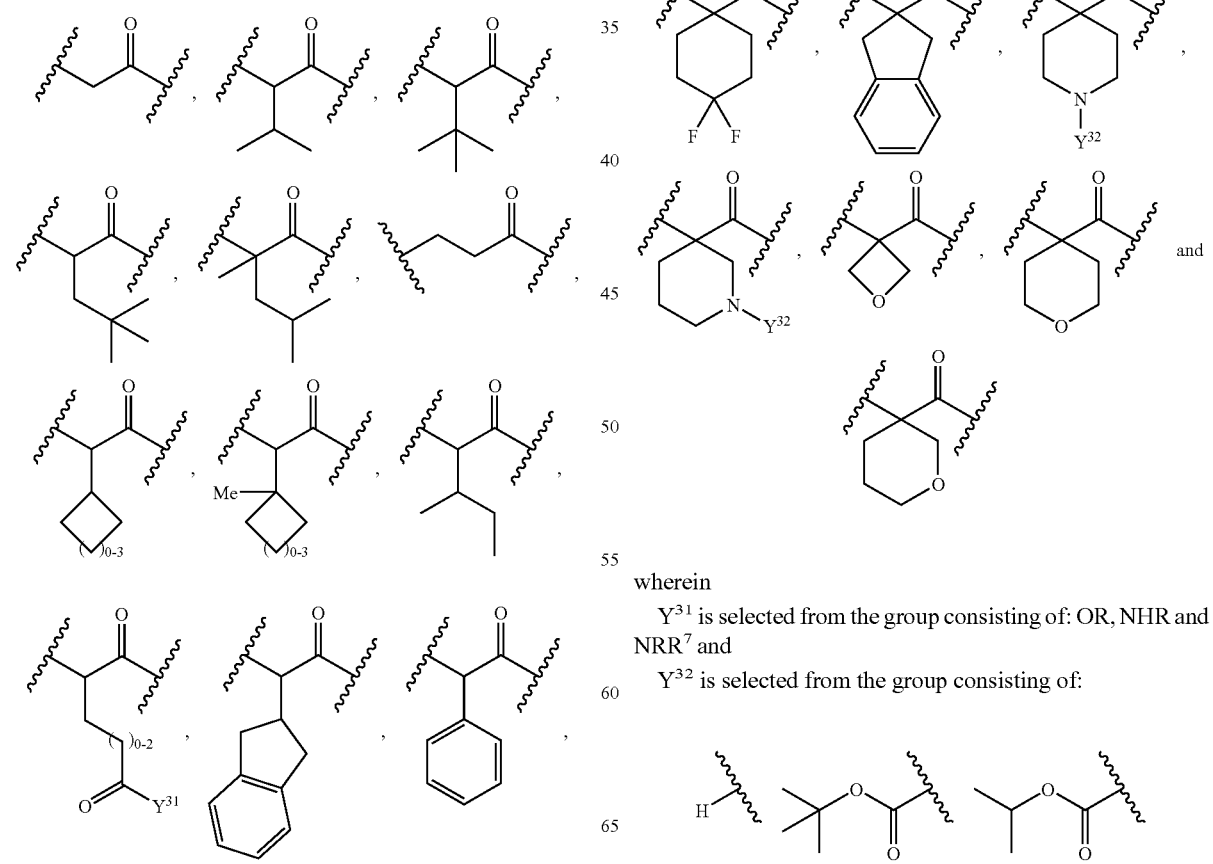
wherein
$Y^{31}$ is selected from the group consisting of: OR, NHR and $NRR^7$ and
$Y^{32}$ is selected from the group consisting of:

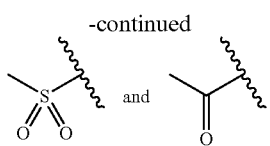 and
In another embodiment, Z is NH.
In another embodiment, Z is N(R).
In another embodiment, Z is O; when Z is O, then G can be present or absent, and if G is present with Z being O, then G is C(=O).
In another embodiment, G is present and G is C(=O) or S(O₂).
In another embodiment, G is absent.
In another embodiment, Y is selected from the group consisting of:
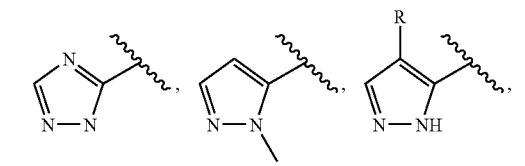
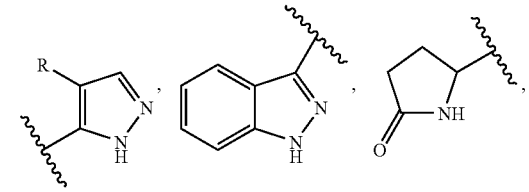
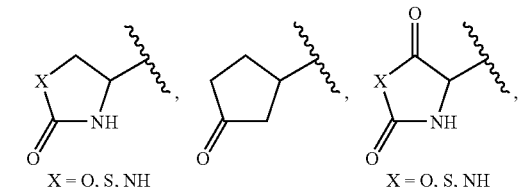
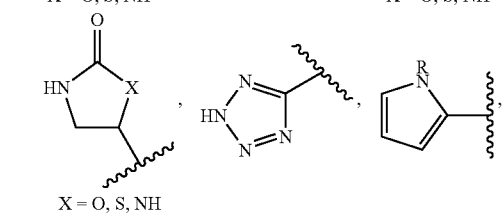
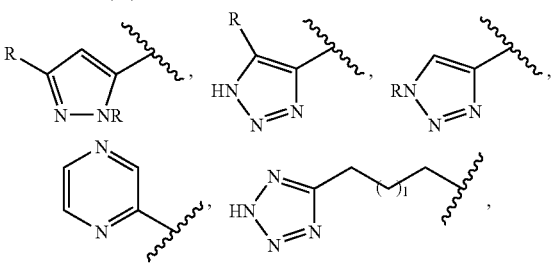
l = 0-4
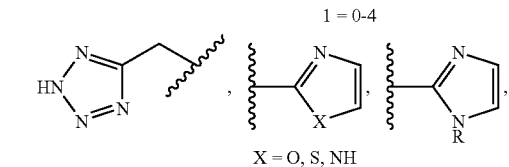
X = O, S, NH
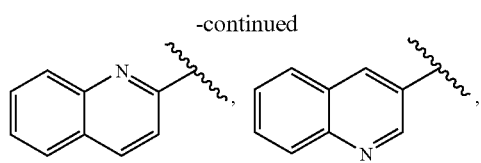
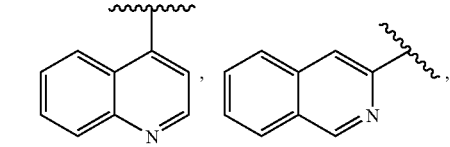
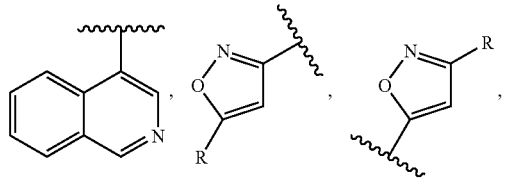
X = O, S, NH    X = O, S, NH
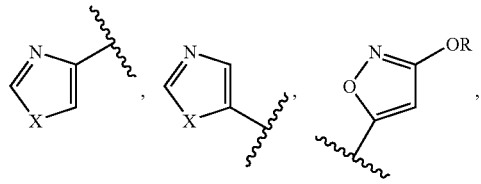
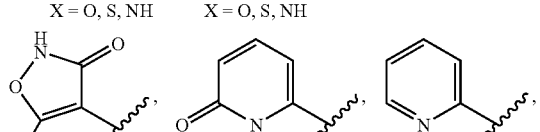
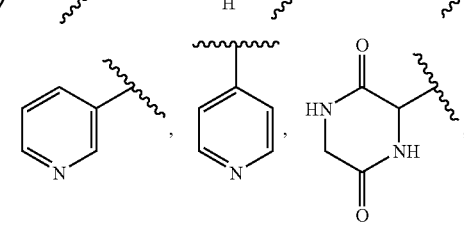
X = O, S, NH
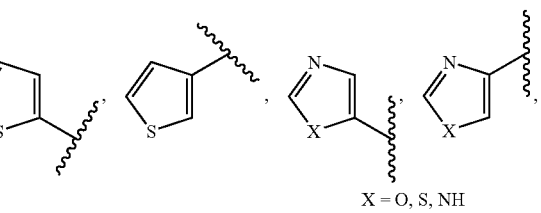
A = O, NH
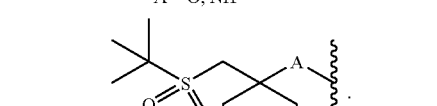

In another embodiment, the moiety:

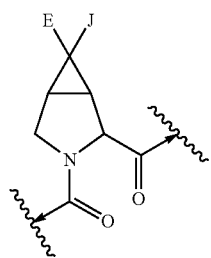

is selected from the group consisting of:

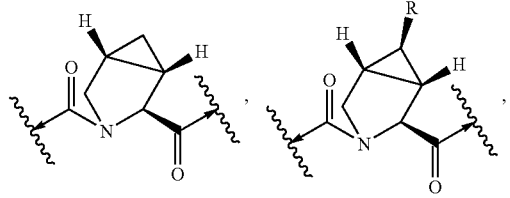

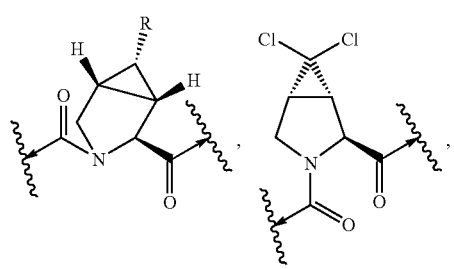

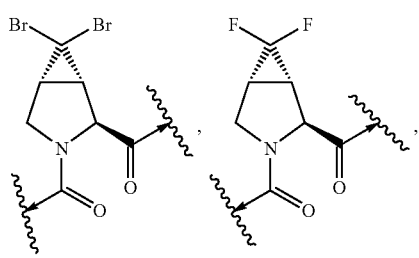

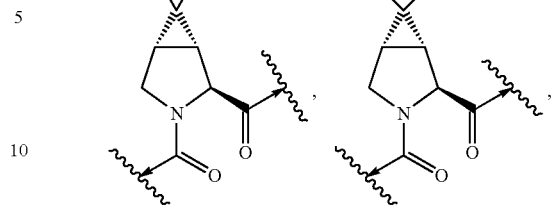

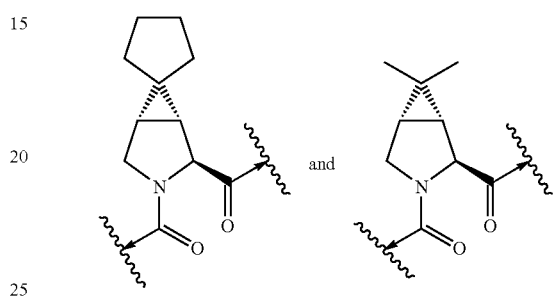

In general, the arrow-containing designations on a moiety represent the connecting points of the moiety to the respective positions shown in the parent structure, e.g., in Formula I.

Yet another embodiment of the invention discloses some of the inventive compounds of Formula I in Table 1. Also disclosed in Table 1 is the NS3/NS4a serine protease inhibitory activity (Ki* in nanoMolar) for some of the inventive compounds.

TABLE I

| Entry | Structure | Ki* (nM) |
|---|---|---|
| 1 | 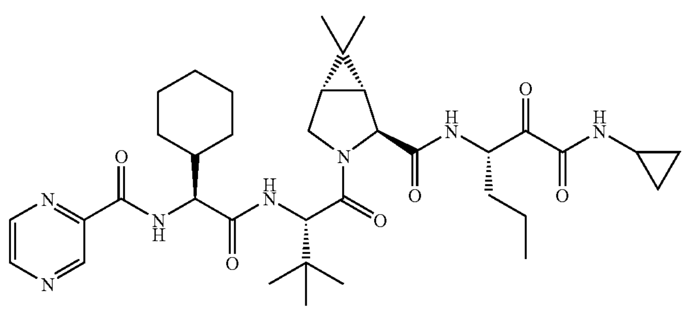 | 10 |

TABLE I-continued

| Entry | Structure | Ki* (nM) |
|---|---|---|
| 2 | 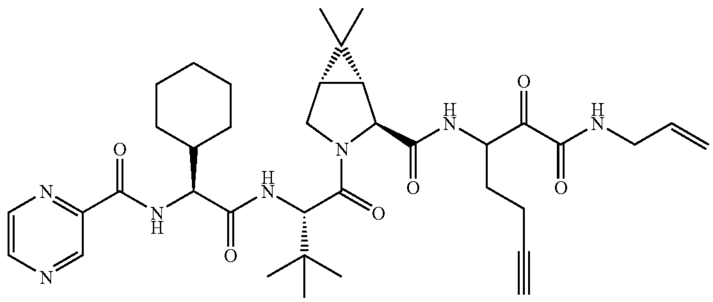 | 6 |
| 3 | 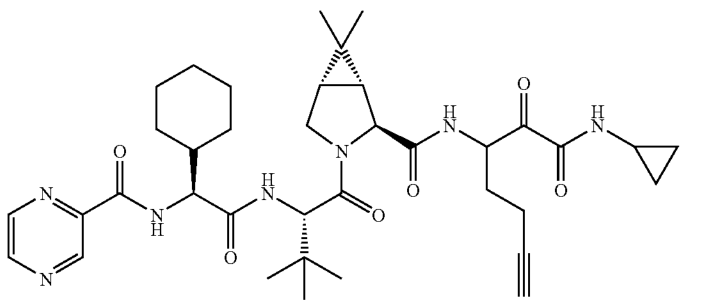 | |
| 4 | 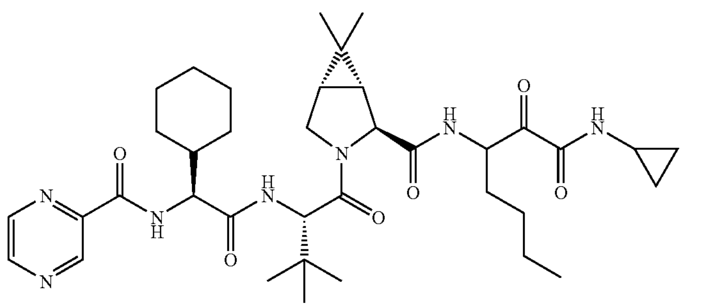 | |
| 5 | 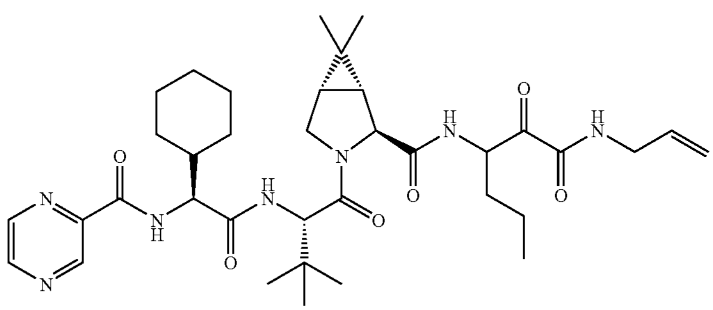 | |
| 6 | 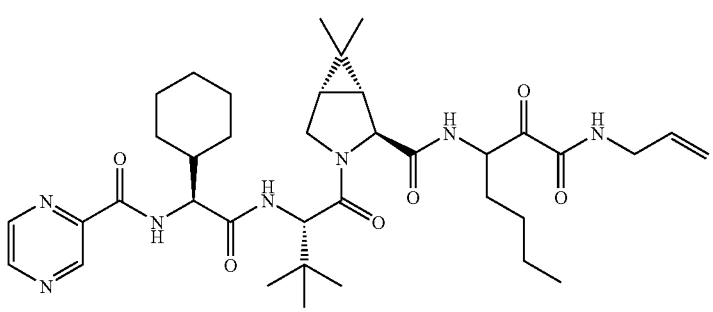 | |

TABLE I-continued

| Entry | Structure | Ki* (nM) |
|---|---|---|
| 7 | 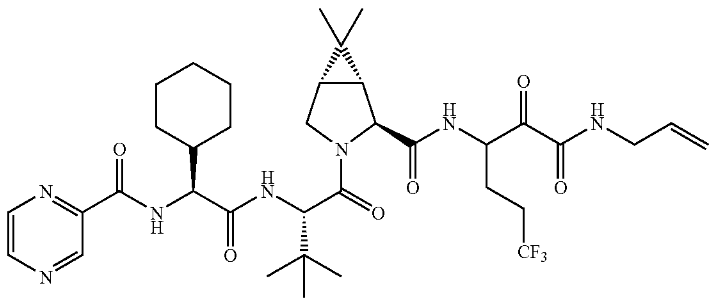 | |
| 8 | 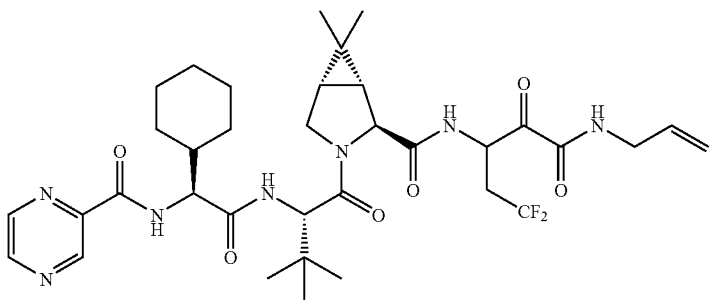 | |
| 9 | 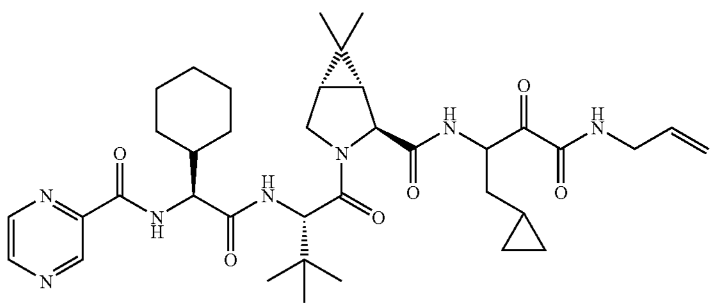 | |
| 10 | 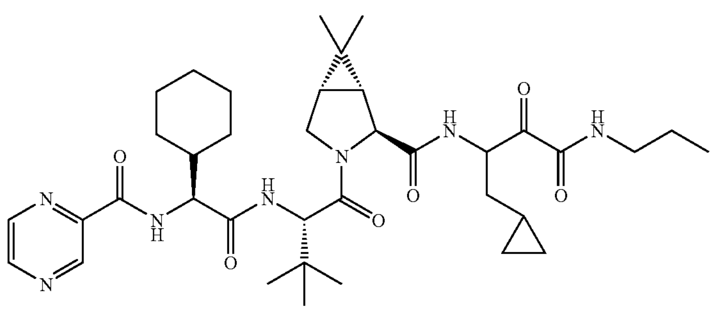 | |
| 11 | 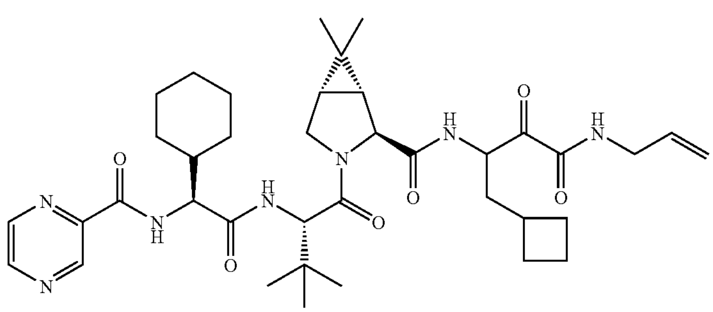 | |

TABLE I-continued

| Entry | Structure | Ki* (nM) |
|---|---|---|
| 12 | 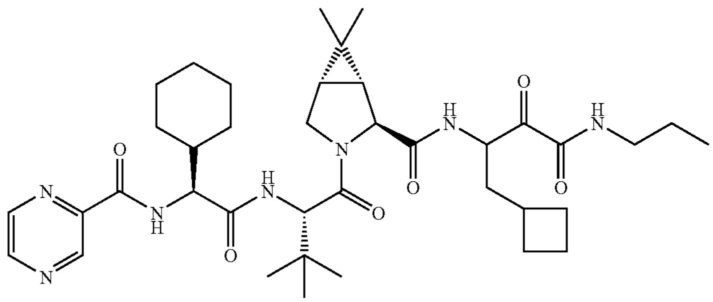 | |
| 13 | 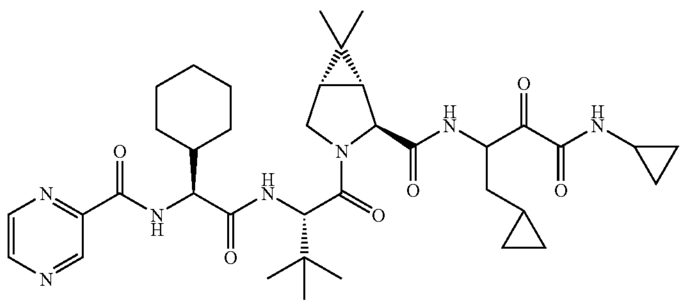 | |
| 14 | 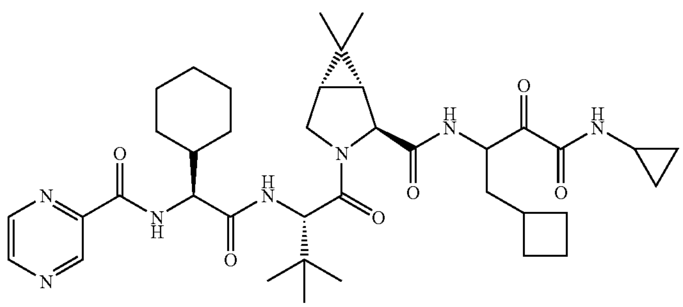 | |
| 15 | 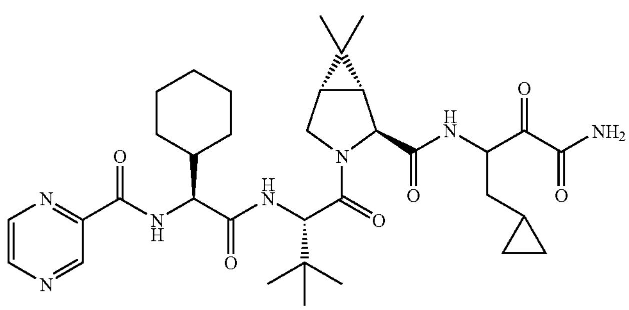 | |
| 16 | 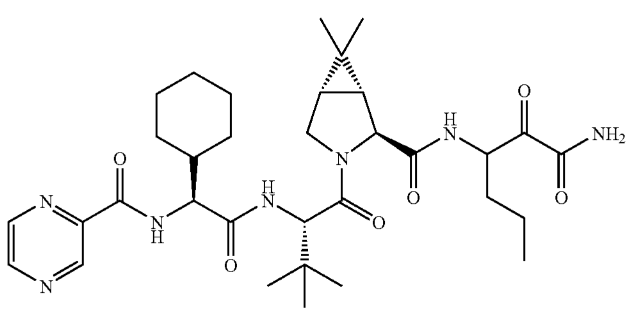 | |

TABLE I-continued

| Entry | Structure | Ki* (nM) |
|---|---|---|
| 17 | 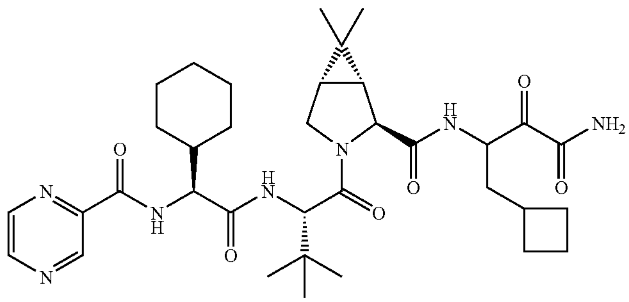 | |
| 18 | 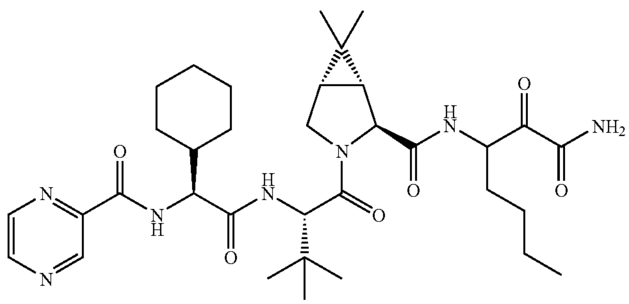 | |
| 19 | 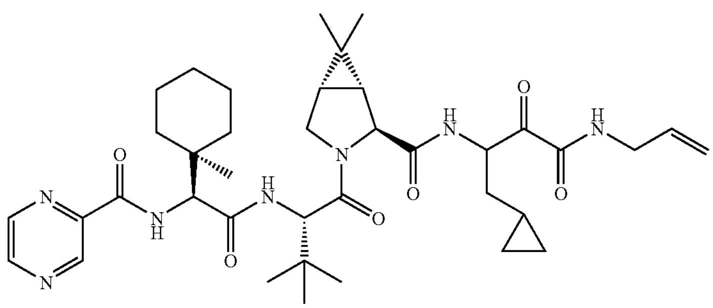 | |
| 20 | 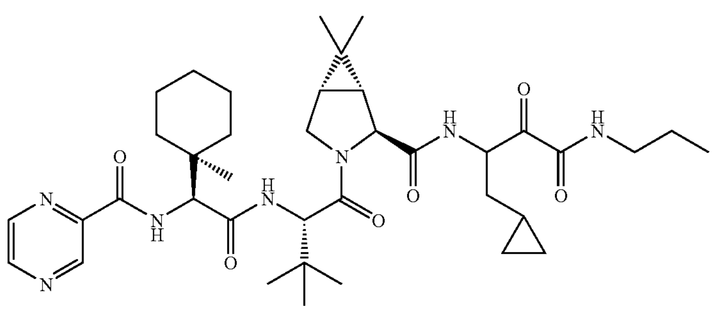 | |
| 21 | 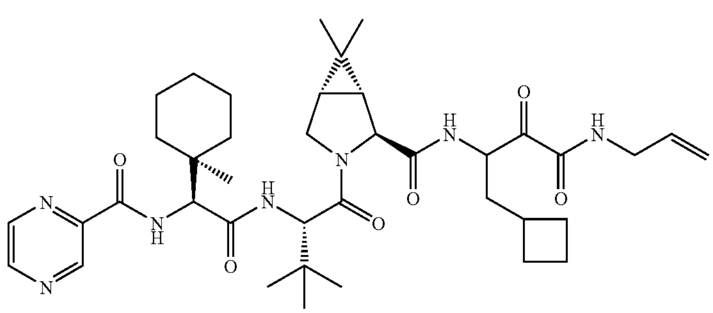 | |

TABLE I-continued

| Entry | Structure | Ki* (nM) |
|---|---|---|
| 22 | 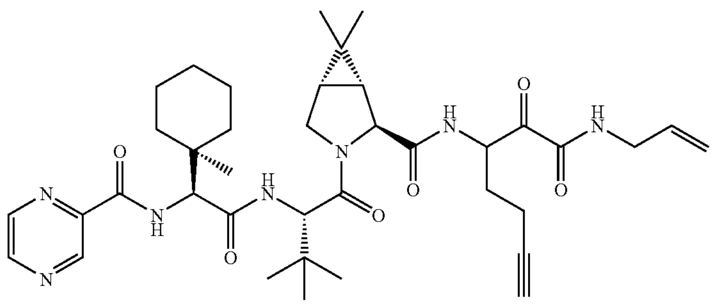 | |
| 23 | 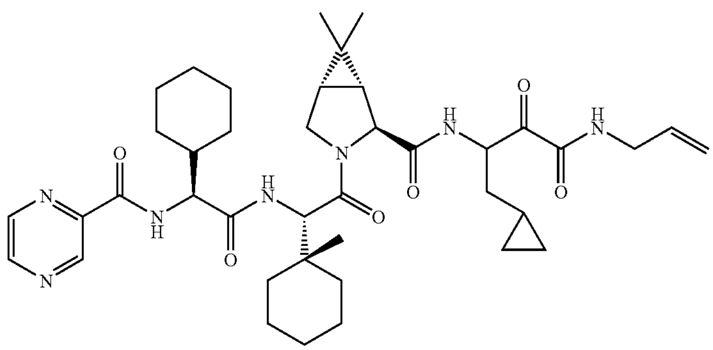 | |
| 24 | 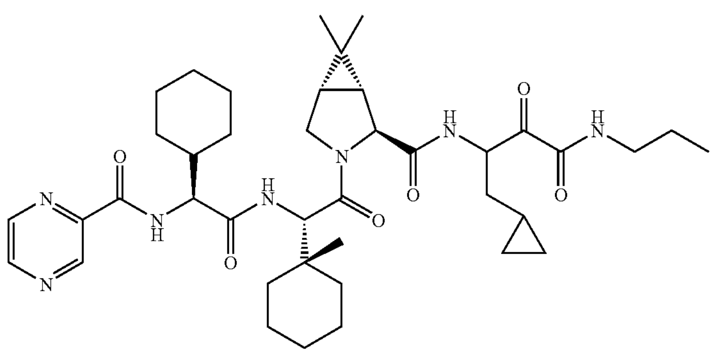 | |
| 25 | 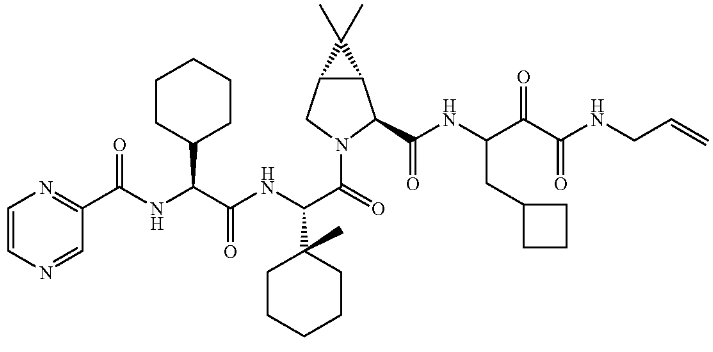 | |

TABLE I-continued
| Entry | Structure | Ki* (nM) |
|---|---|---|
| 26 | 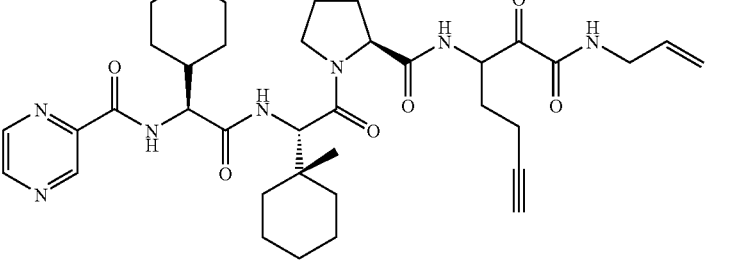 | |
| 27 | 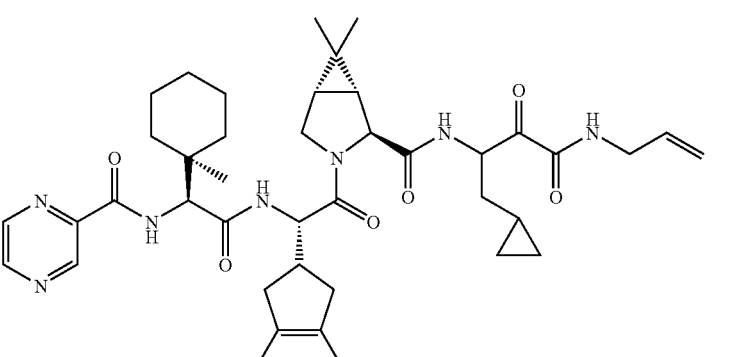 | |
| 28 | 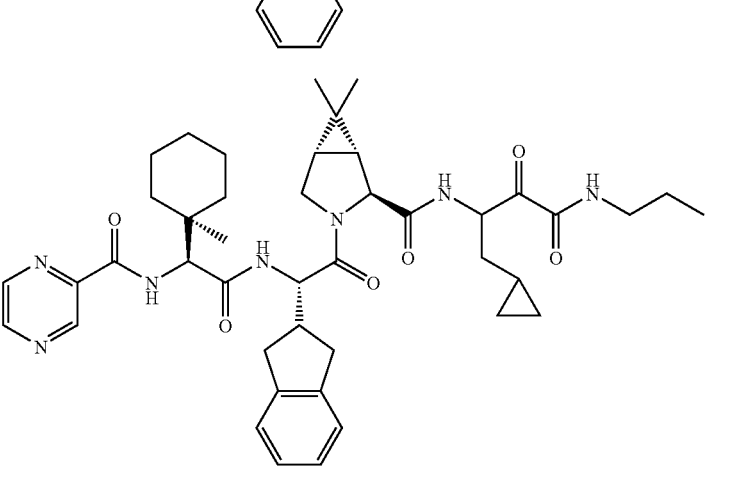 | |
| 29 | 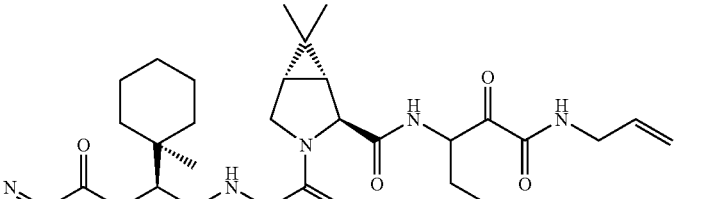 | |

TABLE I-continued

| Entry | Structure | Ki* (nM) |
|---|---|---|
| 30 | 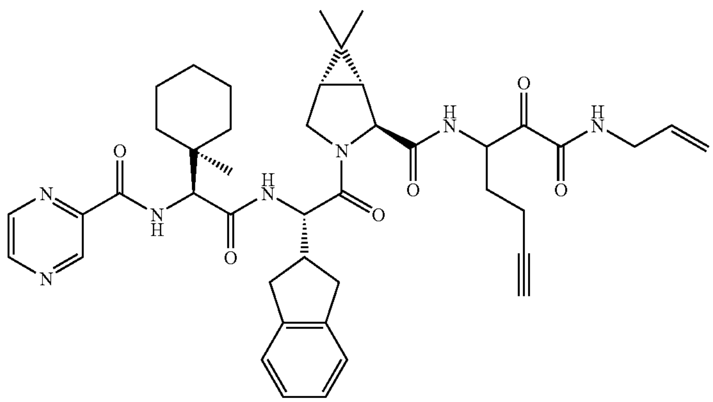 | |
| 31 | 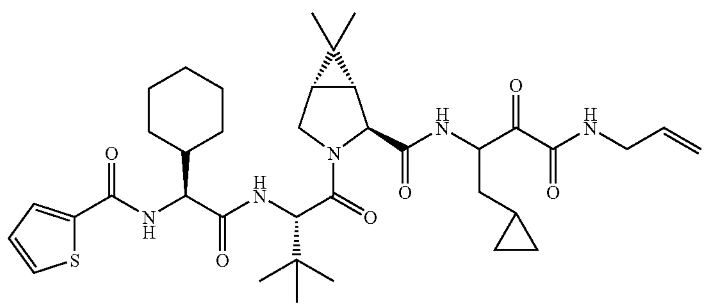 | |
| 32 | 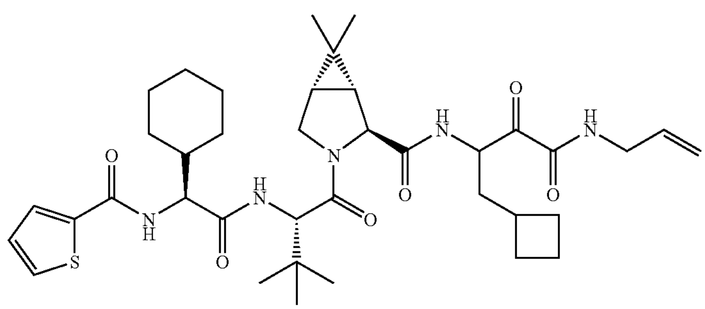 | |
| 33 | 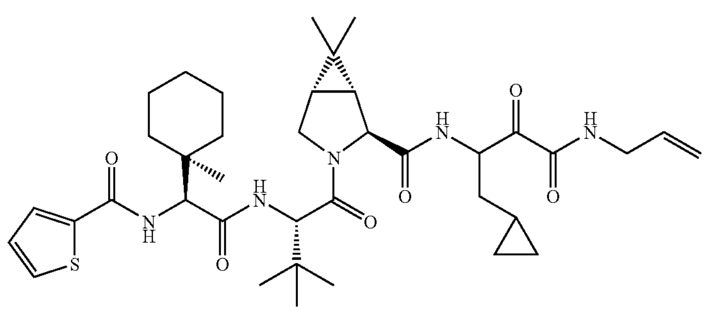 | |

TABLE I-continued

| Entry | Structure | Ki* (nM) |
|-------|-----------|----------|
| 34 | 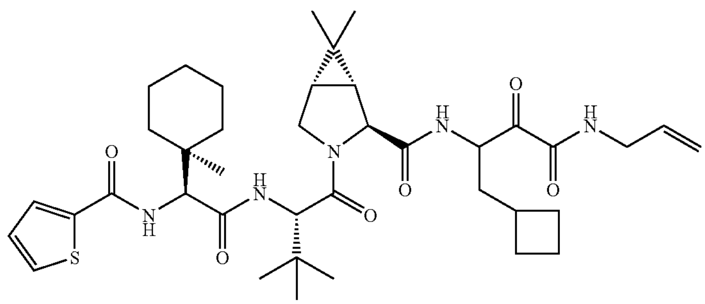 | |
| 35 | 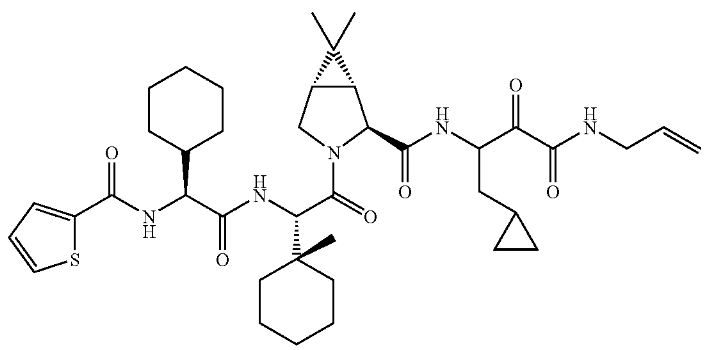 | |
| 36 | 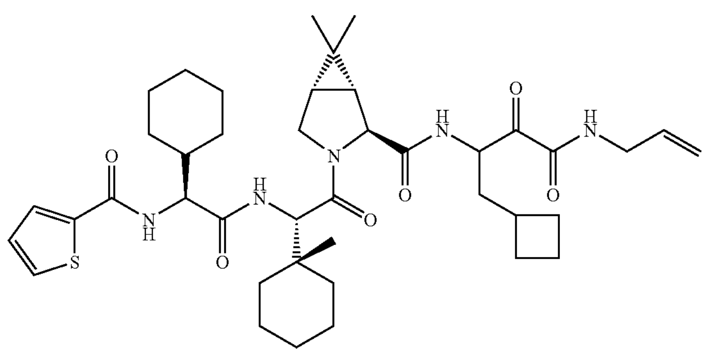 | |
| 37 | 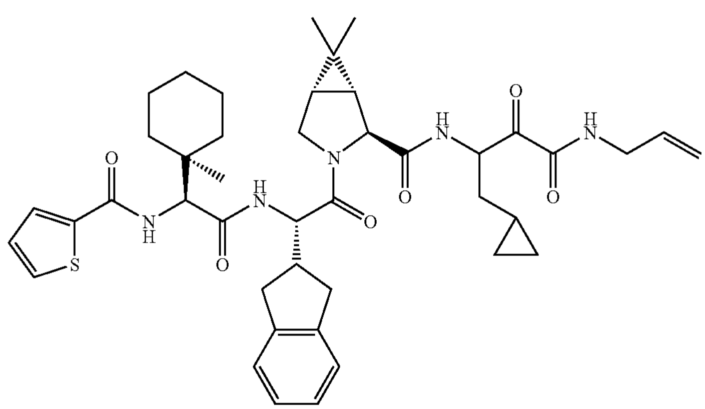 | |

TABLE I-continued

| Entry | Structure | Ki* (nM) |
|---|---|---|
| 38 | 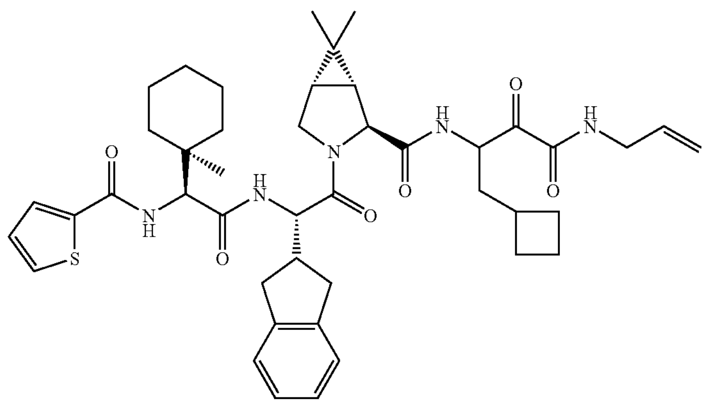 | |
| 39 | 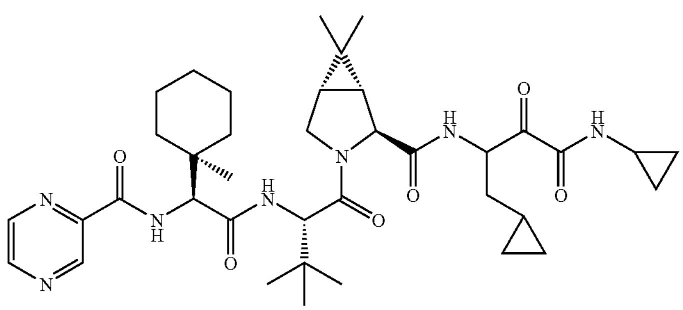 | |
| 40 | 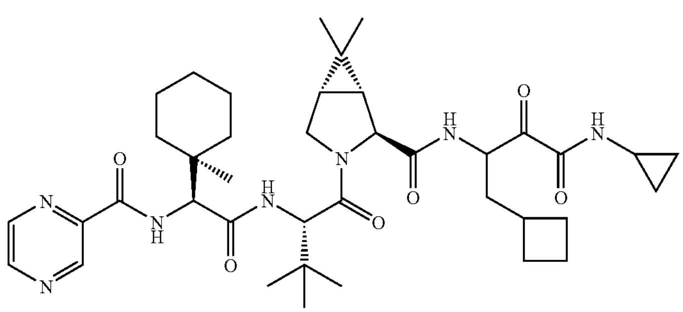 | |
| 41 | 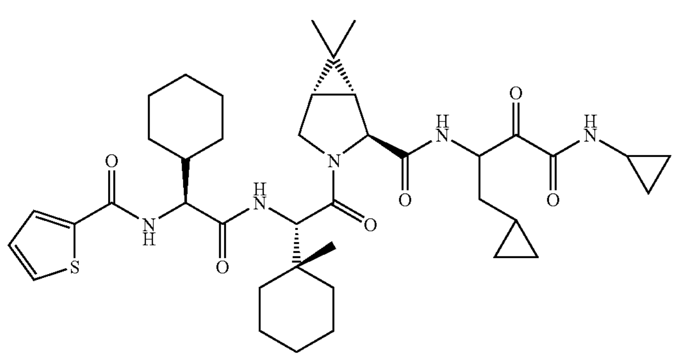 | |

TABLE I-continued

| Entry | Structure | Ki* (nM) |
|---|---|---|
| 42 | 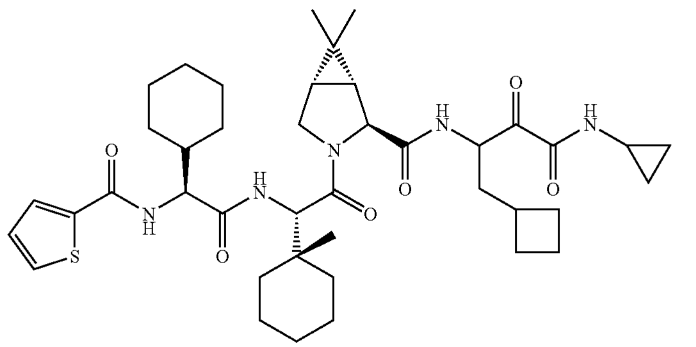 | |
| 43 | 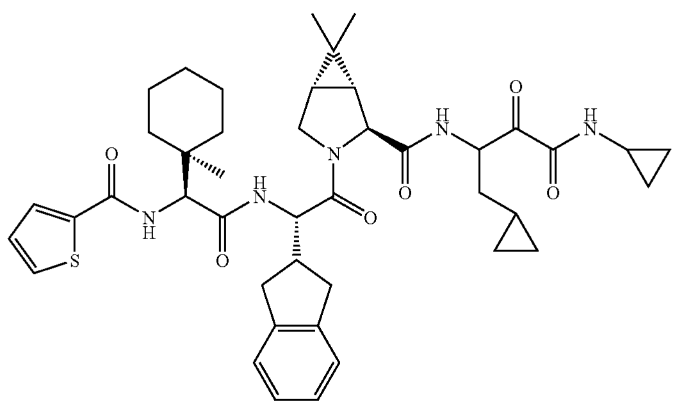 | |
| 44 | 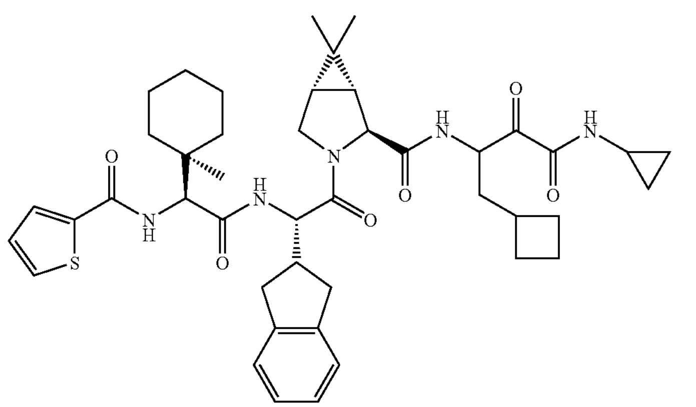 | |
| 45 | 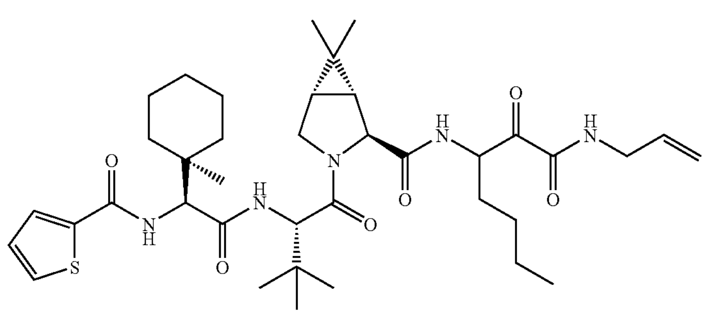 | |

TABLE I-continued
| Entry | Structure | Ki* (nM) |
|---|---|---|
| 46 | 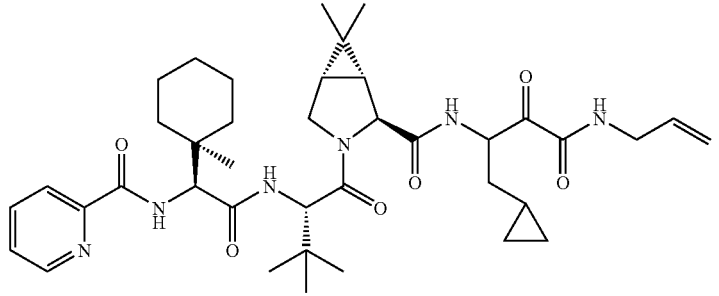 | |
| 47 | 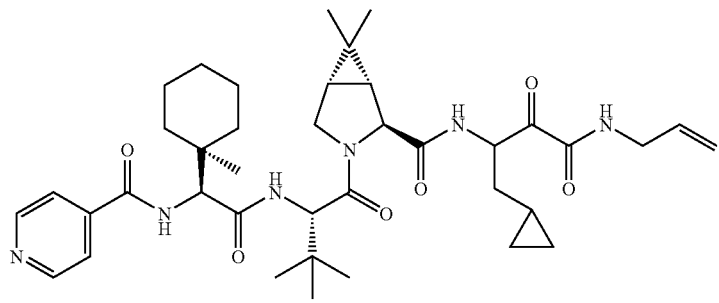 | |
| 48 | 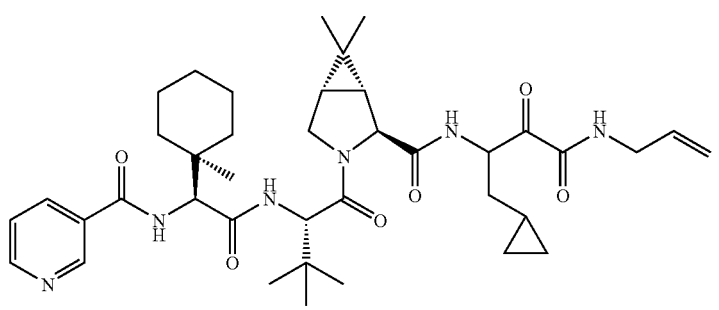 | |
| 49 | 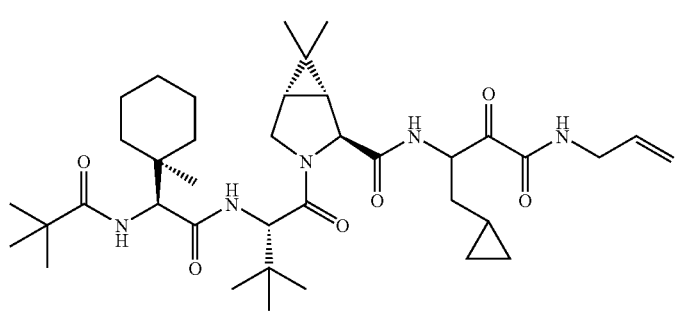 | |
| 50 | 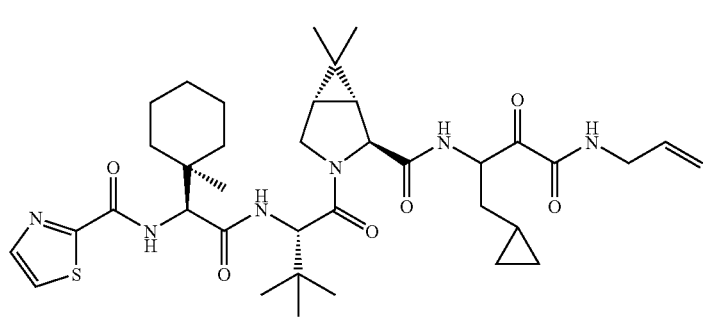 | |

TABLE I-continued
| Entry | Structure | Ki* (nM) |
|---|---|---|
| 51 | 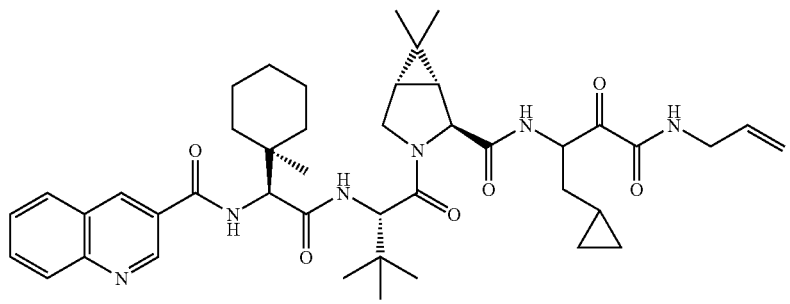 | |
| 52 | 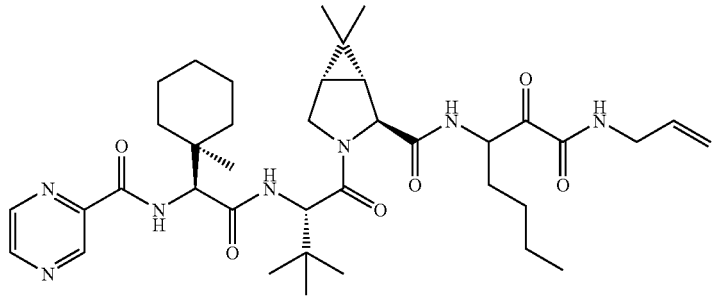 | |
| 53 | 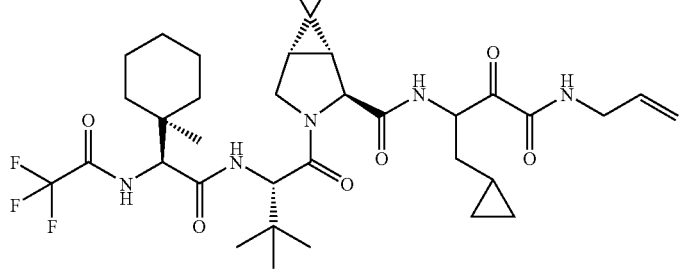 | |
| 54 | 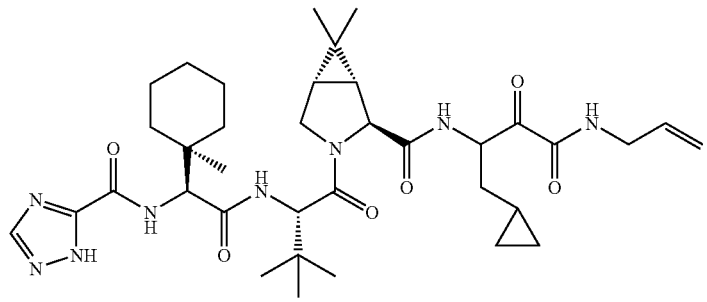 | |
| 55 | 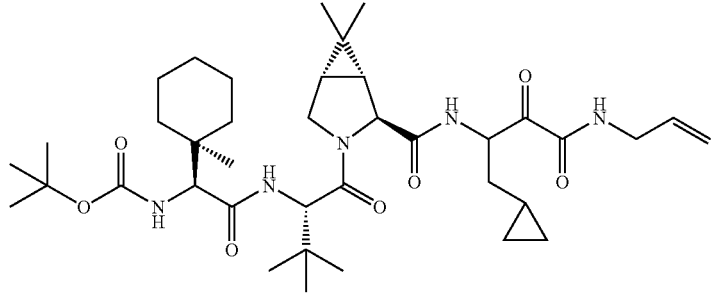 | |

TABLE I-continued

| Entry | Structure | Ki* (nM) |
|---|---|---|
| 56 | 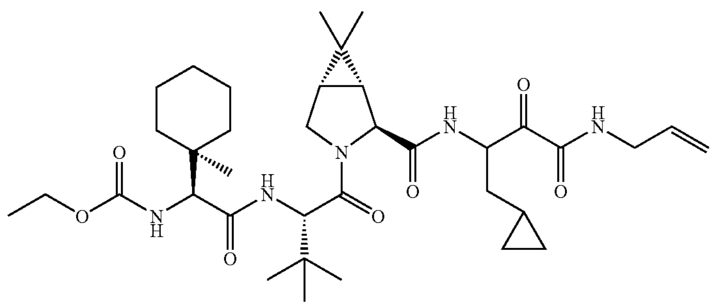 | |
| 57 | 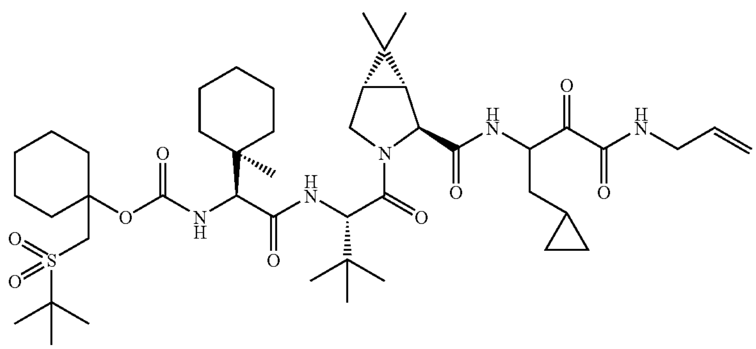 | |
| 58 | 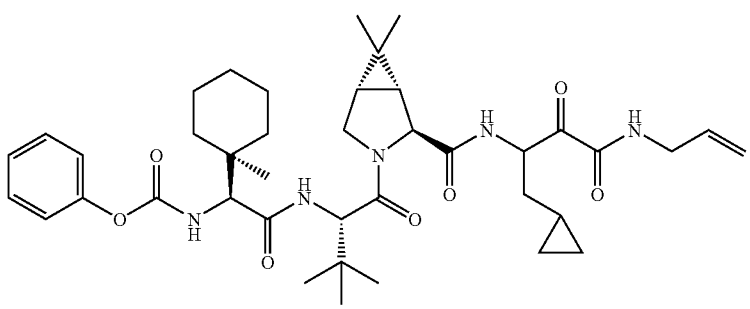 | |
| 59 | 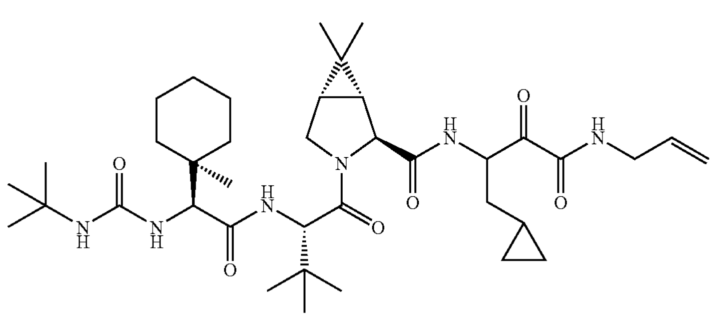 | |

TABLE I-continued

| Entry | Structure | Ki* (nM) |
|---|---|---|
| 60 | 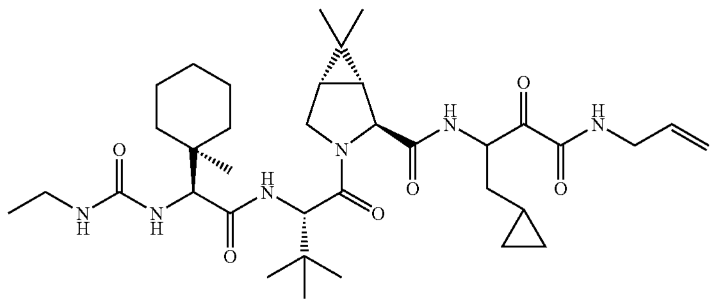 | |
| 61 | 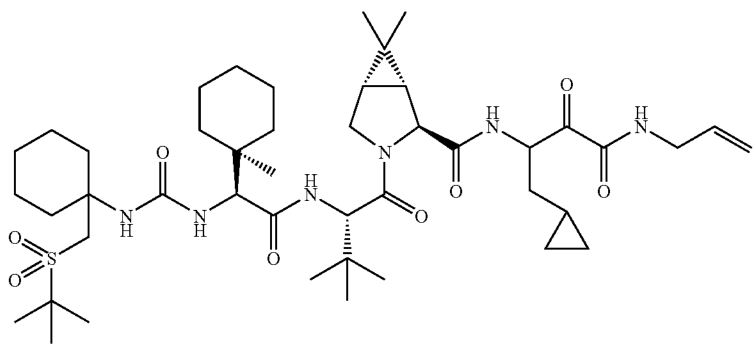 | |
| 62 | 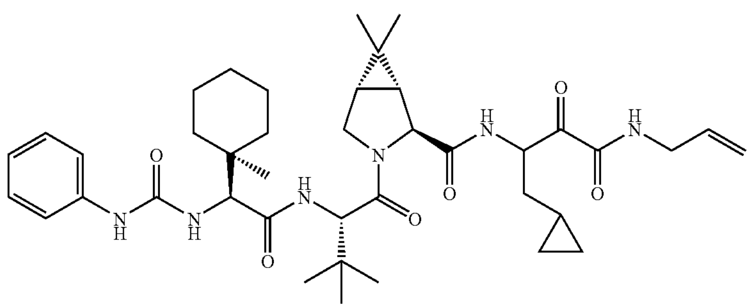 | |
| 63 | 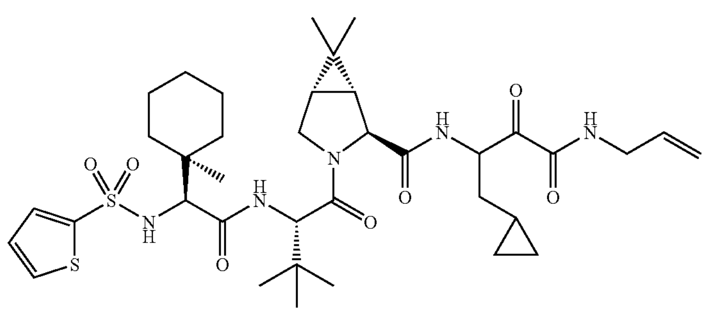 | |

TABLE I-continued

| Entry | Structure | Ki* (nM) |
|---|---|---|
| 64 | 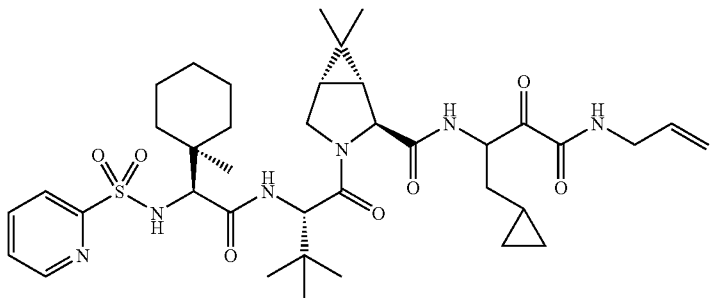 | |
| 65 | 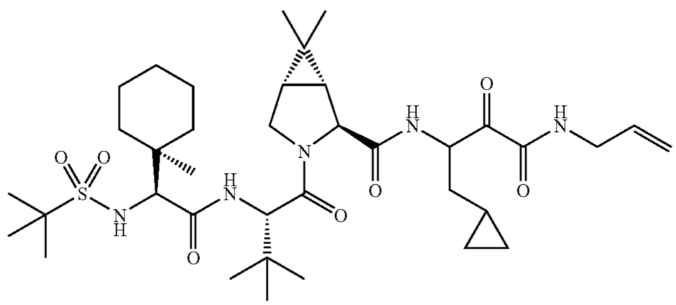 | |
| 66 | 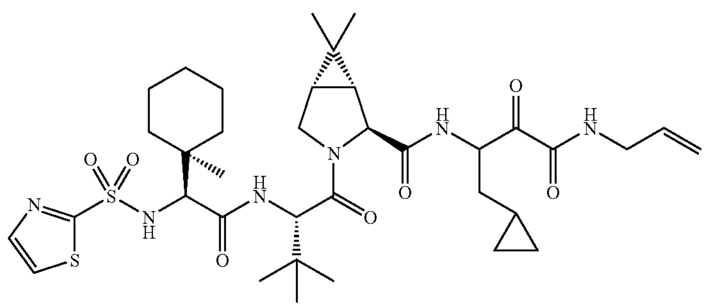 | |
| 67 | 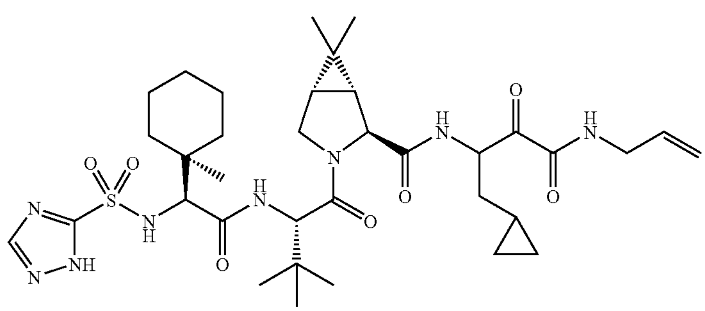 | |
| 68 | 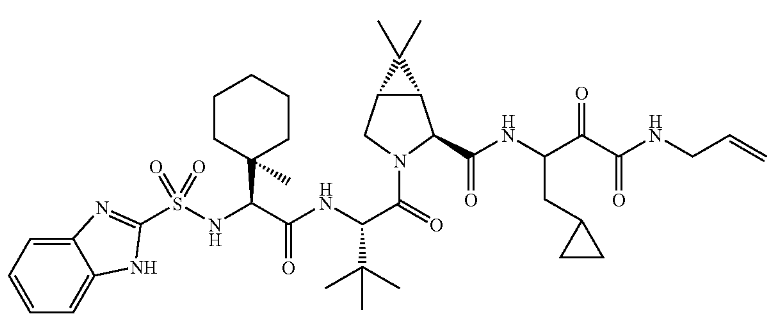 | |

TABLE I-continued

| Entry | Structure | Ki* (nM) |
|---|---|---|
| 69 | 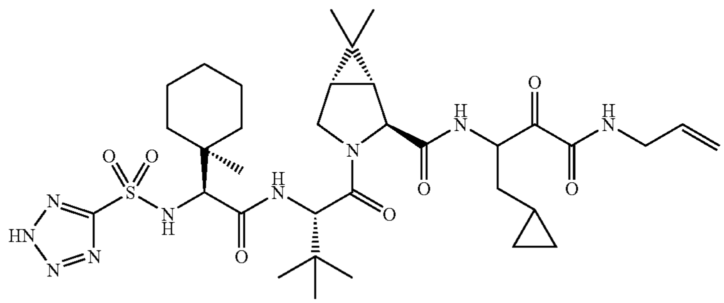 | |
| 70 | 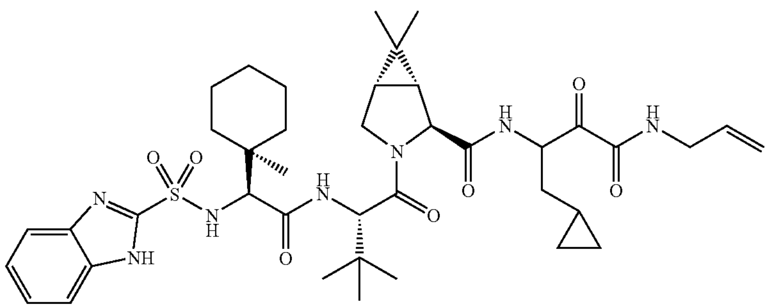 | |
| 71 | 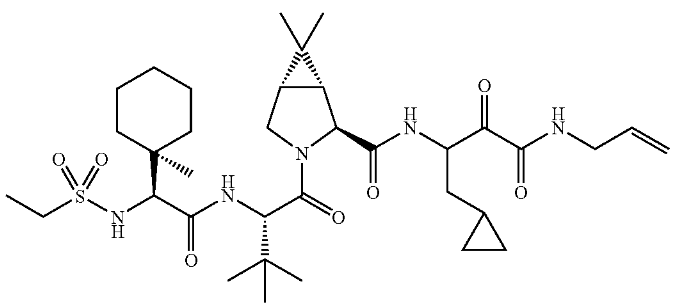 | |
| 72 | 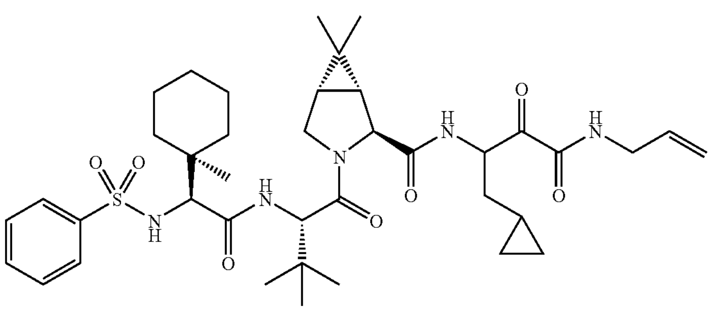 | |

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" or "halo" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

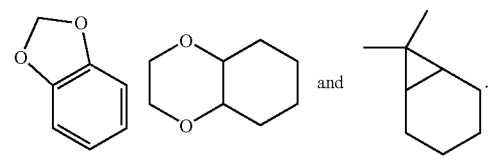

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

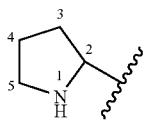

there is no —OH attached directly to carbons marked 2 and 5.

It should also be noted that tautomeric forms such as, for example, the moieties:

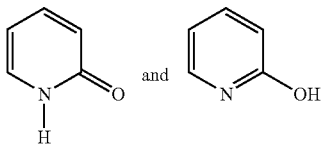

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—C(O)— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "one or more" or "at least one", when indicating the number of substituents, compounds, combination agents and the like, refers to at least one, and up to the maximum number of chemically and physically permissible, substituents, compounds, combination agents and the like, that are present or added, depending on the context. Such techniques and knowledge are well known within the skills of the concerned artisan.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula 1, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1 or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formula 1 can form salts which are also within the scope of this invention. Reference to a compound of Formula 1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula 1 may be formed, for example, by reacting a compound of Formula 1 with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula 1, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prod rug of enantiomers, stereoisomers, rotamers, tautomers, positional isomers, racemates or prodrugs of the inventive compounds.

Compounds of Formula 1, and salts, solvates and prodrugs thereof, may exist in their polymorphic forms. Polymorphic forms of the compounds of Formula I, and of the salts, solvates and prodrugs of the compounds of Formula I, are intended to be included in the present invention.

All such polymorphic form or forms are contemplated herein as part of the present invention.

It is to be understood that the utility of the compounds of Formula 1 for the therapeutic applications discussed herein is applicable to each compound by itself or to the combination or combinations of one or more compounds of Formula 1 as illustrated, for example, in the next immediate paragraph. The same understanding also applies to pharmaceutical composition(s) comprising such compound or compounds and method(s) of treatment involving such compound or compounds.

The compounds according to the invention can have pharmacological properties; in particular, the compounds of Formula 1 can be inhibitors of HCV protease, each compound by itself or one or more compounds of Formula 1 can be combined with one or more compounds selected from within Formula 1. The compound(s) can be useful for treating diseases such as, for example, HCV, HIV, (AIDS, Acquired Immune Deficiency Syndrome), and related disorders, as well as for modulating the activity of hepatitis C virus (HCV) protease, preventing HCV, or ameliorating one or more symptoms of hepatitis C.

The compounds of Formula 1 may be used for the manufacture of a medicament to treat disorders associated with the HCV protease, for example, the method comprising bringing into intimate contact a compound of Formula 1 a pharmaceutically acceptable carrier.

In another embodiment, this invention provides pharmaceutical compositions comprising the inventive compound or compounds as an active ingredient. The pharmaceutical compositions generally additionally comprise at least one pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

The compounds of the invention may also be administered orally, intravenously, intranasally or subcutaneously.

The compounds of the invention may also comprise preparations which are in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the inventive compounds or pharmaceutical compositions disclosed above for treatment of diseases such as, for example, hepatitis C and the like. The method comprises administering a therapeutically effective amount of the inventive compound or pharmaceutical composition to a patient having such a disease or diseases and in need of such a treatment.

In yet another embodiment, the compounds of the invention may be used for the treatment of HCV in humans in monotherapy mode or in a combination therapy (e.g., dual combination, triple combination etc.) mode such as, for example, in combination with antiviral and/or immunomodulatory agents. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP 50406™ (from Viropharma, Incorporated, Exton, Penn.), ISIS 14803™

(from ISIS Pharmaceuticals, Carlsbad, Calif.), Heptazyme™ (from Ribozyme Pharmaceuticals, Boulder, Colo.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-La-Roche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Illustrative procedures are outlined in the following reaction schemes. The illustrations should not be construed to limit the scope of the invention which is defined in the appended claims. Alternative mechanistic pathways and analogous structures will be apparent to those skilled in the art.

It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

For the procedures described below, the following abbreviations are used:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et2O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
iBoc: isobutoxycarbonyl
iPr: isopropyl
$^t$Bu or Bu$^t$: tert-Butyl
Boc: tert-Butyloxycarbonyl
Cbz: Benzyloxycarbonyl
Cp: Cylcopentyldienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
BOP: Benzotriazol-1-yl-oxy-tris(dimethylamino)hexafluorophosphate
PCC: Pyridiniumchlorochromate
KHMDS: Potassium Hexamethyldisilazide or Potassium bis(trimethylsilylamide)
NaHMDS: Sodium Hexamethyldisilazide or Sodium bis(trimethylsilylamide)
LiHMDS: Lithium Hexamethyidisilazide or Lithium bis(trimethylsilylamide)
10% Pd/C: 10% Palladium on carbon (by weight).

PREPARATIVE EXAMPLE 1

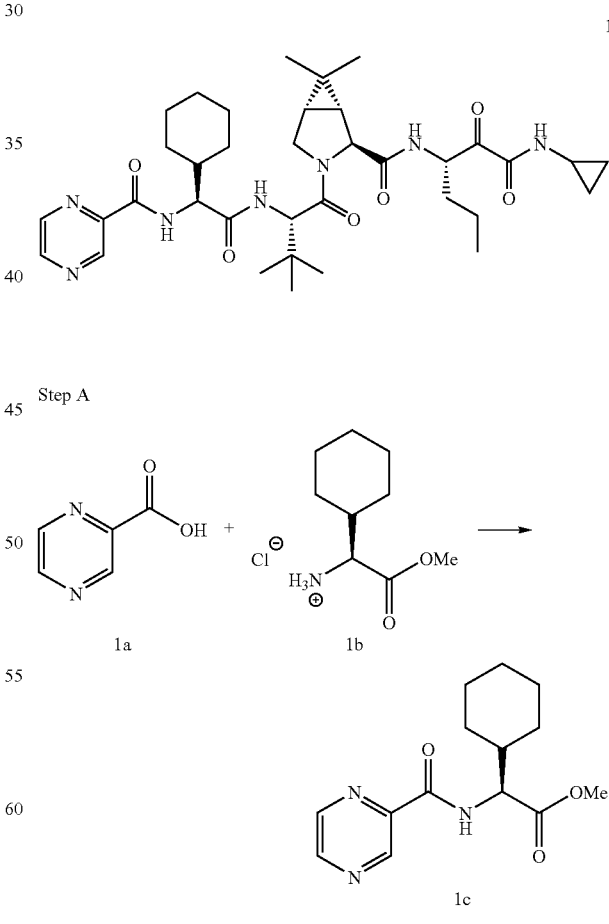

Step A

A solution of pyrazinecarboxylic acid 1a (3 g) in 150 mL of dry dichloromethane and 150 mL of dry DMF was stirred at 0° C. and treated with HATU (1.4 eq, 6.03 g). L-cyclohexylglycine hydrochloride 1b (1.2 eq, 6.03 g) was added in small portions. Then, N-methylmorpholine (4 eq, 10 mL, d 0.920) was added dropwise. The reaction mixture was gradually warmed to room temperature and stirred for 20 h. All the volatiles were removed under vacuum and the residue was dissolved in 500 mL of ethyl acetate. The organic layer was washed with water (100 mL), aqueous 1 N HCl (100 mL), aqueous saturated sodium bicarbonate solution (100 mL), and brine (100 mL). The organic layer was dried over magnesium sulfate, filtered and concentrated under reduced pressure. The residue was chromatographed on silica gel (gradient: acetone/hexanes; 5:95 to 3:7) to afford the product as a white solid.

Step B

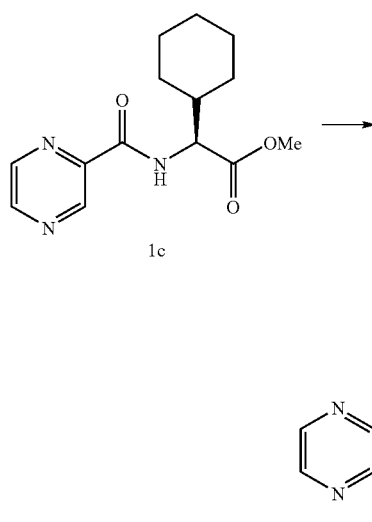

A solution of the methyl ester 1c (6.5 g) in 270 mL of a 1:1:1 mixture of THF/MeOH/water was cooled to 0° C. and treated with lithium hydroxide monohydrate (2.5 eq, 2.45 g). The mixture was stirred and monitored by TLC (acetone/hexanes; 2:8). When all the starting material had been consumed, the reaction mixture was treated with 100 mL of aqueous 1N HCl and the mixture was concentrated on the rotovap. Dichloromethane (250 mL) was added and layers separated. The aqueous layer was extracted with dichloromethane (3×80 mL). The combined organic layers were dried over magnesium sulfate, filtered, and concentrated to afford the product as a white solid.

Step C

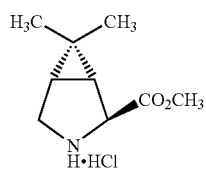

The amino ester 1e was prepared following the method of R. Zhang and J. S. Madalengoitia (*J. Org. Chem.* 1999, 64, 330), with the exception that the Boc group was cleaved by the reaction of the Boc-protected amino acid with methanolic HCl (4M HCl in dioxane was also employed for the deprotection).

(Note: In a variation of the reported synthesis, the sulfonium ylide was replaced with the corresponding phosphonium ylide).

Step D

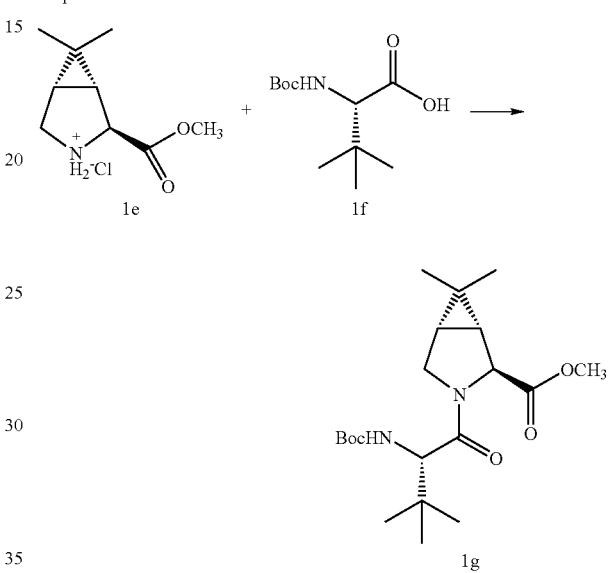

A solution of Boc-tert-Leu 1f (Fluka, 5.0 g, 21.6 mmol) in dry $CH_2Cl_2$/DMF (50 mL, 1:1) was cooled to 0° C. and treated with the amine hydrochloride 1f (5.3 g, 25.7 mmol), NMM (6.5 g, 64.8 mmol) and BOP reagent (11.6 g, 25.7 mmol). The reaction was stirred at rt. for 24 h, diluted with aqueous HCl (1 M) and extracted with $CH_2Cl_2$. The combined organic layers were washed with aqueous 1M HCl, saturated $NaHCO_3$, brine, dried ($MgSO_4$), filtered and concentrated in vacuo and purified by chromatography ($SiO_2$, Acetone/Hexane 1:5) to yield 1g as a colorless solid.

Step E

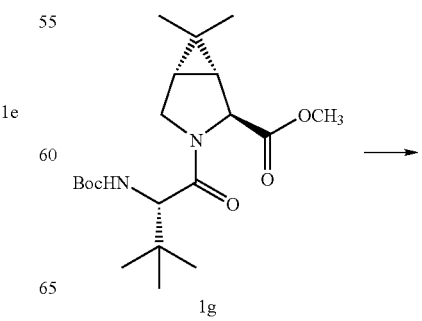

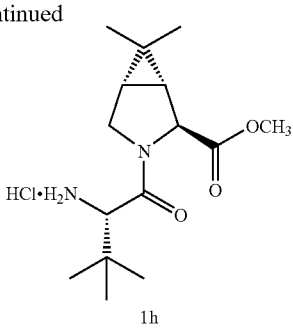
1h

A solution of methyl ester 1g (4.0 g, 10.46 mmol) was dissolved in 4M HCl in dioxane and stirred at rt. for 3 h. The reaction mixture was concentrated in vacuo to obtain the amine hydrochloride salt, 1h which was used without purification.

Step F

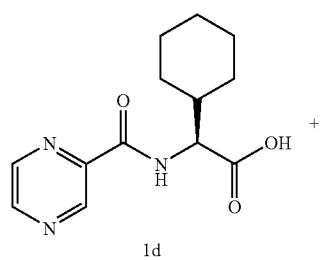
1d

+

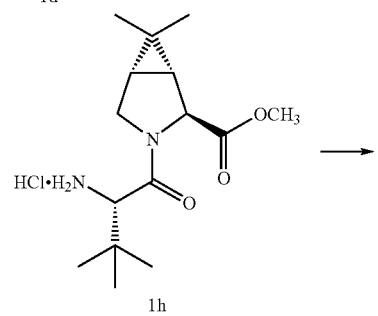
1h

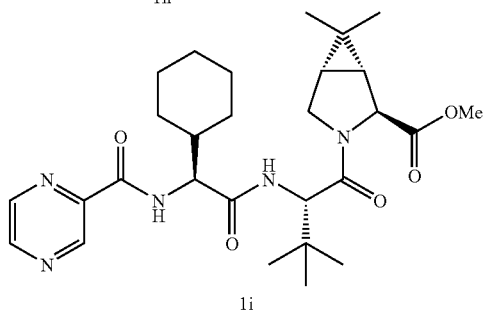
1i

A solution of acid 1d (100 mg) in 5 mL of dry dichloromethane and 5 mL of dry DMF was stirred at 0° C. and treated with HATU (1.4 eq, 202 mg). The amine hydrochloride 1h (1.2 eq, 146 mg) was added. Then, N-methylmorpholine (4 eq, 0.17 mL, d 0.920) was also added. The reaction mixture was stirred at 0° C. overnight. All the volatiles were removed under vacuum and the residue was dissolved in 80 mL of ethyl acetate. The organic layer was washed with water (10 mL), aqueous 1N HCl (10 mL), aqueous saturated sodium bicarbonate solution (10 mL), and brine (10 mL). The organic layer was dried over magnesium sulfate, filtered and concentrated under reduced pressure. The residue was chromatographed on silica gel (gradient: acetone/hexanes; 1:9 to 4:6) to afford the product 1i as a white solid.

Step G

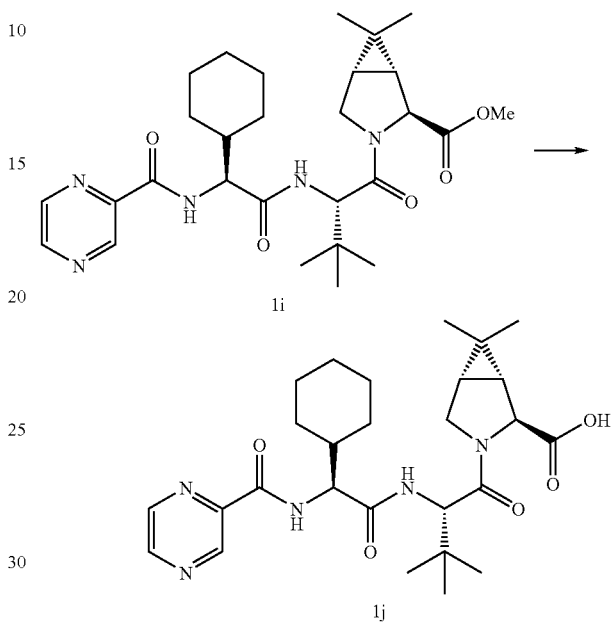
1i

1j

A solution of methyl ester 1i (180 mg) in 9 mL of a 1:1:1 mixture of THF/MeOH/water was cooled to 0° C. and treated with lithium hydroxide monohydrate (2.5 eq, 35 mg). The mixture was stirred and monitored by TLC (acetone/hexanes; 3:7). When all the starting material had been consumed, the reaction mixture was treated with 50 mL of aqueous 1N HCl and the mixture was concentrated on the rotovap. Dichloromethane (80 mL) was added and layers separated. The aqueous layer was extracted with dichloromethane (3×50 mL). The combined organic layers were dried over magnesium sulfate, filtered, and concentrated to afford the product 1j as a white solid.

Step H

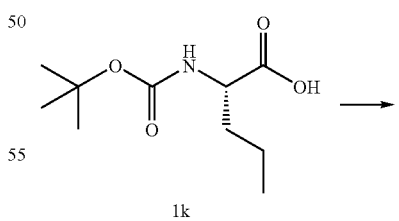
1k

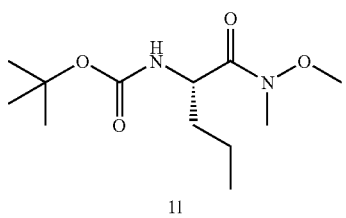
1l

A solution of acid 1k (2 g) in 100 mL of dry dichloromethane and 5 mL of DMF was treated with N,O-dimethylhydroxylamine hydrochloride (1.1 eq, 986 mg), BOP reagent (1.1 eq, 4.47 g), and N-methylmorpholine (3.3 eq, 3.3 mL, d 0.920) in that order. The mixture was heated to 50° C. overnight. The reaction mixture was concentrated to half its volume and diluted with 400 mL of ethyl acetate. The organic layer was washed with water (80 mL), aqueous 1M HCl (80 mL), aqueous saturated sodium bicarbonate solution (80 mL), and brine (80 mL). The organic layer was dried over magnesium sulfate, filtered, and concentrated under reduced pressure. The residue was chromatographed on silica gel (gradient: acetone/hexanes; 5:95 to 3:7) to afford the product 1l as a clear oil.

Step I

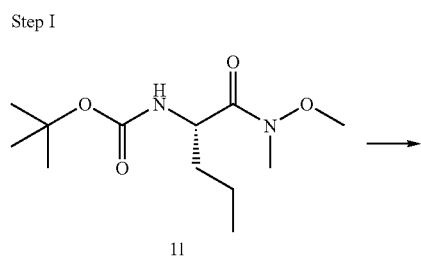

1l

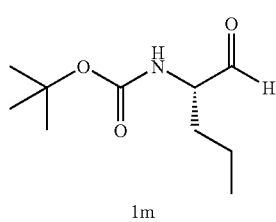

1m

A solution of amide 1l (2.2 g) in 100 mL of dry THF was cooled to ° C. Lithium aluminum hydride solution (1.3 eq) was added dropwise. The cooling bath was removed after 5 min and the mixture was allowed to reach room temperature. TLC analysis (ethyl acetate/hexanes; 2:8) showed that all the starting material had been consumed. The excess LAH was carefully quenched by addition of drops of aqueous saturated sodium hydrogen sulfate. The mixture was diluted with 200 mL of ether and aqueous saturated sodium hydrogen sulfate was added in small portions until a white solid precipitated. The mixture was filtered thru celite and the filtrate was washed with 50 mL of brine. The organic layer was dried over magnesium sulfate, filtered and concentrated. The residue was chromatographed on silica gel (gradient: ethyl acetate/hexanes; 5:95 to 4:6) to afford the aldehyde product 1m as a colorless oil.

Step J

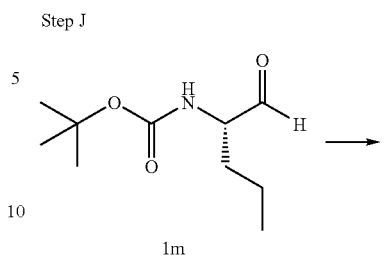

1m

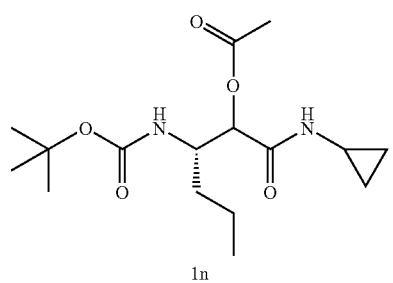

1n

A solution of aldehyde 1m (1.8 g) in 100 mL of dry dichloromethane was treated with isonitrile (1.1 eq, 680 mg) and acetic acid (2 eq, 1.02 mL, d 1.0149). The mixture was stirred overnight. All the volatiles were removed under vacuum and the residue was chromatographed on silica gel (gradient: ethyl acetate/hexanes; 2:8 to 6:4) to afford the product 1n as a white solid.

Step K

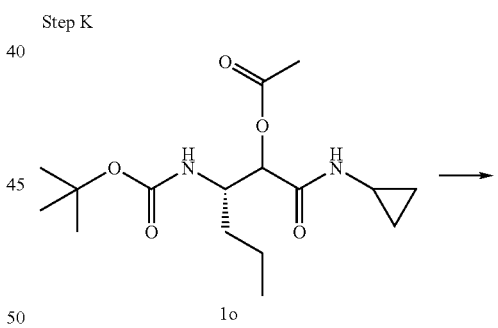

1o

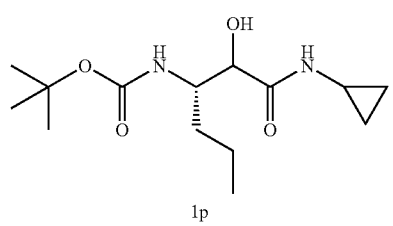

1p

A solution of acetate 1o (1.6 g) in 60 mL of a 1:1:1 mixture of THF/MeOH/water was treated with lithium hydroxide monohydrate and stirred for approximately 1 h until all the starting material had been consumed as determined by TLC analysis (ethyl acetate/hexanes; 1:1). The volatiles were removed in rotovap and the residue was diluted with dichloromethane (150 mL). The layers were separated and the aqueous layer was diluted with 30 mL of aqueous saturated sodium bicarbonate solution and extracted with dichloromethane (3×80 mL). The combined organic layers were dried over magnesium sulfate, filtered and concentrated to afford the product 1p as a white solid.

Step L

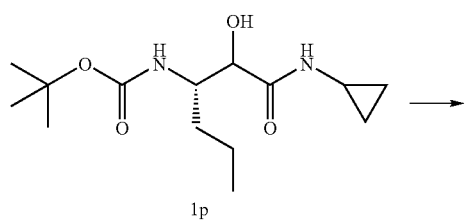

1p

-continued

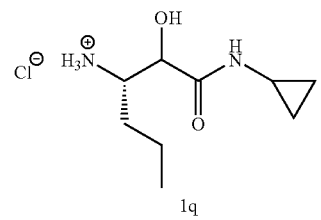

1q

The N-Boc protected amine 1p (1.5 g) was dissolved in 20 mL of 4M HCl in dioxane. The reaction mixture was stirred for about 1 h until all the starting material had been consumed. All the volatiles were removed under vacuum to afford the product 1q as a white solid.

Step M

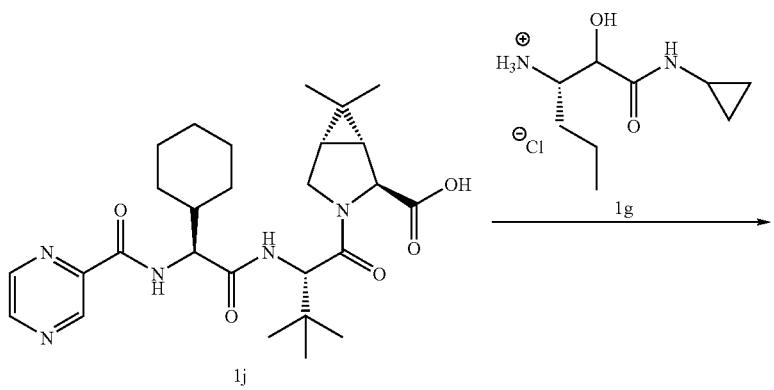

1j

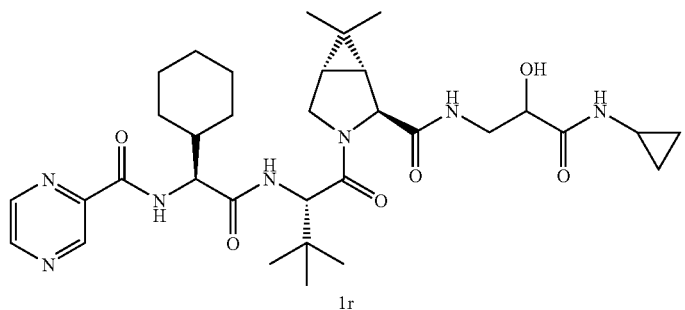

1r

A solution of acid 1j (50 mg) in 2 mL of dry dichloromethane and 2 mL of dry DMF was stirred at 0° C. and treated with HATU (1.4 eq, 52 mg). The amine hydrochloride 1q (1.2 eq, 26 mg) was added. Then, N-methylmorpholine (4 eq, 0.042 mL, d 0.920) was also added. The reaction mixture was stirred at 0° C. overnight. All the volatiles were removed under vacuum and the residue was dissolved in 80 mL of ethyl acetate. The organic layer was washed with water (10 mL), aqueous 1N HCl (10 mL), aqueous saturated sodium bicarbonate solution (10 mL), and brine (10 mL). The organic layer was dried over magnesium sulfate, filtered and concentrated under reduced pressure. The product 1r was used without further purification.

Step N

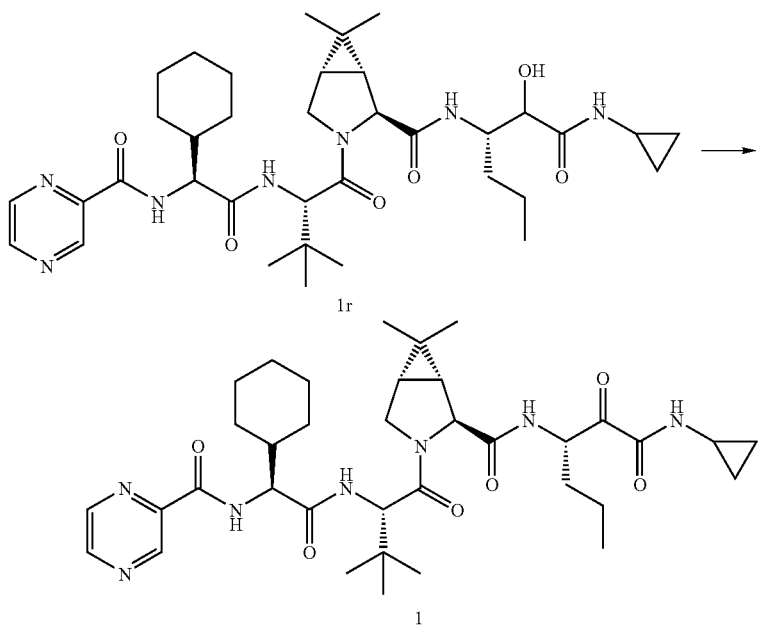

A solution of alcohol 1r (65 mg) in 5 mL of dry dichloromethane was treated with Dess-Martin periodinane (3 eq, 121 mg). Reaction mixture was stirred at room temperature for 45 min. The mixture was treated with aqueous 1M sodium thiosulfate solution (10 mL) and aqueous saturated sodium bicarbonate solution (10 mL) and stirred for 15 min. The mixture was extracted with dichloromethane (3×20 mL). The combined organic layers were dried over magnesium sulfate, filtered, and concentrated. The residue was chromatographed on silica gel (gradient: acetone/hexanes; 2:8 to 5:5) to afford the product 1 as a white solid. HRMS (FAB) calcd for $C_{36}H54N_7O_6$ [M+H] 680.4136; found 680.4131.

PREPARATIVE EXAMPLE 2

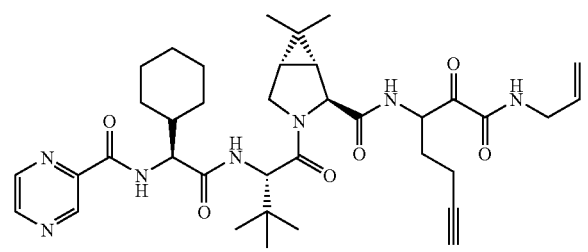

Step A

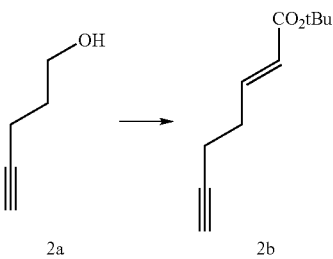

To a solution of 4-pentyn-1-ol, 2a (4.15 g; Aldrich) was added Dess-Martin periodinane (30.25 g; Aldrich) and the resulting mixture was stirred for 45 min. before the addition of (tert-Butoxycarbonylmethylene)triphenylphosphorane (26.75 g; Aldrich). The resulting dark reaction was stirred overnight, diluted with ethyl acetate), washed with aqueous sodium sulfite, saturated aqueous sodium bicarbonate, water, brine and dried. The volatiles were removed under reduced pressure and the residue was purified by silica gel column chromatography using 1% ethyl acetate in hexanes as eluent to give the desired compound 2b (3.92 g). Some impure fractions were also obtained but set aside at this time.

Step B

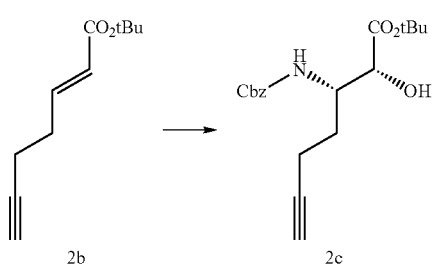

A solution of acetate 1o (1.6 g) in 60 mL of a 1:1:1 mixture of THF/MeOH/water was treated with lithium hydroxide monohydrate and stirred for approximately 1 h until all the Using the alkene 2b (1.9 g) in n-propanol (20 mL; Aldrich)), benzyl carbamate (4.95 g; Aldrich) in n-propanol (40 mL), NaOH (1.29 g) in water (79 ml), tert-butyl hypochlorite (3.7 ml), (DHQ)2PHAL (0.423 g; Aldrich)) in n-propanol (37.5 ml), and potassium osmate:dehydrate (0.1544 g; Aldrich) and the procedure set forth in *Angew. Chem. Int. Ed. Engl* (1998), 35, (23/24), pp. 2813-7 gave a crude product which was purified by silica gel column chromatography using EtOAc:Hexanes (1:5) to give the desired amino alcohol 2c (1.37 g, 37%) as a white solid.

Step C

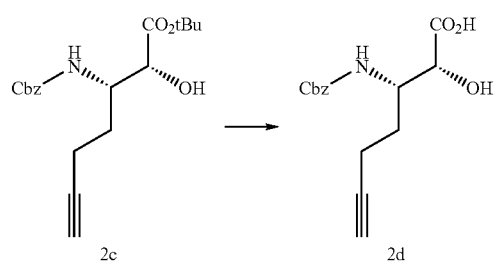

To the ester 2c (0.700 g) was added 4M HCl in dioxane (20 ml; Aldrich) and the resulting mixture was allowed to stand at room temperature overnight. The volatiles were removed under reduced pressure to give the acid 2d (0.621 g) as a white solid.

Step D

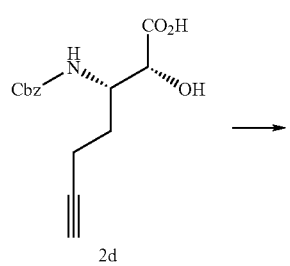

-continued

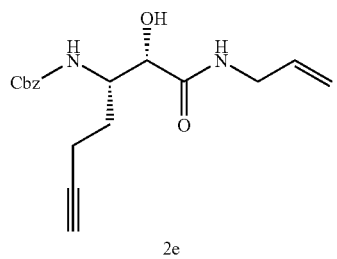

BOP reagent (3.65 g; Sigma) followed by triethylamine (3.45 ml) were added to a dichloromethane (20 ml) solution of the carboxylic acid 2d (2.00 g) and allyl amine (0.616 ml) at room temperature and the resulting mixture was stirred overnight. The reaction mixture was partitioned between EtOAc and 10% aqueous HCl. The organic phase was separated, washed with saturated aqueous sodium bicarbonate, water, dried (magnesium sulfate). The crude reaction product was purified by silica gel column chromatography using (EtOAc:Hexanes; 70:30) as eluent to provide the desired amide 2e (1.73 g) as a viscous yellow oil.

Step E

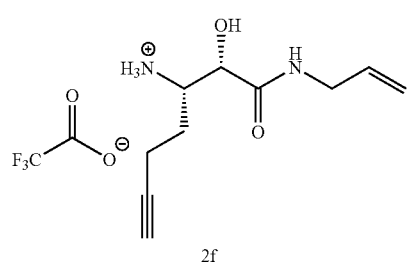

A solution of N-Cbz amine 2e (85.8 mg) in 5 mL of a 4:1 mixture of trifluoroacetic acid/methyl sulfide was stirred at room temperature for about 3h. All the volatiles were removed under reduced pressure. The product 2f was placed under high vacuum for about 3 h and used without further purification.

Step F

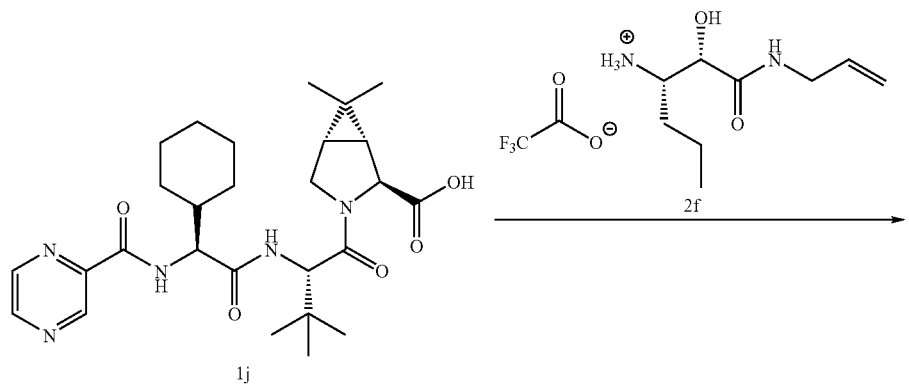

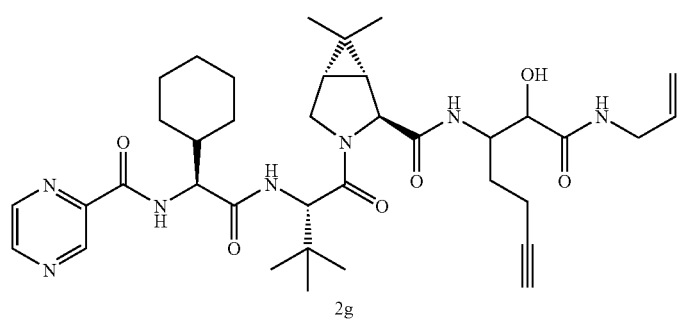

A solution of acid 1j (50 mg) in 2 mL of dry dichloromethane and 2 mL of dry DMF was stirred at 0° C. and treated with HATU (1.4 eq, 72 mg). The amine salt 2f (1.3 eq, 72 mg) was added in dichloromethane. Then, N-methylmorpholine (4 eq, 0.042 mL, d 0.920) was also added. The reaction mixture was stirred overnight (temp 0 to 25° C.). All the volatiles were removed under vacuum and the residue was dissolved in 80 mL of ethyl acetate. The organic layer was washed with water (10 mL), aqueous 1N HCl (10 mL), aqueous saturated sodium bicarbonate solution (10 mL), and brine (10 mL). The organic layer was dried over magnesium sulfate, filtered and concentrated under reduced pressure. The product 2g was used without further purification.

Step G

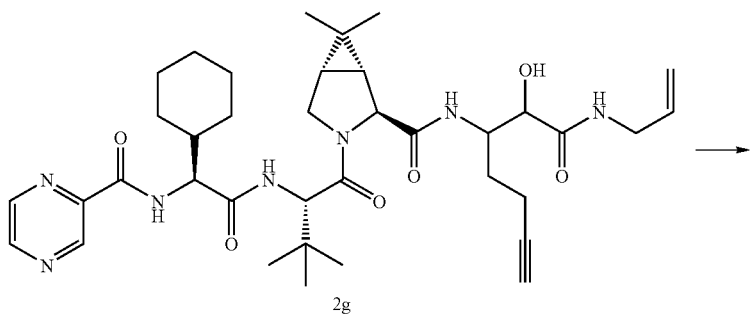

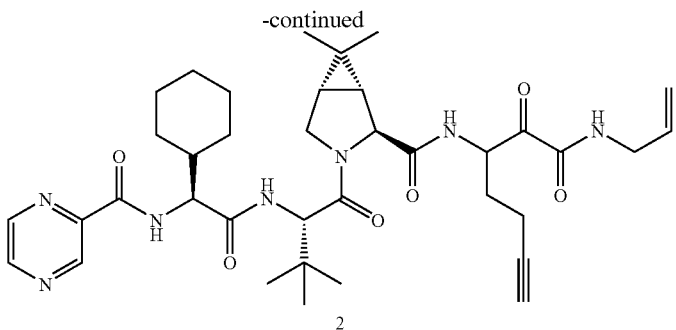

A solution of hydroxyamide 2g (67 mg) in 5 mL of dry dichloromethane was treated with Dess-Martin periodinane (3 eq, 123 mg). The reaction mixture was stirred at room temperature for 45 min. The mixture was treated with aqueous 1M sodium thiosulfate solution (10 mL) and aqueous saturated sodium bicarbonate (10 mL) and stirred for 15 min. The mixture was extracted with dichloromethane (3×20 mL). The combined organic layers were dried over magnesium sulfate, filtered, and concentrated. The residue was chromatographed on silica gel (gradient: acetone/hexanes; 2:8 to 4:6) to afford the product 2 as a white solid. HRMS (FAB) calcd for $C_{34}H_{52}N_7O_6$ [M+H] 690.3979; found 690.3995.

PREPARATIVE EXAMPLE 3

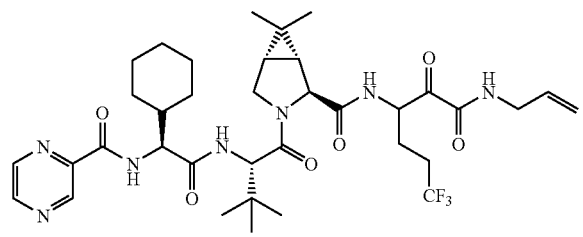

Step A

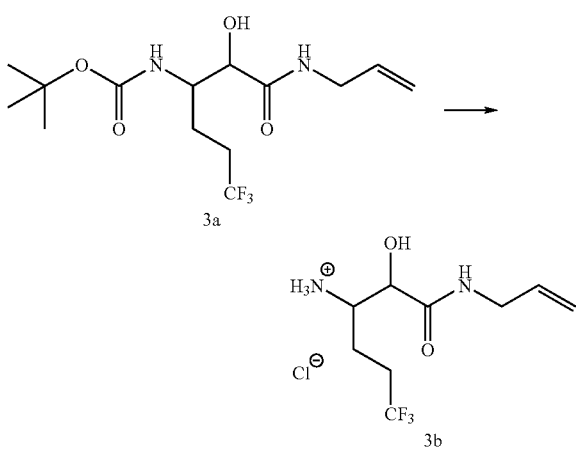

The N-Boc protected amine 3a (3 g) was dissolved in 60 mL of 4M HCl solution in dioxanes. The mixture was stirred at room temperature until all the starting material had been consumed as determined by TLC (ethyl acetate/hexanes; 6:4). After 2 h, all the volatiles were removed under reduced pressure to afford the product 3b (2.4 g, 98%) as a white solid which was used without further purification.

Step B

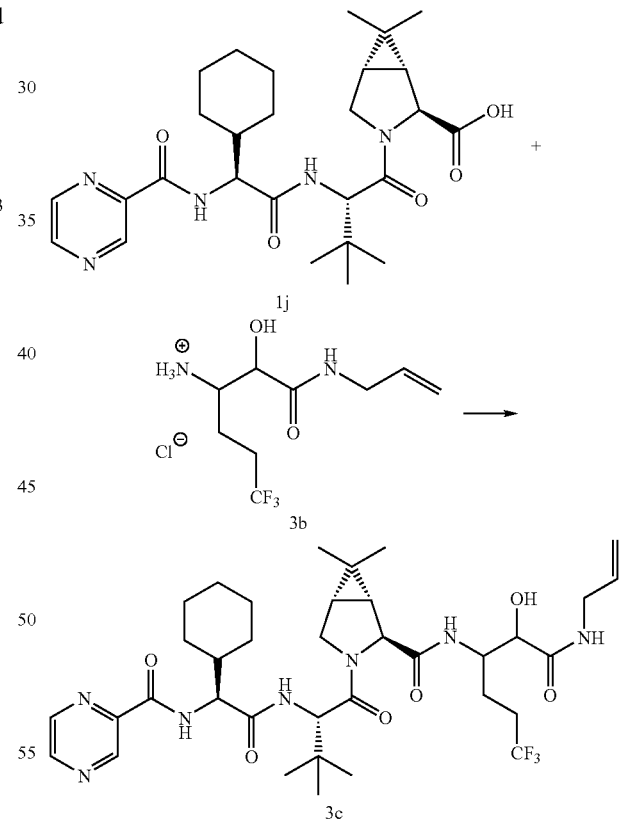

A solution of acid 1j (150 mg) in 3 mL of dry dichloromethane and 3 mL of dry DMF was stirred at 0° C. and treated with HATU (1.4 eq, 155 mg). The amine hydrochloride 3b (88 mg) was added followed by N-methylmorpholine (4 eq, 0.13 mL, d 0.920). The reaction mixture was stirred overnight (temp 0 to 25° C.). All the volatiles were removed under vacuum and the residue was dissolved in 50 mL of ethyl acetate. The organic layer was washed with water (10 mL), aqueous 1N HCl (10 mL), aqueous saturated sodium bicarbonate solution (10 mL), and brine (8 mL). The organic layer was dried over magnesium sulfate, filtered and concentrated under reduced pressure. The crude product 3c (210 mg) was used without further purification.

Step C

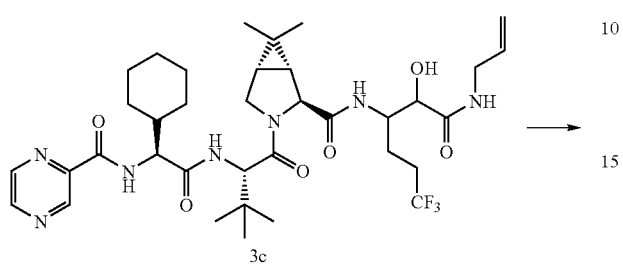

3c

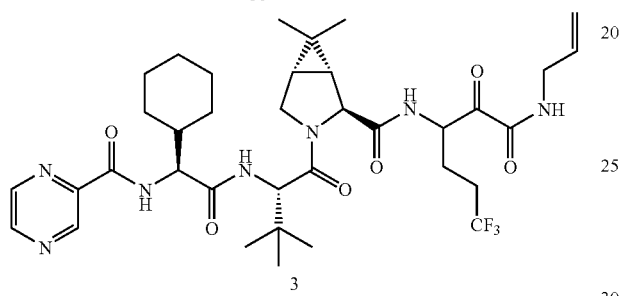

3

A solution of hydroxyamide 3c (214 mg) in 10 mL of dry dichloromethane was treated with Dess-Martin periodinane (3 eq, 371 mg). The reaction mixture was stirred at room temperature for 30 min. The mixture was treated with aqueous 1M sodium thiosulfate solution (10 mL) and stirred for 5 min. Aqueous saturated sodium bicarbonate solution (10 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 2:8 to 45:55) to afford the product 3 as a semi-solid which was dissolved in 2 mL of dichloromethane and 10 mL of hexane, the solvent was removed under reduced pressure to give the product 3 as a white solid (150 mg, 70% for two steps). HRMS (FAB) calcd for $C_{36}H_{51}F_3N_7O_6$ [M+H] 734.3853; found 734.3850.

PREPARATIVE EXAMPLE 4

4

Step A

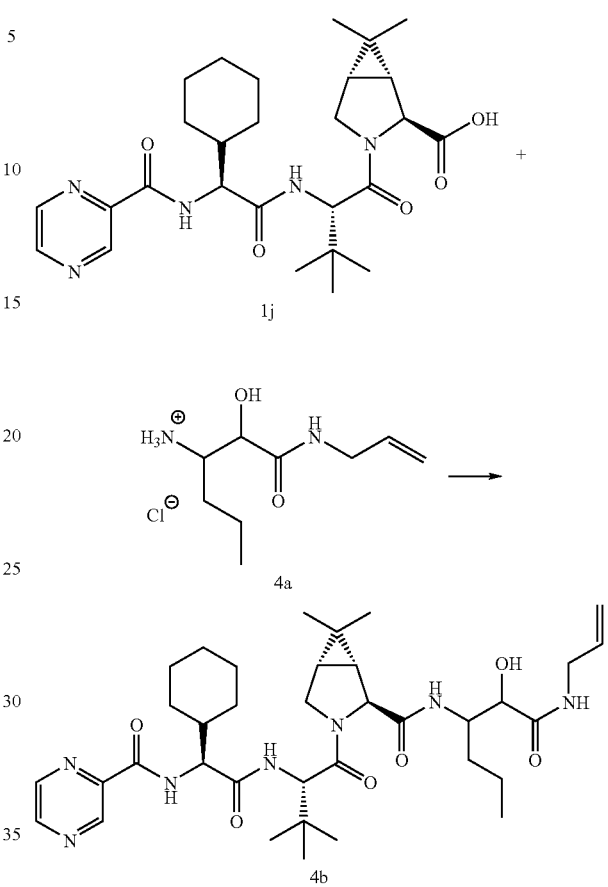

A solution of acid 1j (150 mg) in 3 mL of dry dichloromethane and 3 mL of dry DMF was stirred at 0° C. and treated with HATU (1.4 eq, 155 mg). The amine hydrochloride 4a (71 mg) was added followed by N-methylmorpholine (4 eq, 0.13 mL, d 0.920). The reaction mixture was stirred overnight (temp 0 to 25° C.). All the volatiles were removed under vacuum and the residue was dissolved in 50 mL of ethyl acetate. The organic layer was washed with water (10 mL), aqueous 1N HCl (10 mL), aqueous saturated sodium bicarbonate (10 mL), and brine (8 mL). The organic layer was dried over magnesium sulfate, filtered and concentrated under reduced pressure. The crude product 4b (190 mg) was used without further purification.

Step B

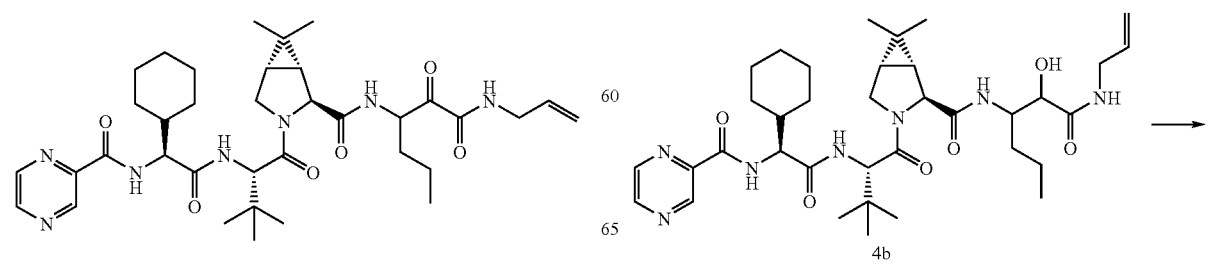

4b

-continued

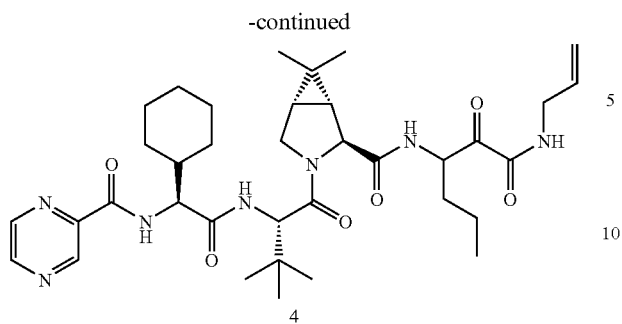

4

A solution of hydroxyamide 4b (199 mg) in 10 mL of dry dichloromethane was treated with Dess-Martin periodinane (3 eq, 371 mg). The reaction mixture was stirred at room temperature for 30 min. The mixture was treated with aqueous 1M sodium thiosulfate solution (10 mL) and stirred for 5 min. Aqueous saturated sodium bicarbonate solution (10 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 2:8 to 4:6) to afford the product 4 as a semi-solid which was dissolved in 2 mL of dichloromethane and 10 mL of hexane, the solvent was removed under reduced pressure to give the product 4 (150 mg, 76% for two steps) as a white solid. HRMS (FAB) calcd for $C_{36}H_{54}N_7O_6$ [M+H] 680.4136; found 680.4165.

PREPARATIVE EXAMPLE 5

-continued

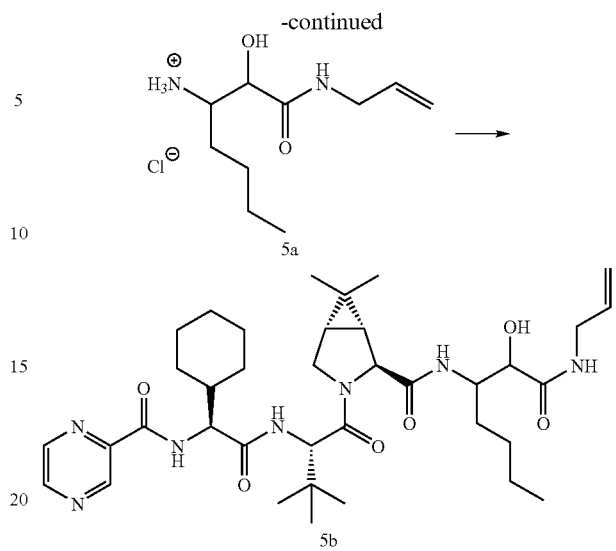

A solution of acid 1j (150 mg) in 3 mL of dry dichloromethane and 3 mL of dry DMF was stirred at 0° C. and treated with HATU (1.4 eq, 155 mg). The amine hydrochloride 5a (76 mg) was added followed by N-methylmorpholine (4 eq, 0.13 mL, d 0.920). The reaction mixture was stirred overnight (temp 0 to 25° C.). All the volatiles were removed under vacuum and the residue was dissolved in 50 mL of ethyl acetate. The organic layer was washed with water (10 mL), aqueous 1N HCl (10 mL), aqueous saturated sodium bicarbonate (10 mL), and brine (8 mL). The organic layer was dried over magnesium sulfate, filtered and concentrated under reduced pressure. The crude product 5b (200 mg) was used without further purification.

Step B

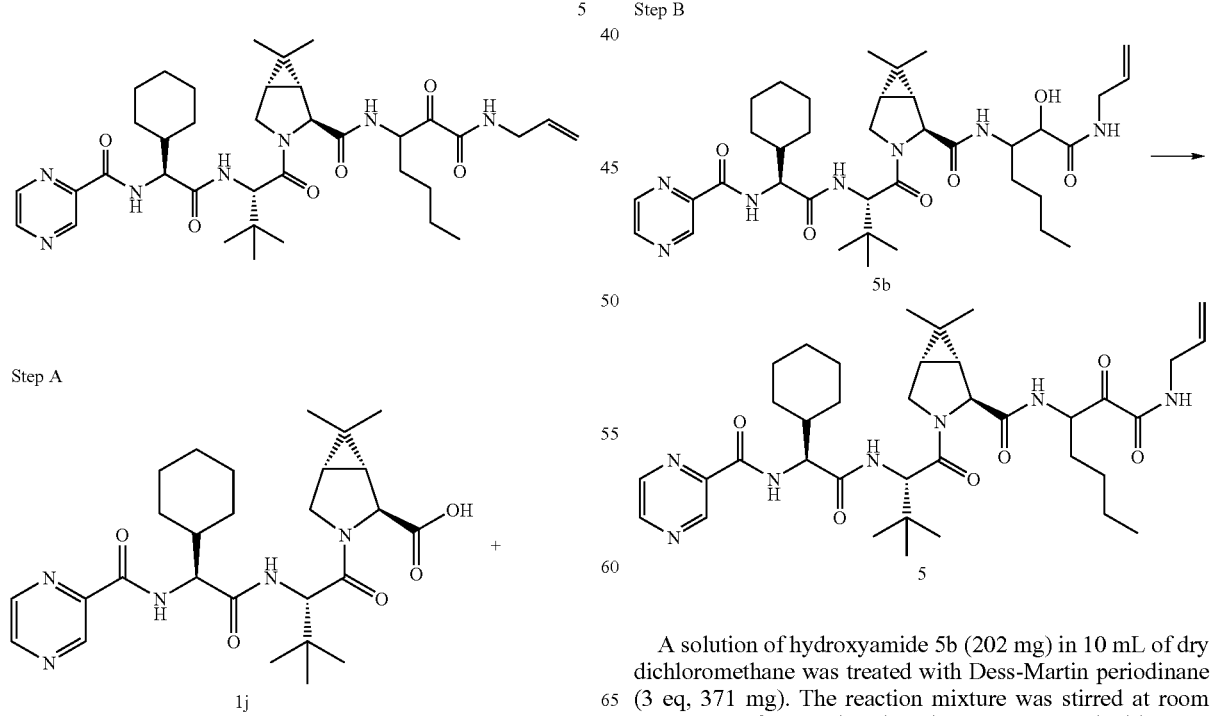

Step A

A solution of hydroxyamide 5b (202 mg) in 10 mL of dry dichloromethane was treated with Dess-Martin periodinane (3 eq, 371 mg). The reaction mixture was stirred at room temperature for 30 min. The mixture was treated with aqueous 1M sodium thiosulfate solution (10 mL) and stirred for 5 min. Aqueous saturated sodium bicarbonate solution (10 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 2:8 to 45:55) to afford the product 5 as a semi-solid which was dissolved in 2 mL of dichloromethane and 10 mL of hexane, the solvent was removed under reduced pressure to give the product 5 (170 mg, 84% for two steps) as a white solid. HRMS (FAB) calcd for $C_{37}H_{56}N_7O_6$ [M+H] 694.4292; found 694.4294.

PREPARATIVE EXAMPLE 6

6

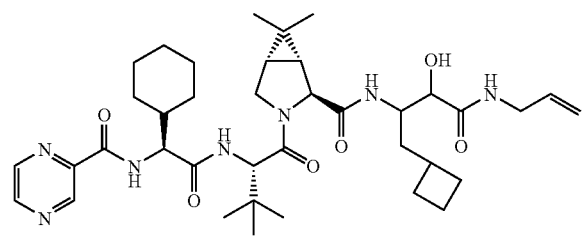

Step A

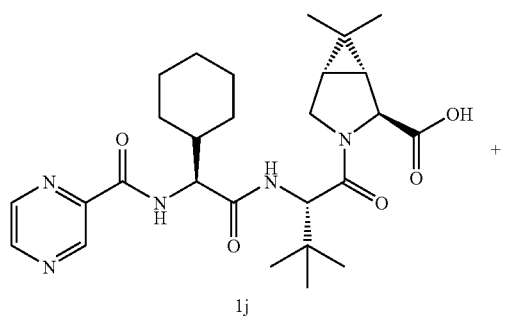

1j

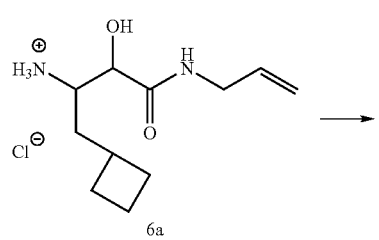

6a

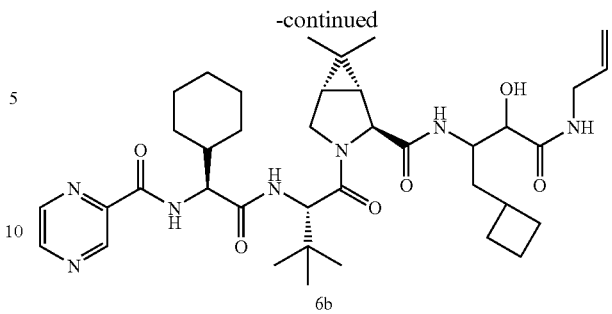

6b

A solution of acid 1j (150 mg) in 3 mL of dry dichloromethane and 3 mL of dry DMF was stirred at 0° C. and treated with HATU (1.4 eq, 155 mg). The amine hydrochloride 6a (80 mg) was added followed by N-methylmorpholine (4 eq, 0.13 mL, d 0.920). The reaction mixture was stirred overnight (temp 0 to 25° C.). All the volatiles were removed under vacuum and the residue was dissolved in 50 mL of ethyl acetate. The organic layer was washed with water (10 mL), aqueous 1N HCl (10 mL), aqueous saturated sodium bicarbonate (10 mL), and brine (8 mL). The organic layer was dried over magnesium sulfate, filtered and concentrated under reduced pressure. The crude product 6b (205 mg) was used without further purification.

Step B

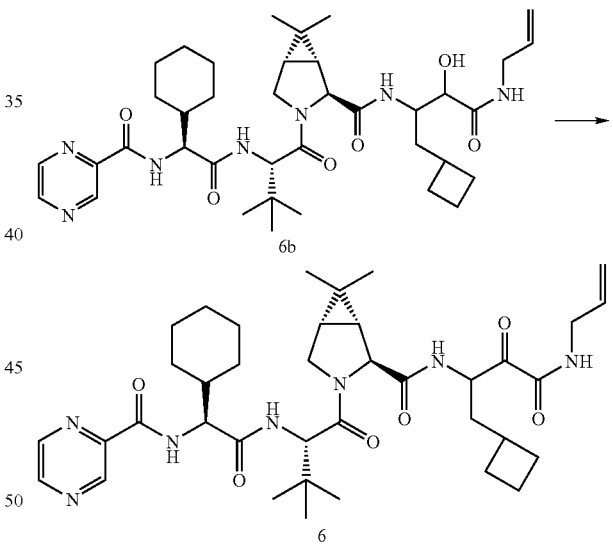

6b

6

A solution of hydroxyamide 6b (206 mg) in 10 mL of dry dichloromethane was treated with Dess-Martin periodinane (3 eq, 371 mg). The reaction mixture was stirred at room temperature for 30 min. The mixture was treated with aqueous 1M sodium thiosulfate solution (10 mL) and stirred for 5 min. Aqueous saturated sodium bicarbonate (10 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 2:8 to 45:55) to afford the product 6 as a semi-solid which was dissolved in 2 mL of dichloromethane and 10 mL of hexane, the solvent was removed under reduced pressure to give the product 6 (169 mg, 82% for two steps) as a white solid. HRMS (FAB) calcd for $C_{38}H_{56}N_7O_6$ [M+H] 706.4292; found 706.4280.

PREPARATIVE EXAMPLE 7

7

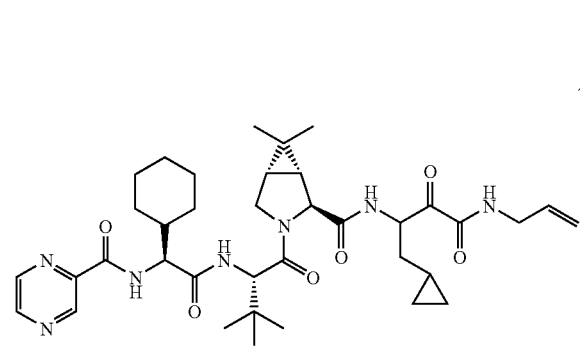

Step A

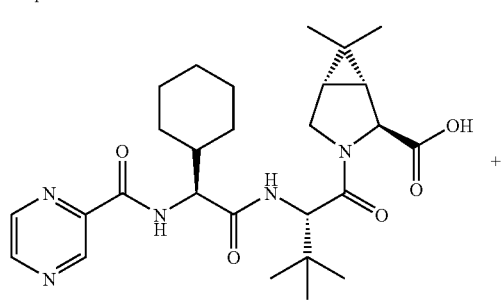

1j

+

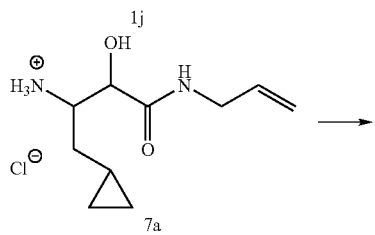

7a

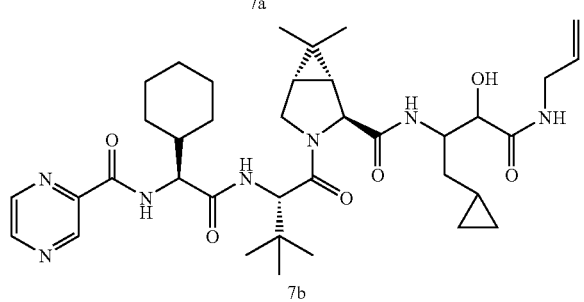

7b

A solution of acid 1j (80 mg) in 3 mL of dry dichloromethane and 3 mL of dry DMF was stirred at 0° C. and treated with HATU (1.4 eq, 83 mg). The amine hydrochloride 7a (1.1 eq, 40 mg) was added followed by N-methylmorpholine (4 eq, 0.07 mL, d 0.920). The reaction mixture was stirred overnight (temp 0 to 25° C.). All the volatiles were removed under vacuum and the residue was dissolved in 50 mL of ethyl acetate. The organic layer was washed with water (10 mL), aqueous 1N HCl (10 mL), aqueous saturated sodium bicarbonate solution (10 mL), and brine (8 mL). The organic layer was dried over magnesium sulfate, filtered and concentrated under reduced pressure. The crude product 7b (105 mg) was used without further purification.

Step B

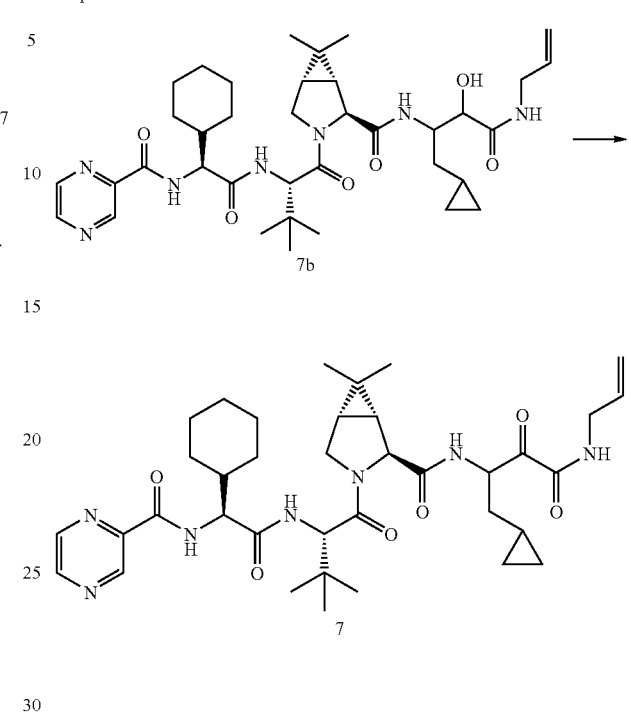

7b

7

A solution of hydroxyamide 7b (108 mg) in 10 mL of dry dichloromethane was treated with Dess-Martin periodinane (3 eq, 198 mg). The reaction mixture was stirred at room temperature for 30 min. The mixture was treated with aqueous 1M sodium thiosulfate solution (10 mL) and stirred for 5 min. Aqueous saturated sodium bicarbonate (10 mL) was added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 2:8 to 45:55) to afford the product 7 as a semi-solid which was dissolved in 2 mL of dichloromethane and 10 mL of hexane. The solvent was removed under reduced pressure to give the product 7 (86 mg, 80% for two steps) as a white solid. HRMS (FAB) calcd for $C_{37}H_{54}N_7O_6$ [M+H] 692.4136; found 692.4145.

PREPARATIVE EXAMPLE 8

8

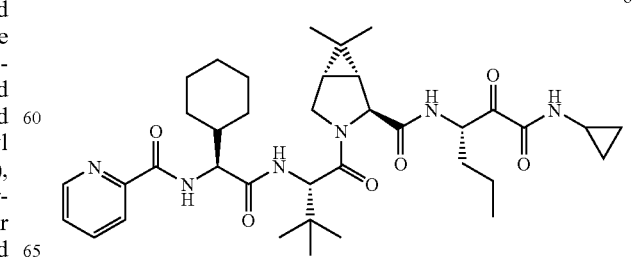

Step A

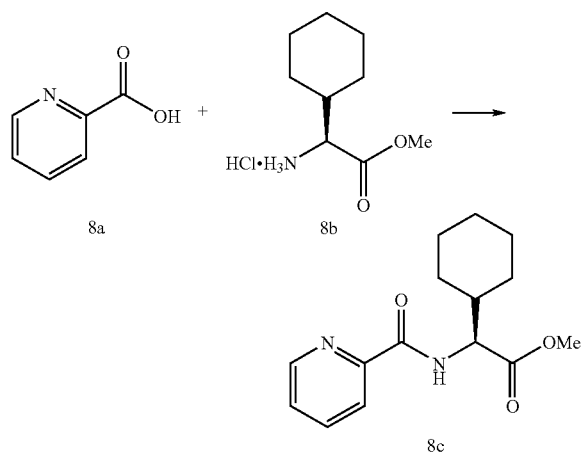

A solution of picolinic acid 8a (1.0 g) in 50 mL of dry DMF and 50 mL of dry dichloromethane was stirred at 0° C. and treated with HATU (1.4 eq, 4.3 g). Cyclohexylglycine methyl ester hydrochloride (1.1 eq, 1.85 g) was added followed by N-methylmorpholine (4 eq, 3.6 mL, d 0.920). The reaction mixture was stirred overnight (temp 0 to 25° C.). All the volatiles were removed under vacuum and the residue was dissolved in 500 mL of ethyl acetate. The organic layer was washed with water (100 mL), aqueous 1N HCl (100 mL), aqueous saturated sodium bicarbonate solution (100 mL), and brine (100 mL). The organic layer was dried over magnesium sulfate, filtered and concentrated under reduced pressure. The residue was chromatographed on silica gel (gradient: acetone/hexanes; 5:95 to 35:65) to afford the product 8c (1.9 g, 85%) as a clear semi-solid.

Step B

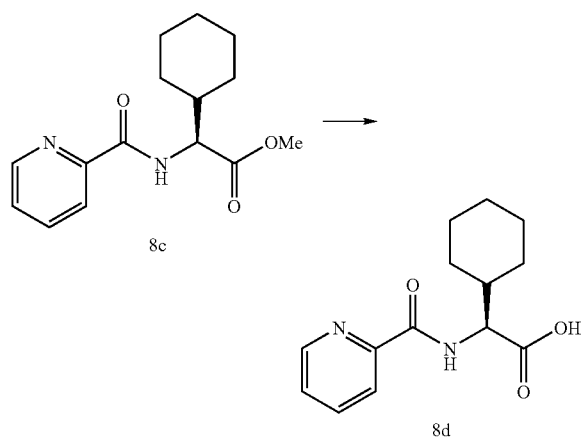

A solution of methyl ester 8c (1.9 g) in THF/MeOH/H2O (100:100:50) was treated with lithium hydroxide monohydrate (2.5 eq, 2.82 g) at 0° C. The reaction mixture was stirred until all the starting material had been consumed as determined by TLC analysis (acetone/hexanes; 15:85). The reaction mixture was treated with 100 mL of aqueous 1N HCl (pH of the mixture became approximately 1) and all the volatiles were removed under reduced pressure. The residue was extracted with dichloromethane (3×100 mL). The combined organic extracts were dried over sodium sulfate, filtered and concentrated. The crude product 8d (1.6 g, 90%) was used without further purification.

Step C

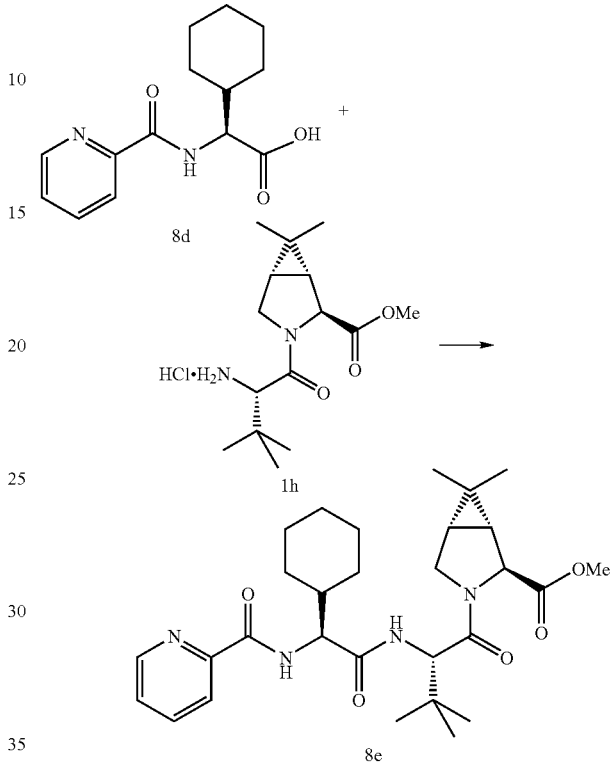

A solution of acid 8d (235 mg) in 10 mL of dry DMF and 10 mL of dichloromethane was stirred at 0° C. and treated with HATU (1.4 eq, 480 mg). The amine salt 1h (1.1 eq, 300 mg) was added followed by N-methylmorpholine (4 eq, 0.4 mL, d 0.920). The reaction mixture was stirred overnight (temp 0 to 25° C.). All the volatiles were removed under vacuum and the residue was dissolved in 100 mL of ethyl acetate. The organic layer was washed with water (20 mL), aqueous 1N HCl (20 mL), aqueous saturated sodium bicarbonate solution (10 mL), and brine (10 mL). The organic layer was dried over magnesium sulfate, filtered and concentrated under reduced pressure. The residue was chromatographed on silica gel (gradient: acetone/hexanes; 5:95 to 4:6) to afford the product 8e (440 mg, 93%).

Step D

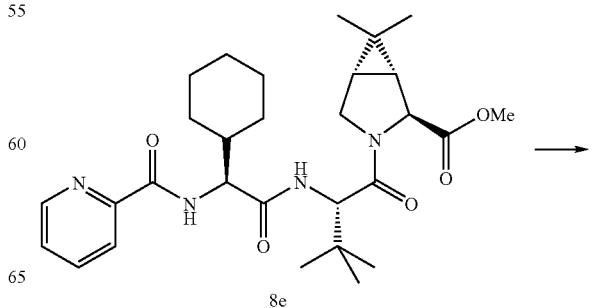

-continued

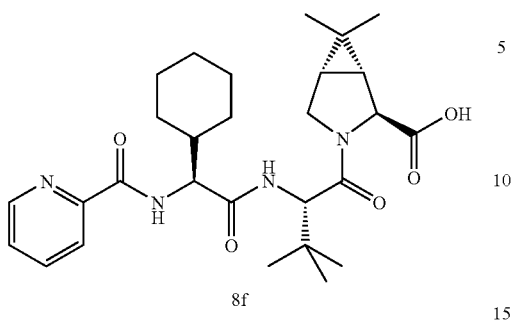

8f

-continued

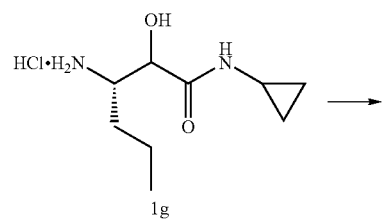

1g

A solution of methyl ester 8e (440 mg) in 30 mL of a THF/MeOH/H2O mixture (1:1:1) was treated with lithium hydroxide monohydrate (2.5 eq, 88 mg) at 0° C. The reaction mixture was stirred until all the starting material had been consumed as determined by TLC (acetone/hexanes; 3:7). The reaction mixture was treated with 20 mL of 1N aqueous HCl (pH of the mixture became approximately 1) and all the volatiles were removed under reduced pressure. The residue was extracted with dichloromethane (3×60 mL). The combined organic extracts were dried over magnesium sulfate, filtered and concentrated. The crude product 8f (419 mg, 98%) was used without further purification.

Step E

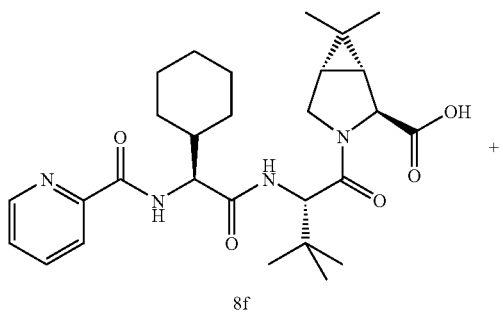

8f

+

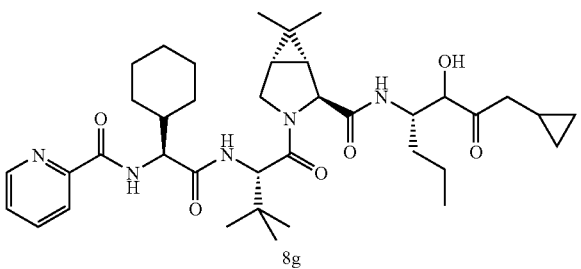

8g

A solution of acid 8f (80 mg) in 2 mL of dry dichloromethane and 1 mL of dry DMF was stirred at 0° C. and treated with HATU (1.4 eq, 83 mg). The amine salt 1g (1.1 eq, 38 mg) was added followed by N-methylmorpholine (4 eq, 0.07 mL, d 0.920). The reaction mixture was stirred overnight (temp 0 to 25° C.). All the volatiles were removed under vacuum and the residue was dissolved in 50 mL of ethyl acetate. The organic layer was washed with water (20 mL), aqueous 1N HCl (10 mL), aqueous saturated sodium bicarbonate solution (10 mL), and brine (10 mL). The organic layer was dried over magnesium sulfate, filtered and concentrated under reduced pressure. The crude product 8g (105 mg) was used without further purification.

Step F

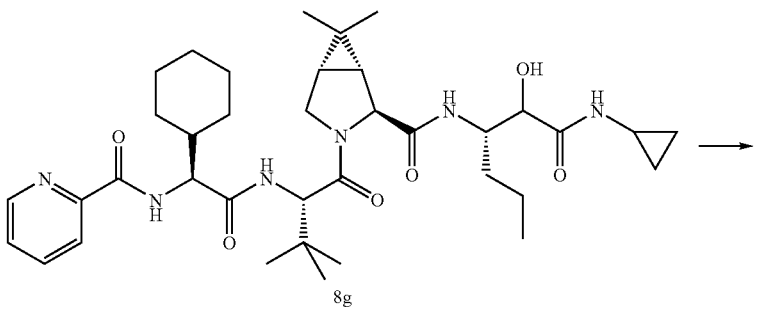

8g

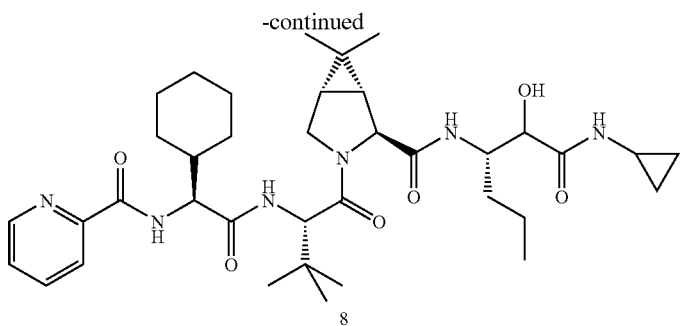

A solution of hydroxyamide 8g (0.156 mmol) in 10 mL of dry dichloromethane was treated with Dess-Martin periodinane (2.3 eq, 152 mg). The reaction mixture was stirred at room temperature for 30 min. The mixture was treated with aqueous 1M sodium thiosulfate solution (10 mL) and stirred for 5 min. Aqueous saturated sodium bicarbonate solution (10 mL) was added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 1:9 to 45:55) to afford the product 8 as a solid which was dissolved in 0.5 mL of dichloromethane and 5 mL of hexane, the solvent was removed under reduced pressure to give the product 8 (59 mg, 56% for two steps) as a white solid. HRMS (FAB) calcd for $C_{37}H_{55}N_6O_6$ [M+H] 679.4183; found 679.4191.

PREPARATIVE EXAMPLE 9

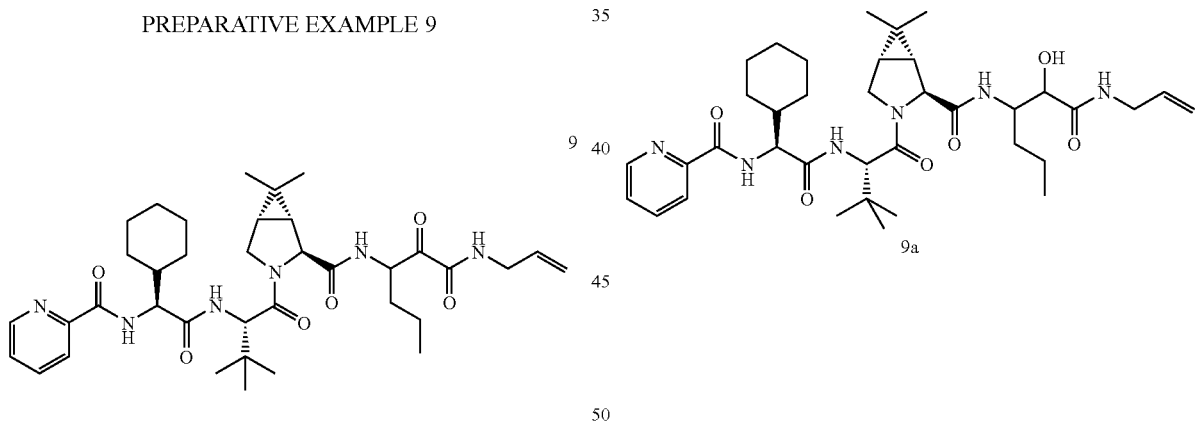

Step A

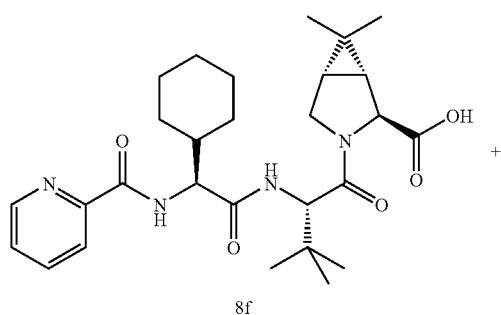

A solution of acid 8f (80 mg) in 2 mL of dry dichloromethane and 1 mL of dry DMF was stirred at 0° C. and treated with HATU (1.4 eq, 83 mg). The amine salt 4a (1.1 eq, 38 mg) was added followed by N-methylmorpholine (4 eq, 0.07 mL, d 0.920). The reaction mixture was stirred overnight (temp 0 to 25° C.). All the volatiles were removed under-vacuum and the residue was dissolved in 50 mL of ethyl acetate. The organic layer was washed with water (20 mL), aqueous 1N HCl (10 mL), aqueous saturated sodium bicarbonate solution (10 mL), and brine (10 mL). The organic layer was dried over magnesium sulfate, filtered and concentrated under reduced pressure. The crude product 9a (105 mg) was used without further purification.

Step B

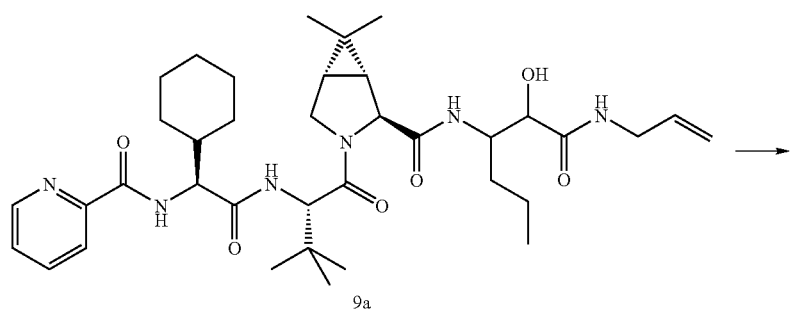
9a

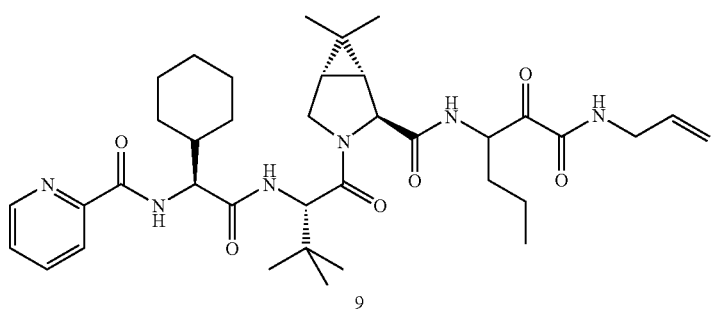
9

A solution of hydroxyamide 9a (0.156 mmol) in 10 mL of dry dichloromethane was treated with Dess-Martin periodinane (2.3 eq, 152 mg). The reaction mixture was stirred at room temperature for 30 min. The mixture was treated with aqueous 1M sodium thiosulfate solution (10 mL) and stirred for 5 min. Aqueous saturated sodium bicarbonate solution (10 mL) was added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 1:9 to 4:6) to afford the product 9 as a solid which was dissolved in 0.5 mL of dichloromethane and 5 mL of hexane, the solvent was removed under reduced pressure to give the product 9 (68 mg, 64% for two steps) as a white solid. HRMS (FAB) calcd for $C_{37}H_{55}N_6O_6$ [M+H]; 679.4183 found 679.4181.

PREPARATIVE EXAMPLE 10

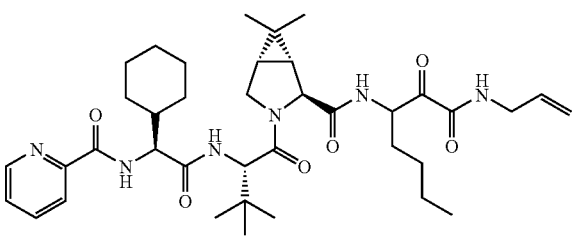
10

Step A

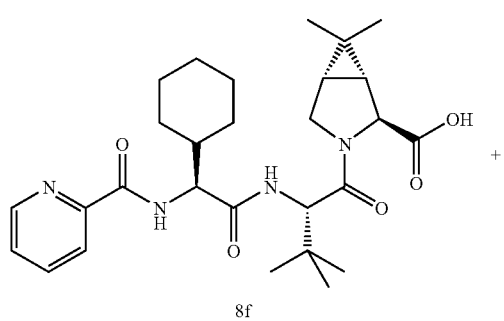

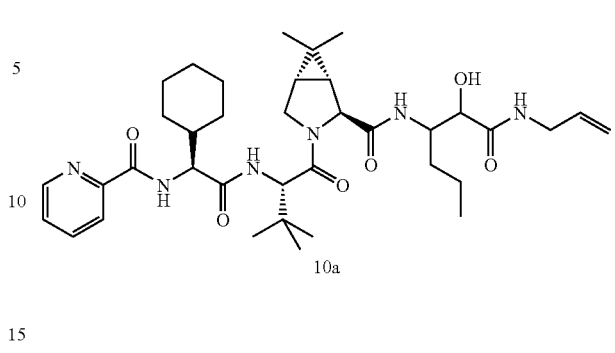

A solution of acid 8f (80 mg) in 2 mL of dry dichloromethane and 1 mL of dry DMF was stirred at 0° C. and treated with HATU (1.4 eq, 83 mg). The amine salt 5a (1.1 eq, 41 mg) was added followed by N-methylmorpholine (4 eq, 0.07 mL, d 0.920). The reaction mixture was stirred overnight (temp 0 to 25° C.). All the volatiles were removed under vacuum and the residue was dissolved in 50 mL of ethyl acetate. The organic layer was washed with water (20 mL), aqueous 1N HCl (10 mL), aqueous saturated sodium bicarbonate solution (10 mL), and brine (10 mL). The organic layer was dried over magnesium sulfate, filtered and concentrated under reduced pressure. The crude product 10a (105 mg) was used without further purification.

Step B

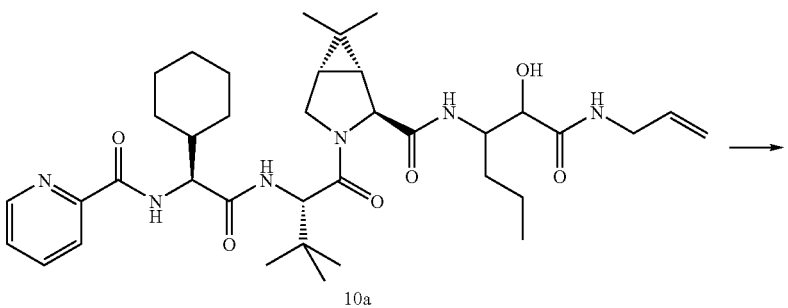

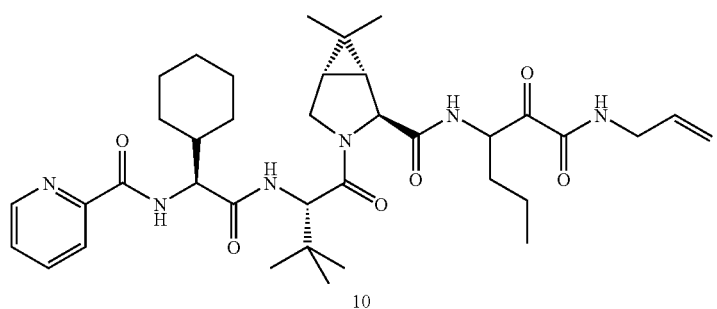

A solution of hydroxyamide 10a (0.156 mmol) in 10 mL of dry dichloromethane was treated with Dess-Martin periodinane (2.3 eq, 152 mg). The reaction mixture was stirred at room temperature for 30 min. The mixture was treated with aqueous 1M sodium thiosulfate solution (10 mL) and stirred for 5 min. Aqueous saturated sodium bicarbonate (10 mL) was added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 1:9 to 4:6) to afford the product 10 as a solid which was dissolved in 0.5 mL of dichloromethane and 5 mL of hexane, the solvent was removed under reduced pressure to give the product 10 (68 mg, 63% for two steps) as a white solid. HRMS (FAB) calcd for $C_{38}H_{57}N_6O_6$ [M+H] 693.4340; found 693.4310.

PREPARATIVE EXAMPLE 11

11

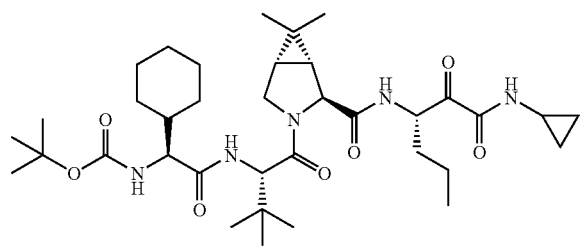

Step A

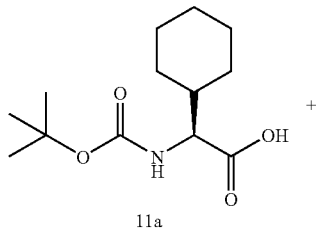

11a

-continued

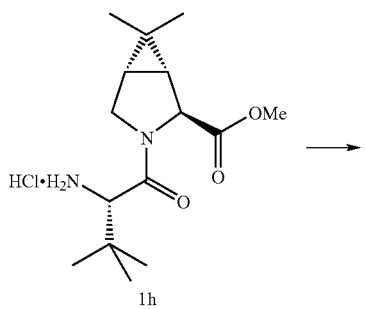

1h

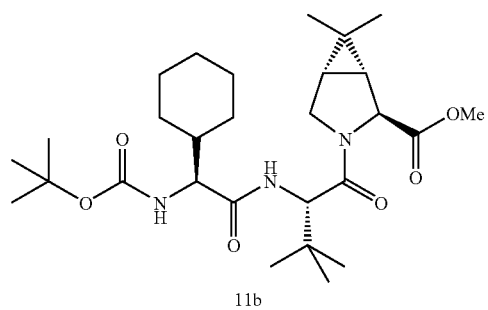

11b

A solution of N-Boc-cHex-Glycine 11a (916 mg) in 20 mL of dry DMF was stirred at 0° C. and treated with HATU (1.4 eq, 1.89 g). The amine salt 1h (1.1 eq, 1.2 g) was added in 30 mL of dry dichloromethane followed by N-methylmorpholine (4 eq, 1.55 mL, d 0.920). The reaction mixture was stirred overnight (temp 0 to 25° C.). All the volatiles were removed under vacuum and the residue was dissolved in 250 mL of ethyl acetate. The organic layer was washed with water (100 mL), aqueous 1N HCl (50 mL), aqueous saturated sodium bicarbonate solution (50 mL), and brine (50 mL). The organic layer was dried over magnesium sulfate, filtered and concentrated under reduced pressure. The residue was chromatographed on silica gel (gradient: acetone/hexanes; 5:95 to 25:75) to afford the product 11b (1.65 g, 89%) as a white solid.

Step B

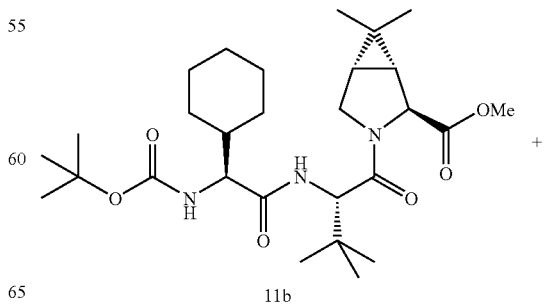

11b

-continued

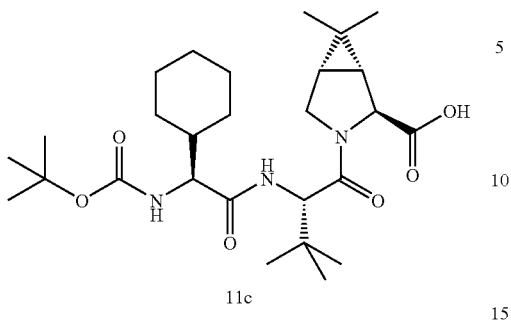

11c

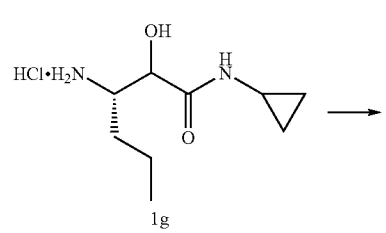

1g

A solution of methyl ester 11b (1.64 mg) in 60 mL a THF/MeOH/H2O mixture (1:1:1) was treated with lithium hydroxide monohydrate (2.5 eq, 330 mg) at 0° C. The cooling bath was removed and the reaction mixture was stirred until all the starting material had been consumed as determined by TLC (acetone/hexanes; 3:7). The reaction mixture was treated with 50 mL of 1N aqueous HCl (pH of the mixture became approx 1) and all the volatiles were removed under reduced pressure. The residue was extracted with dichloromethane (3×100 mL). The combined organic extracts were dried over magnesium sulfate, filtered and concentrated. The product 11c was obtained as a white solid (1.61 g, 98%) and used without further purification.

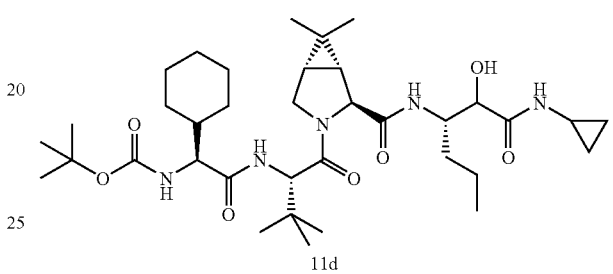

11d

Step C

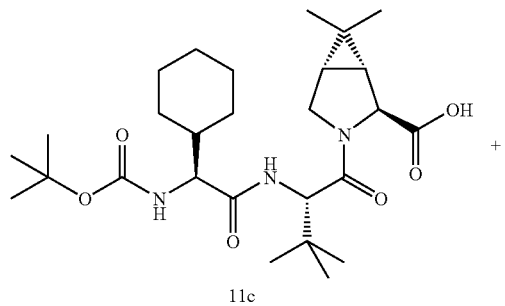

11c

A solution of acid 11c (248 mg) in 10 mL of dry dichloromethane and 5 mL of dry DMF was stirred at 0° C. and treated with HATU (1.4 eq, 120 mg). The amine salt 1g (1.1 eq, 120 mg) was added followed by N-methylmorpholine (4 eq, 0.22 mL, d 0.920). The reaction mixture was stirred overnight (temp 0 to 25° C.). All the volatiles were removed under vacuum and the residue was dissolved in 150 mL of ethyl acetate. The organic layer was washed with water (40 mL), aqueous 1N HCl (20 mL), aqueous saturated sodium bicarbonate solution (20 mL), and brine (20 mL). The organic layer was dried over magnesium sulfate, filtered and concentrated under reduced pressure. The crude product 11d (330 mg) was used without further purification.

Step D

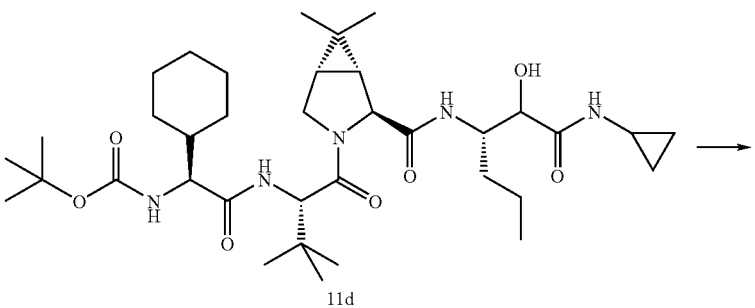

11d

-continued

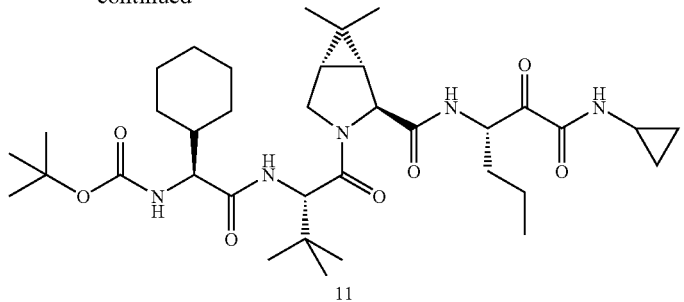

11

A solution of hydroxyamide 11d (0.489 mmol) in 20 mL of dry dichloromethane was treated with Dess-Martin periodinane (2.3 eq, 152 mg). The reaction mixture was stirred at room temperature for 30 min. The mixture was treated with aqueous 1M sodium thiosulfate solution (10 mL) and stirred for 5 min. Aqueous saturated sodium bicarbonate solution (10 mL) was added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 1:9 to 4:6) to afford the product 11e as a solid which was dissolved in 1 mL of dichloromethane and 8 mL of hexane, the solvent was removed under reduced pressure to give the product 11e (280 mg, 85% for two steps) as a white solid. HRMS (FAB) calcd for $C_{36}H_{60}N_5O_7$ [M+H] 674.4492; found 674.4507.

PREPARATIVE EXAMPLE 12

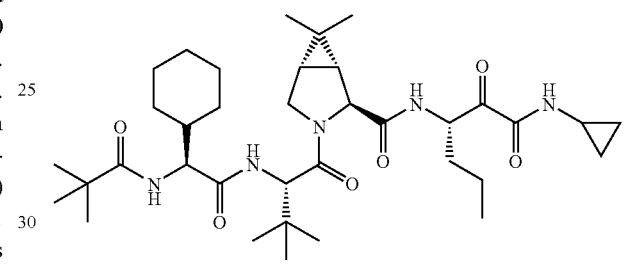

12

Step A

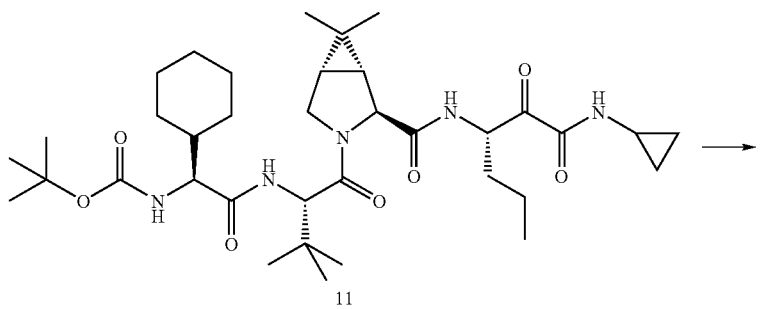

11

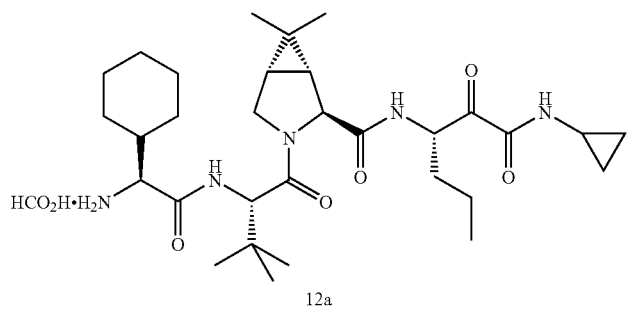

12a

The N-Boc protected amine 11 (80 mg) was dissolved in 5 mL of formic acid. The resulting solution was stirred at room temperature until all the starting material had been consumed as determined by TLC (acetone/hexanes; 3:7). After 4 h, the volatiles were removed under reduced pressure and the residue was placed under high vacuum. No further purification was done for the product 12a (70 mg, 98%).

Step B

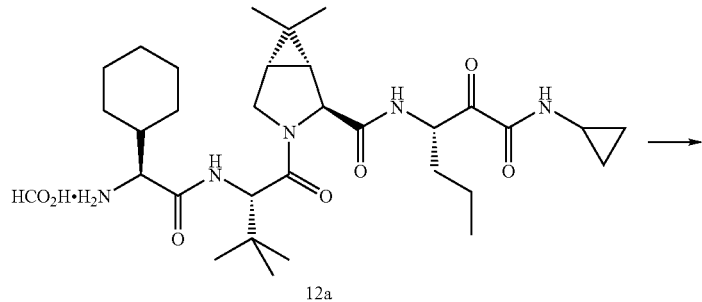

12a

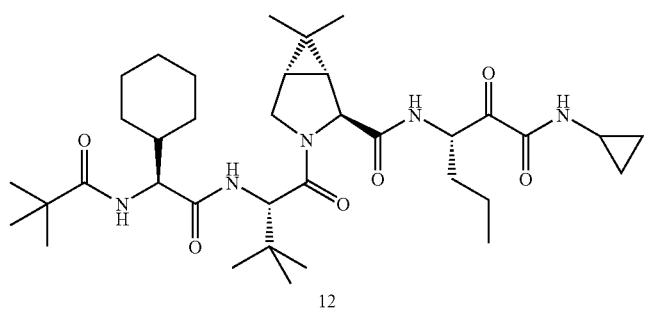

12

The amine salt 12a (0.118 mmol) was dissolved in 5 mL of dry dichloromethane and cooled to 0° C. N-methylmorpholine (2.5 eq, 0.032 mL, d 0.920) was added followed by pivalic anhydride (1.2 eq, 0.028 mL, d 0.910) in 2 mL of dry dichloromethane. The mixture was stirred overnight (temp 0 to 25° C.). The reaction mixture was diluted with 50 mL of dichloromethane. The solution was washed with 10 mL of aqueous 1M HCl, 10 mL of aqueous saturated sodium bicarbonate solution, and 10 mL of brine. The organic layer was dried over magnesium sulfate, filtered and concentrated under reduced pressure. The residue was chromatographed on silica gel (gradient: acetone/hexanes; 1:9 to 1:1) to afford the product 12 (28 mg, 36%) as a white solid. HRMS (FAB) calcd for $C_{36}H_{60}N_5O_6$ [M+H] 658.4543; found 658.4558.

PREPARATIVE EXAMPLE 13

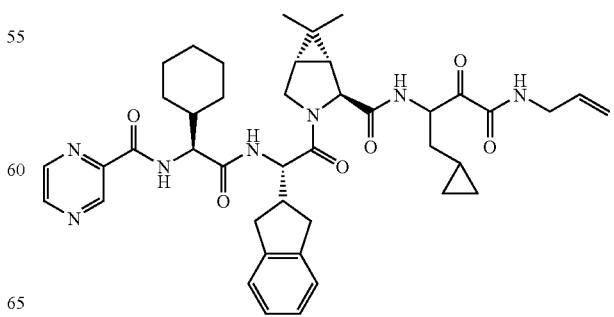

13

Step A

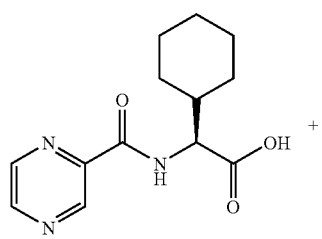

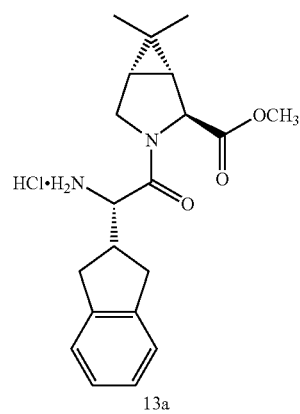

13a

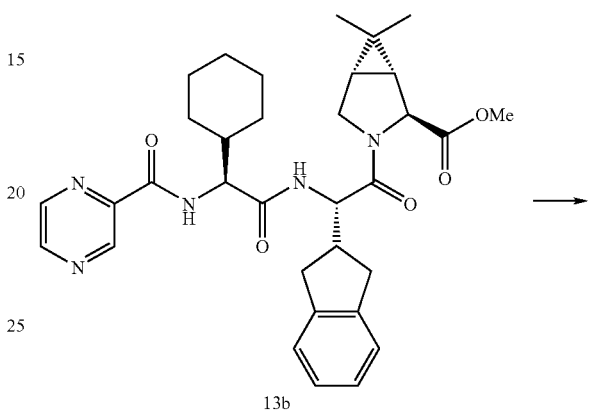

13b

Step B

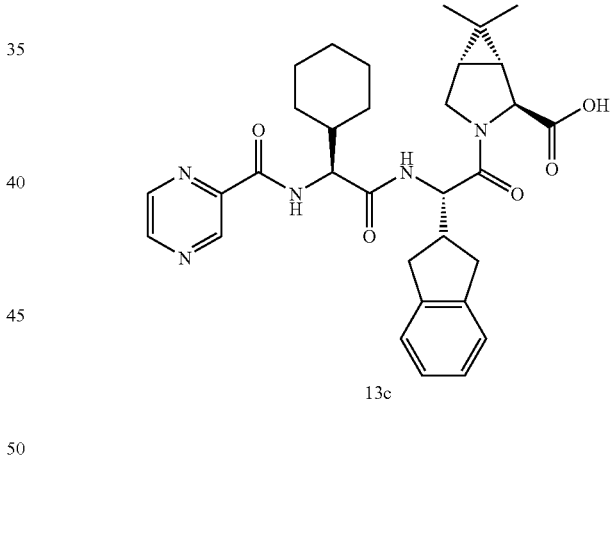

13c

A solution of acid 1d (90 mg) in 5 mL of dry dichloromethane and 3 mL of dry DMF was stirred at 0° C. and treated with HATU (1.4 eq, 180 mg). The amine hydrochloride 13a (1.0 eq, 128 mg) was added followed by N-methylmorpholine (4 eq, 0.15 mL, d 0.920). The reaction mixture was stirred overnight (temp 0 to 25° C.). All the volatiles were removed under vacuum and the residue was dissolved in 80 mL of ethyl acetate. The organic layer was washed with water (20 mL), aqueous 1N HCl (15 mL), aqueous saturated sodium bicarbonate solution (15 mL), and brine (15 mL). The organic layer was dried over magnesium sulfate, filtered and concentrated under reduced pressure. The residue was chromatographed on silica gel (gradient: acetone/hexanes; 1:9 to 4:6) to give the product 13b (160 mg, 80%) as a white solid.

The methyl ester 13b (160 mg) was dissolved in 15 mL of a 1:1:1 mixture of THF/methanol/water and treated with lithium hydroxide monohydrate (2.5 eq, 28 mg) at 0° C. The reaction mixture was gradually warmed up to room temperature and stirred for 2 h until all the starting material had been consumed. Aqueous 1M HCl (30 mL) was added and all the volatiles were removed in rotovap. The residue was extracted with dichloromethane (3×30 mL). The combined organic extracts were dried over magnesium sulfate, filtered and concentrated. The crude product 13c (150 mg, 98%) was used without further purification.

Step C

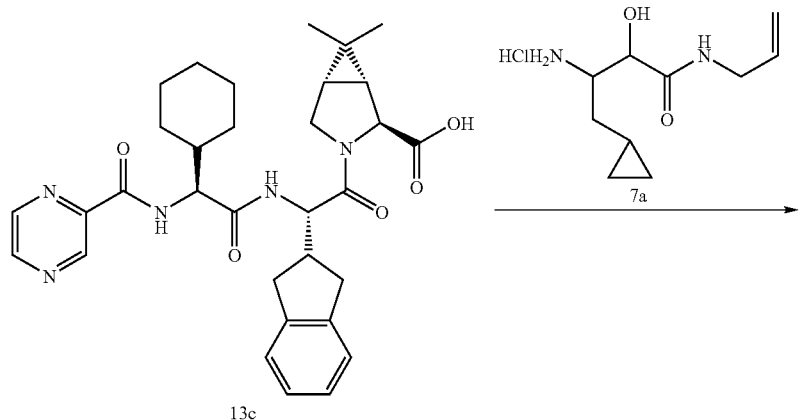

A solution of acid 13c (75 mg) in 4 mL of dry dichloromethane and 2 mL of dry DMF was stirred at 0° C. and treated with HATU (1.4 eq, 69 mg). The amine hydrochloride 7a (1.2 eq, 37 mg) was added followed by N-methylmorpholine (4 eq, 0.06 mL, d 0.920). The reaction mixture was stirred overnight (temp 0 to 25° C.). All the volatiles were removed under vacuum and the residue was dissolved in 50 mL of ethyl acetate. The organic layer was washed with water (20 mL), aqueous 1N HCl (10 mL), aqueous saturated sodium bicarbonate solution (10 mL), and brine (10 mL). The organic layer was dried over magnesium sulfate, filtered and concentrated under reduced pressure. The crude product 13d was used without further purification.

Step D

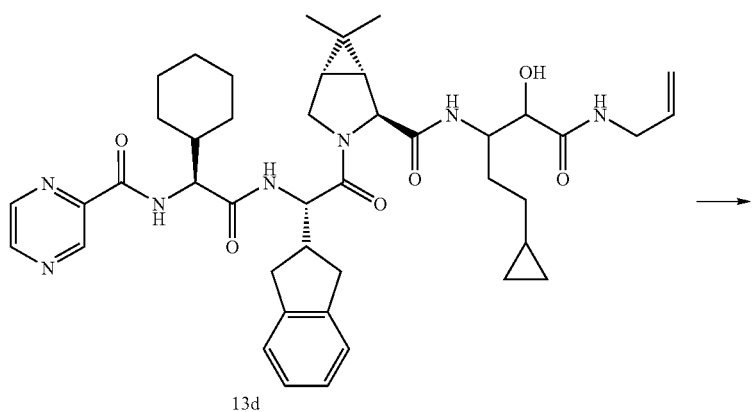

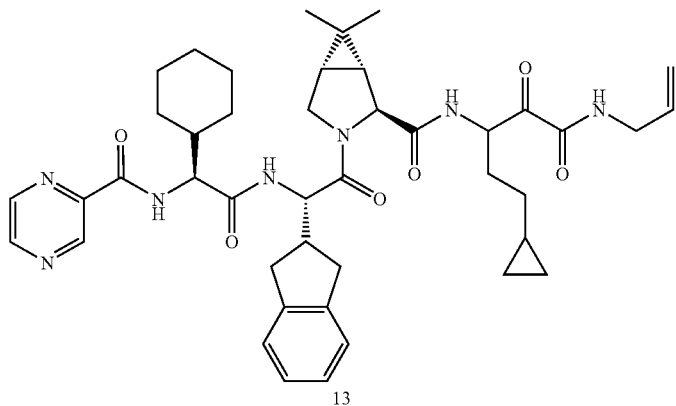

13

A solution of hydroxyamide 13d (0.130 mmol) in 10 mL of dry dichloromethane was treated with Dess-Martin periodinane (2.0 eq, 110 mg). The reaction mixture was stirred at room temperature for 30 min. The mixture was treated with aqueous 1M sodium thiosulfate solution (10 mL) and stirred for 5 min. Aqueous saturated sodium bicarbonate solution (20 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 2:8 to 5:5) to afford the product 13 (69 mg, 70% for two steps) as white solid. HRMS (FAB) calcd for $C_{42}H_{54}N_7O_6$ [M+H] 752.4136; found 752.4122.

PREPARATIVE EXAMPLE 14

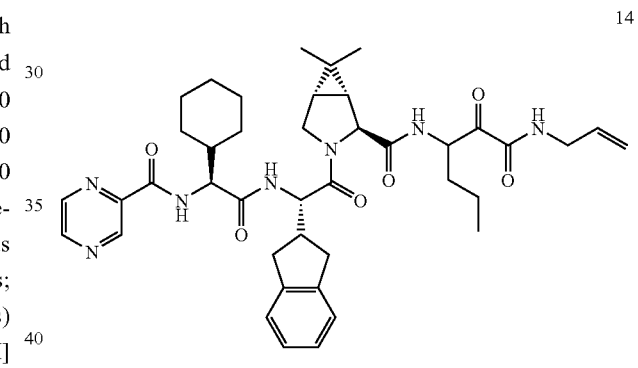

14

Step A

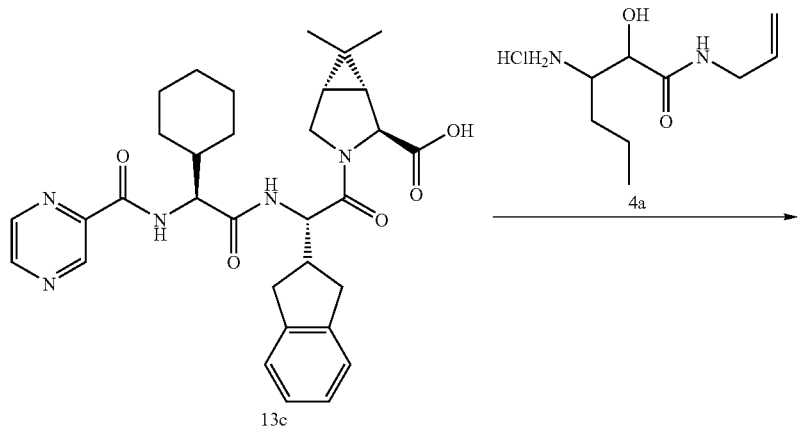

-continued

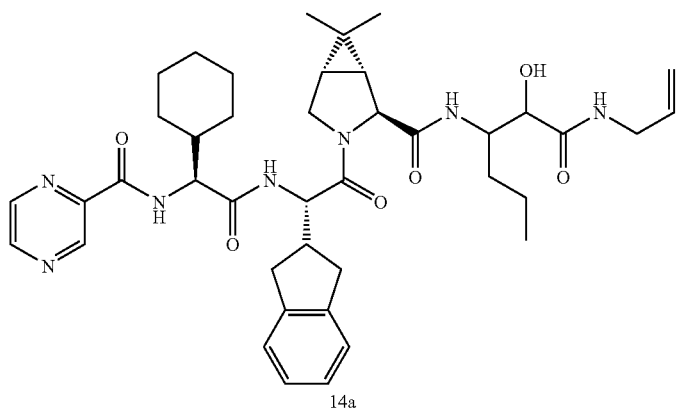

14a

A solution of acid 13c (75 mg) in 4 mL of dry dichloromethane and 2 mL of dry DMF was stirred at 0° C. and treated with HATU (1.4 eq, 69 mg). The amine hydrochloride 4a (1.2 eq, 35 mg) was added followed by N-methylmorpholine (4 eq, 0.06 mL, d 0.920). The reaction mixture was stirred overnight (temp 0 to 25° C.). All the volatiles were removed under vacuum and the residue was dissolved in 50 mL of ethyl acetate. The organic layer was washed with water (20 mL), aqueous 1N HCl (10 mL), aqueous saturated sodium bicarbonate solution (10 mL), and brine (10 mL). The organic layer was dried over magnesium sulfate, filtered and concentrated under reduced pressure. The crude product 14a was used without further purification.

Step B

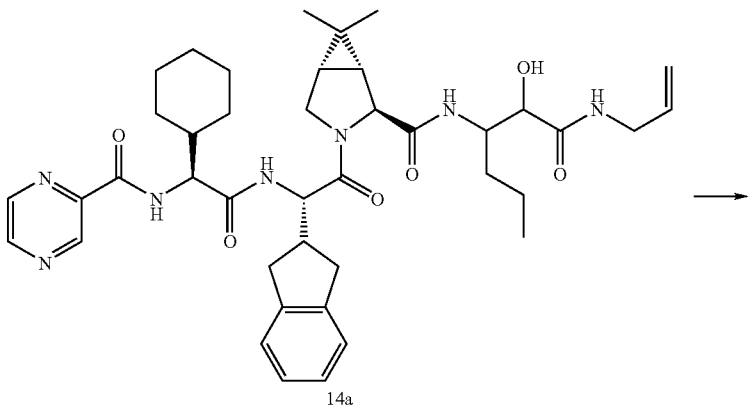

14a

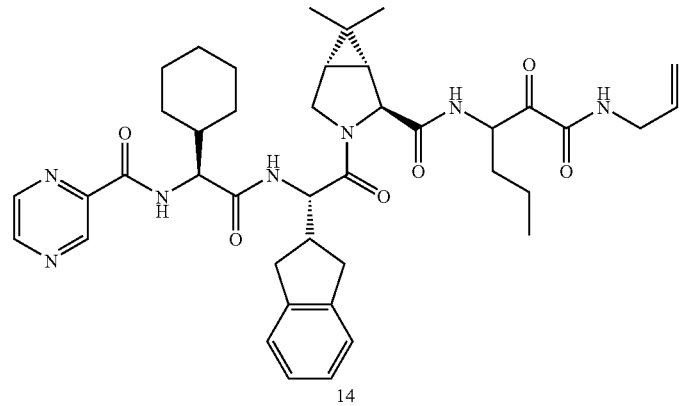

14

A solution of hydroxyamide 14a (0.130 mmol) in 10 mL of dry dichloromethane was treated with Dess-Martin periodinane (2.0 eq, 110 mg). The reaction mixture was stirred at room temperature for 30 min. The mixture was treated with aqueous 1M sodium thiosulfate solution (10 mL) and stirred for 5 min. Aqueous saturated sodium bicarbonate solution (20 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 2:8 to 5:5) to afford the product 14 (66 mg, 69% for two steps) as white solid. HRMS (FAB) calcd for $C_{41}H_{54}N_7O_6$ [M+H] 740.4136; found 740.4146.

PREPARATIVE EXAMPLE 15

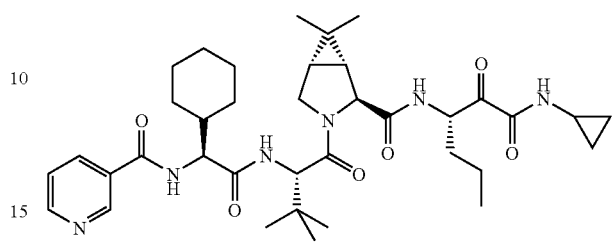

Step A

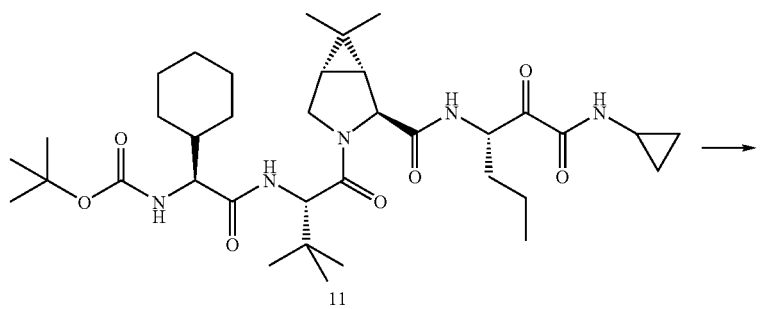

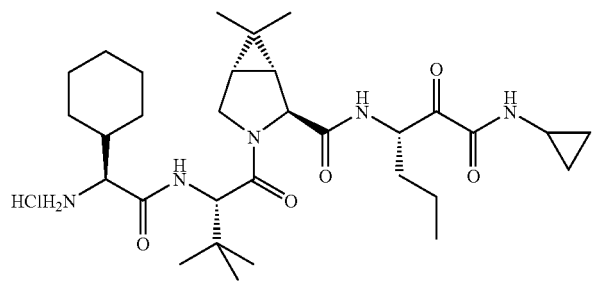

The N-Boc protected amine 11 was dissolved in 5 mL of 4M HCl solution in dioxanes. The resulting solution was stirred at room temperature for about 45 min. All the volatiles were removed under reduced pressure to afford the product 15a (60 mg, 98%) as a white solid. No further purification was carried out for the product.

Step B

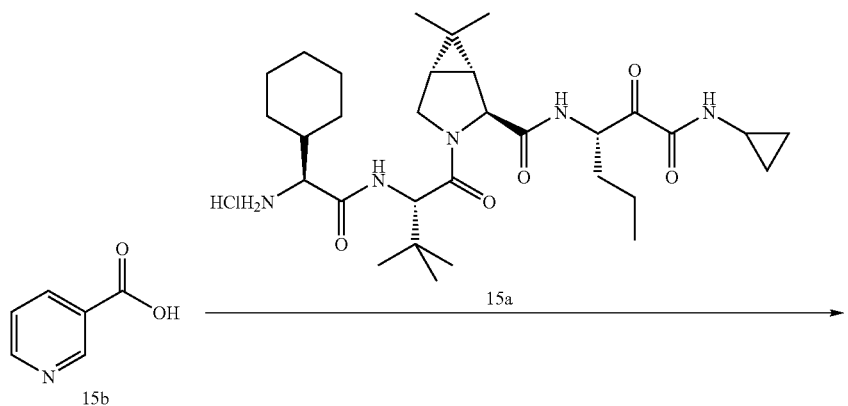

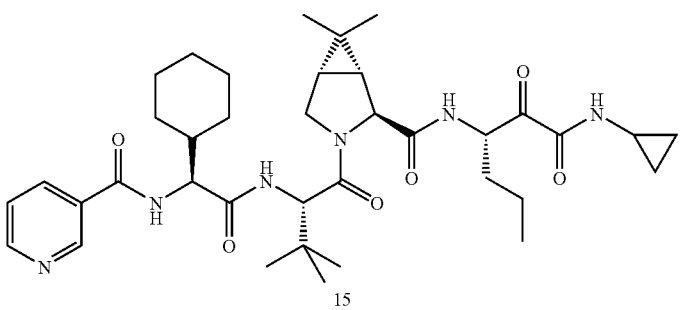

A solution of nicotinic acid 15b (12 mg) in 1 mL of dry DMF was stirred at 0° C. and treated with HATU (1.4 eq, 54 mg). The amine hydrochloride 15a (1.0 eq, 62 mg) was added in 3 mL of dry dichloromethane followed by N-methylmorpholine (4 eq, 0.05 mL, d 0.920). The reaction mixture was stirred overnight (temp 0 to 25° C.). All the volatiles were removed under vacuum and the residue was dissolved in 50 mL of ethyl acetate. The organic layer was washed with water (20 mL), aqueous 1N HCl (10 mL), aqueous saturated sodium bicarbonate solution (10 mL), and brine (10 mL). The organic layer was dried over magnesium sulfate, filtered and concentrated under reduced pressure. The residue was chromatographed on silica gel (gradient: acetone/hexanes; 2:8 to 1:1) to give the product 15 (16 mg, 23%) as a white solid. HRMS (FAB) calcd for $C_{37}H_{55}N_6O_6$ [M+H] 679.4183; found 679.4193.

PREPARATIVE EXAMPLE 16

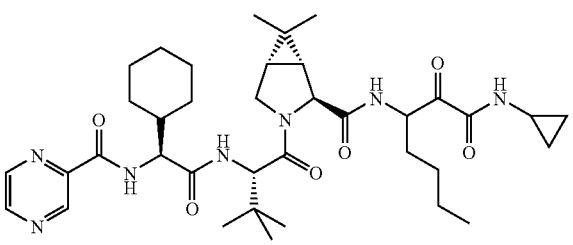

16

Step A

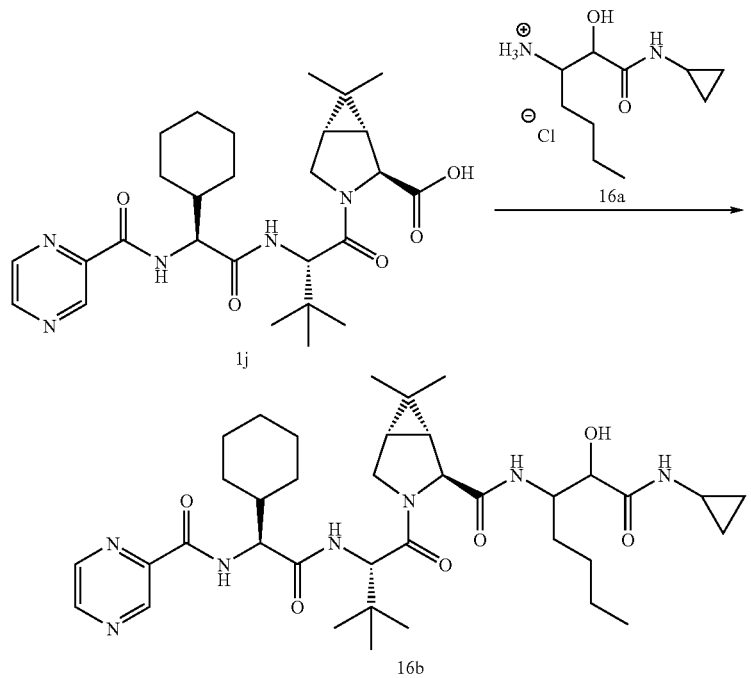

A solution of acid 1j (80 mg) in 2 mL of dry dichloromethane and 2 mL of dry DMF was stirred at 0° C. and treated with HATU (1.4 eq, 83 mg). The amine hydrochloride 16a (1.2 eq, 40 mg) was added followed by N-methylmorpholine (4 eq, 0.07 mL, d 0.920). The reaction mixture was stirred overnight (temp 0 to 25° C.). All the volatiles were removed under vacuum and the residue was dissolved in 50 mL of ethyl acetate. The organic layer was washed with water (20 mL), aqueous 1N HCl (10 mL), aqueous saturated sodium bicarbonate (10 mL), and brine (10 mL). The organic layer was dried over magnesium sulfate, filtered and concentrated under reduced pressure. The crude product 16b was used without further purification.

Step B

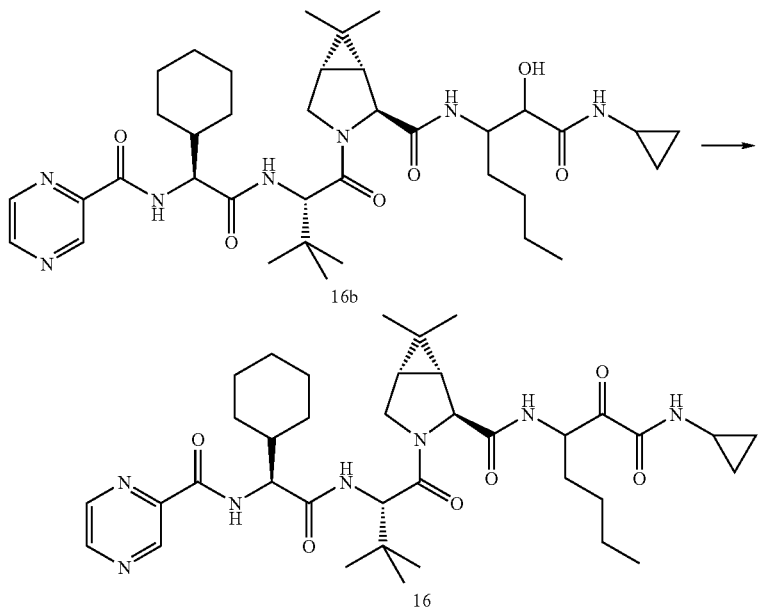

A solution of hydroxyamide 16b (0.155 mmol) in 10 mL of dry dichloromethane was treated with Dess-Martin periodinane (2.0 eq, 131 mg). The reaction mixture was stirred at room temperature for 30 min. The mixture was treated with aqueous 1M sodium thiosulfate solution (10 mL) and stirred for 5 min. Aqueous saturated sodium bicarbonate (20 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 2:8 to 5:5) to afford the product 16 (55 mg, 51%) as white solid. HRMS (FAB) calcd for $C_{37}H_{56}N_7O_6$ [M+H] 694.4292; found 694.4310.

The present invention relates to novel HCV protease inhibitors. This utility can be manifested in their ability to inhibit the HCV NS2/NS4a serine protease. A general procedure used for such manifestation is detailed by the following in vitro assay.

Assay for HCV Protease Inhibitory Activity:

Spectrophotometric Assay: Spectrophotometric assay for the HCV serine protease was performed on the inventive compounds by following the procedure described by R. Zhang et al, *Analytical Biochemistry*, 270 (1999) 268-275, the disclosure of which is incorporated herein by reference. The assay based on the proteolysis of chromogenic ester substrates is suitable for the continuous monitoring of HCV NS3 protease activity. The substrates were derived from the P side of the NS5A-NS5B junction sequence (Ac-DTEDVVX (Nva), where X=A or P) whose C-terminal carboxyl groups were esterified with one of four different chromophoric alcohols (3- or 4-nitrophenol, 7-hydroxy4-methyl-coumarin, or 4-phenylazophenol). Illustrated below are the synthesis, characterization and application of these novel spectrophotometric ester substrates to high throughput screening and detailed kinetic evaluation of HCV NS3 protease inhibitors.

Materials and Methods:

Materials: Chemical reagents for assay related buffers were obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides were synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block was from USA Scientific (Ocala, Fla.) and the 96-well plate vortexer is from Labline Instruments (Melrose Park, Ill.). A Spectramax Plus microtiter plate reader with monochrometer was obtained from Molecular Devices (Sunnyvale, Calif.).

Enzyme Preparation: Recombinant heterodimeric HCV NS3/NS4A protease (strain 1a) was prepared by using the procedures published previously (D. L. Sali et al, *Biochemistry*, 37 (1998) 3392-3401). Protein concentrations were determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) was exchanged for the assay buffer (25 mM MOPS pH 6.5, 300 mM NaCl, 10% glycerol, 0.05% lauryl maltoside, 5 µM EDTA and 5 µM DTT) utilizing a Biorad Bio-Spin P-6 prepacked column.

Substrate Synthesis and Purification: The synthesis of the substrates was done as reported by R. Zhang et al, (ibid.) and is initiated by anchoring Fmoc-Nva-OH to 2-chlorotrityl chloride resin using a standard protocol (K. Barlos et al, *Int. J. Pept. Protein Res.*, 37 (1991), 513-520). The peptides were subsequently assembled, using Fmoc chemistry, either manually or on an automatic ABI model 431 peptide synthesizer. The N-acetylated and fully protected peptide fragments were cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash was evaporated azeotropically (or repeatedly extracted by aqueous $Na_2CO_3$ solution) to remove the acid used in cleavage. The DCM phase was dried over $Na_2SO_4$ and evaporated.

The ester substrates were assembled using standard acid-alcohol coupling procedures (K. Holmber et al, *Acta Chem. Scand.*, B33 (1979) 410-412). Peptide fragments were dissolved in anhydrous pyridine (30-60 mg/ml) to which 10 molar equivalents of chromophore and a catalytic amount (0.1 eq.) of para-toluenesulfonic acid (pTSA) were added. Dicyclohexylcarbodiimide (DCC, 3 eq.) was added to initiate the coupling reactions. Product formation was monitored by HPLC and could be found to be complete following 12-72 hour reaction at room temperature. Pyridine solvent was evaporated under vacuum and further removed by azeotropic evaporation with toluene. The peptide ester was deprotected with 95% TFA in DCM for two hours and extracted three times with anhydrous ethyl ether to remove excess chromophore. The deprotected substrate was purified by reversed phase HPLC on a C3 or C8 column with a 30% to 60% acetonitrile gradient (using six column volumes). The overall yield following HPLC purification was approximately 20-30%. The molecular mass can be confirmed by electrospray ionization mass spectroscopy. The substrates were stored in dry powder form under desiccation.

Spectra of Substrates and Products: Spectra of substrates and the corresponding chromophore products were obtained in the pH 6.5 assay buffer. Extinction coefficients were determined at the optimal off-peak wavelength in 1-cm cuvettes (340 nm for 3-Np and HMC, 370 nm for PAP and 400 nm for 4-Np) using multiple dilutions. The optimal off-peak wavelength was defined as that wavelength yielding the maximum fractional difference in absorbance between substrate and product (product OD—substrate OD)/substrate OD).

Protease Assay: HCV protease assays were performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) were optimized for the NS3/NS4A heterodimer (D. L. Sali et al, ibid.)). Typically, 150 µl mixtures of buffer, substrate and inhibitor were placed in wells (final concentration of DMSO ≤4% v/v) and allowed to preincubate at 30° C. for approximately 3 minutes. Fifty µls of prewarmed protease (12 nM, 30° C.) in assay buffer, was then used to initiate the reaction (final volume 200 µl). The plates were monitored over the length of the assay (60 minutes) for change in absorbance at the appropriate wavelength (340 nm for 3-Np and HMC, 370 nm for PAP, and 400 nm for 4-Np) using a Spectramax Plus microtiter plate reader equipped with a monochrometer (acceptable results was obtained with plate readers that utilize cutoff filters). Proteolytic cleavage of the ester linkage between the Nva and the chromophore was monitored at the appropriate wavelength against a no enzyme blank as a control for non-enzymatic hydrolysis. The evaluation of substrate kinetic parameters was performed over a 30-fold substrate concentration range (~6-200 μM). Initial velocities were determined using linear regression and kinetic constants are obtained by fitting the data to the Michaelis-Menten equation using non-linear regression analysis (Mac Curve Fit 1.1, K. Raner). Turnover numbers ($k_{cat}$) were calculated assuming the enzyme is fully active.

Evaluation of Inhibitors and Inactivators: The inhibition constants ($K_i$) for the competitive inhibitors Ac-D-(D-Gla)-L-I-(Cha)-C—OH (27), Ac-DTEDVVA(Nva)-OH and Ac-DTEDVVP(Nva)-OH were determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i = 1 + [I]_o/(K_i(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data were fitted using linear regression and the resulting slope, $1/(K_i(1+[S]_o/K_m))$, was used to calculate the $K_i^*$ value. The thus-obtained Ki* values for some of the inventive compounds are shown in Table 2 and Table 3.

TABLE 2

| Entry in Table | Structure | Ki* |
|---|---|---|
| 1 | 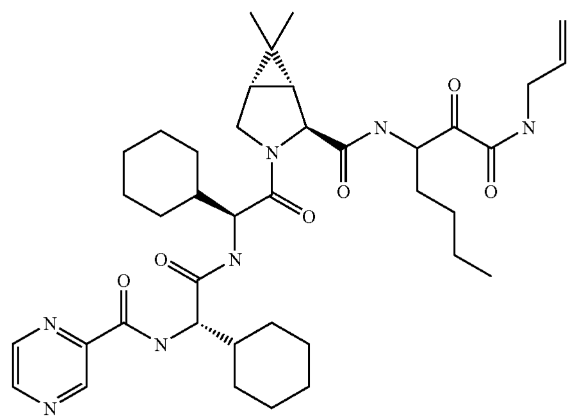 | A |
| 2 | 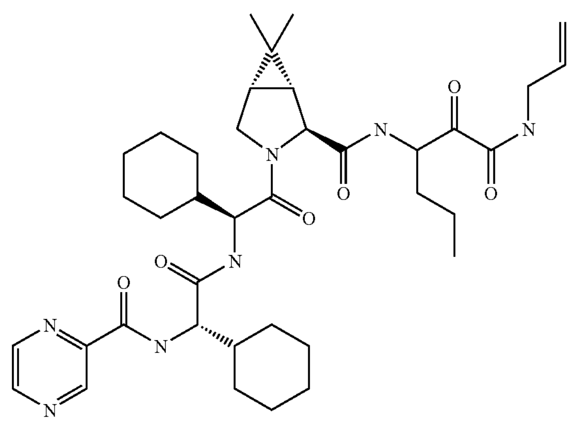 | A |
| 3 | 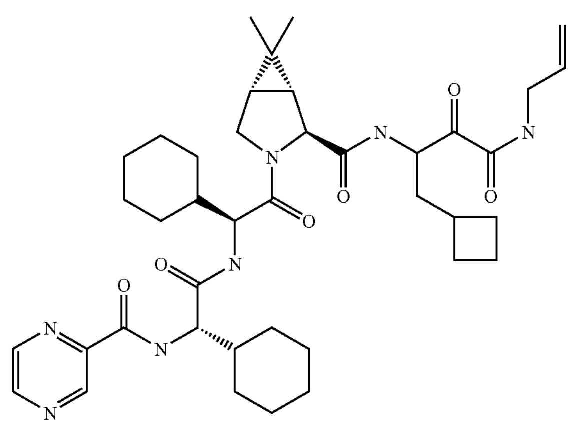 | A |

TABLE 2-continued
| Entry in Table | Structure | Ki* |
|---|---|---|
| 4 | 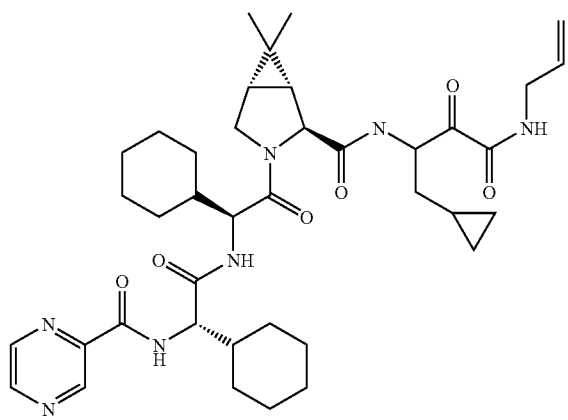 | A |
| 5 | 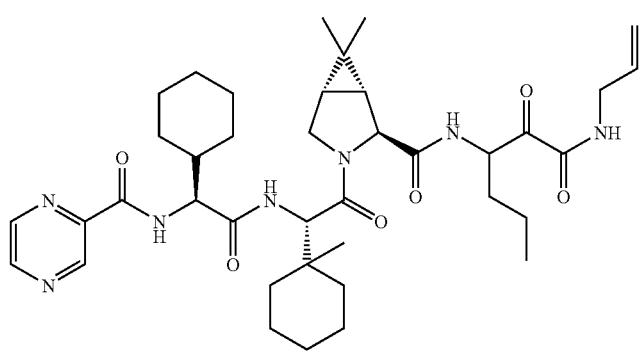 | A |
| 6 | 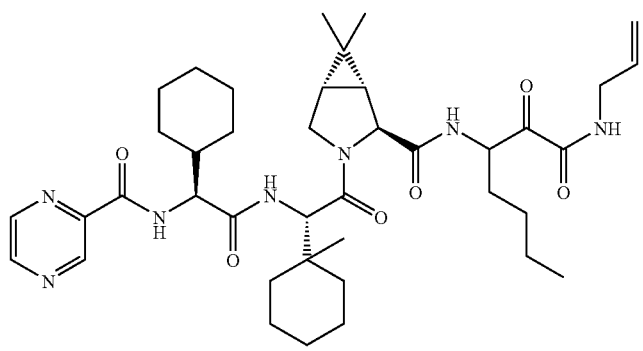 | A |
| 7 | 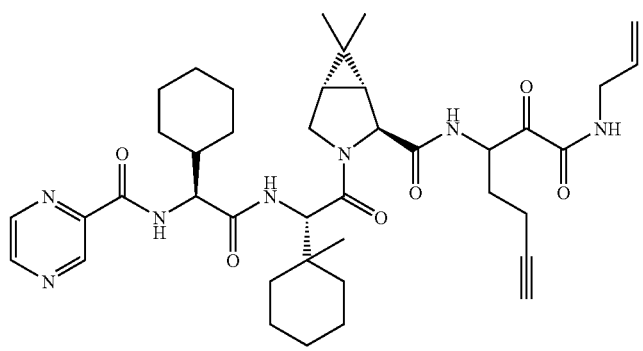 | A |

TABLE 2-continued
| Entry in Table | Structure | Ki* |
|---|---|---|
| 8 | 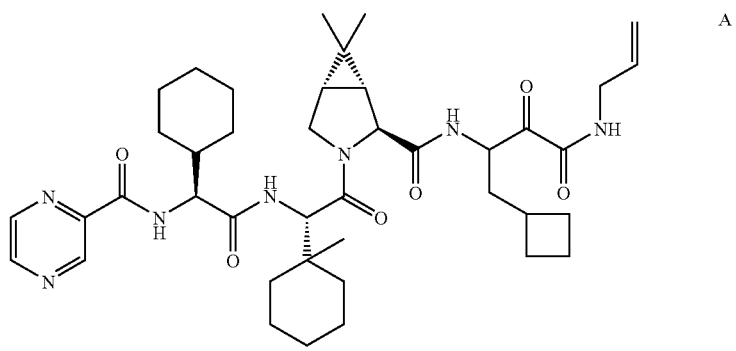 | A |
| 9 | 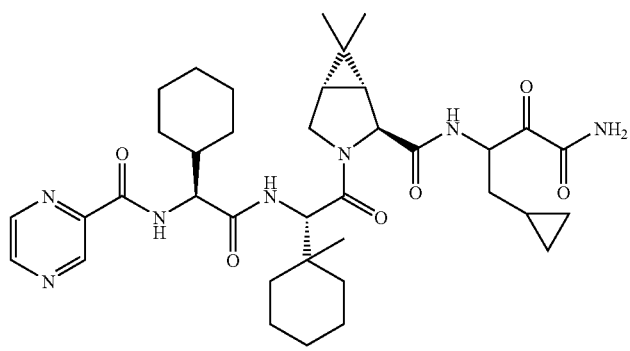 | A |
| 10 | 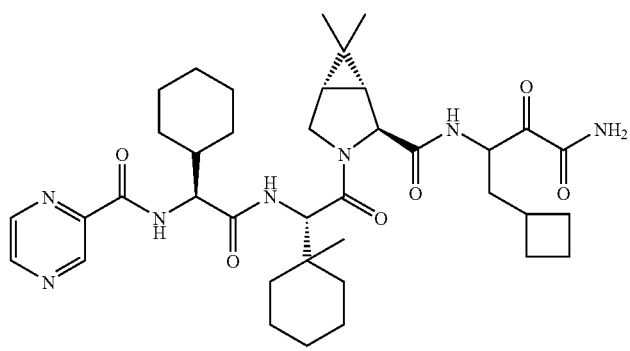 | A |
| 11 | 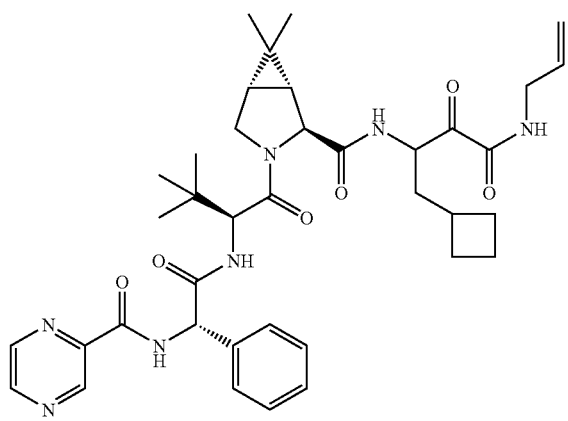 | B |

TABLE 2-continued
| Entry in Table | Structure | Ki* |
|---|---|---|
| 12 | 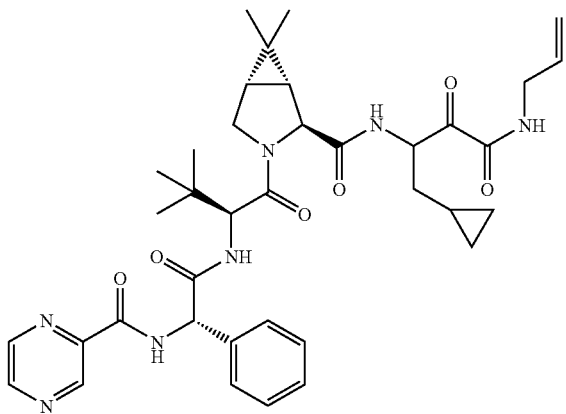 | A |
| 13 | 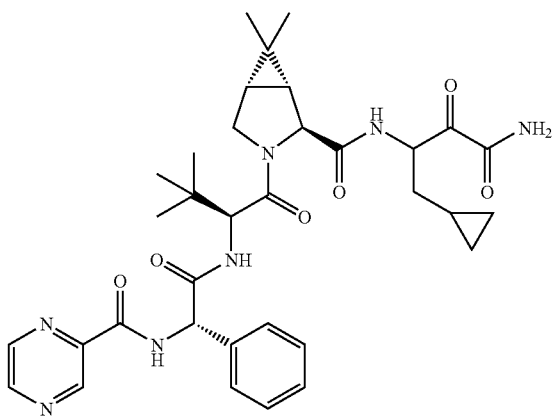 | A |
| 14 | 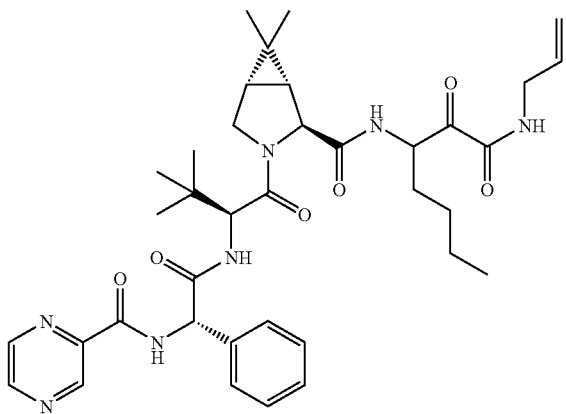 | A |

TABLE 2-continued
| Entry in Table | Structure | Ki* |
|---|---|---|
| 15 | 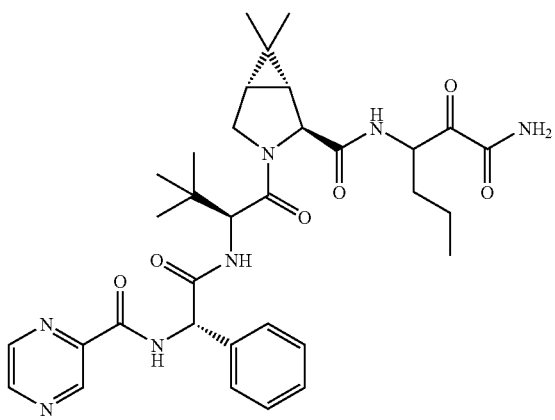 | A |
| 16 | 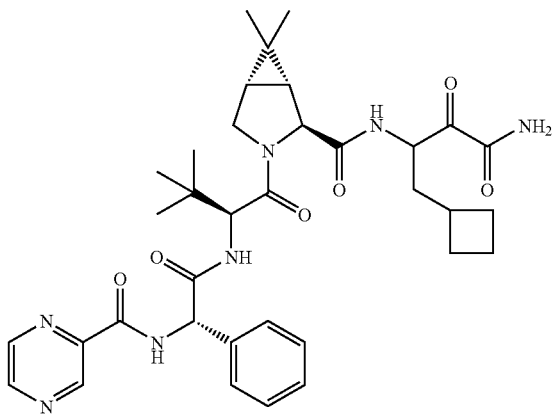 | A |
| 17 | 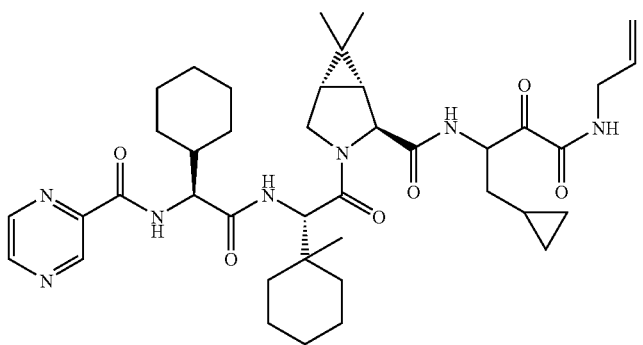 | A |
| 18 | 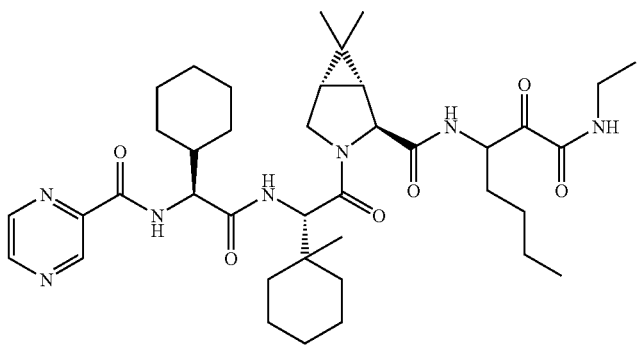 | A |

TABLE 2-continued
| Entry in Table | Structure | Ki* |
|---|---|---|
| 19 | 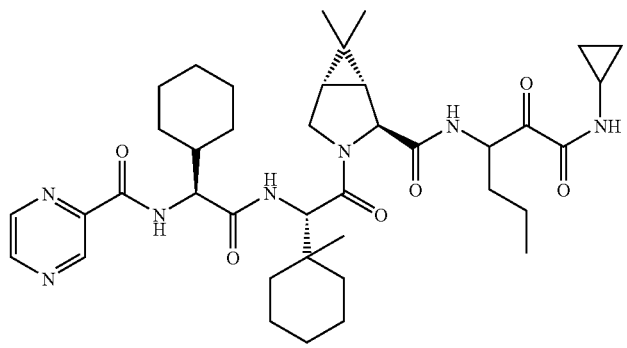 | A |
| 20 | 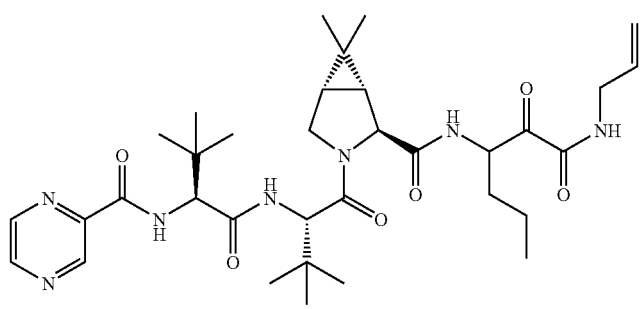 | A |
| 21 | 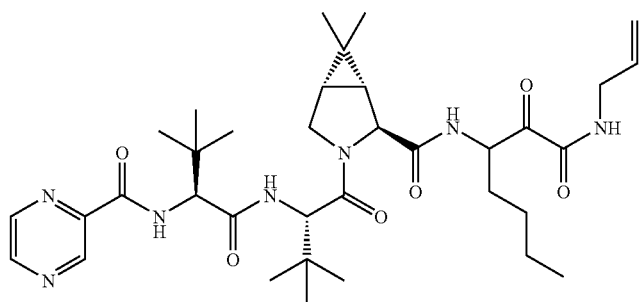 | B |
| 22 | 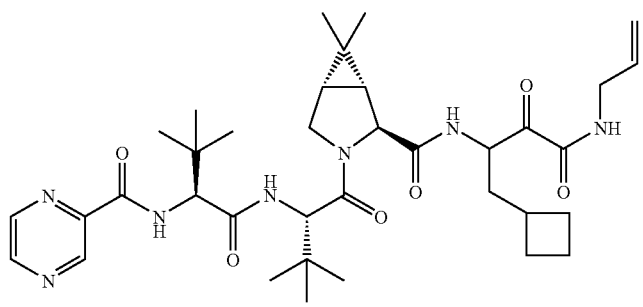 | B |

TABLE 2-continued
| Entry in Table | Structure | Ki* |
|---|---|---|
| 23 | 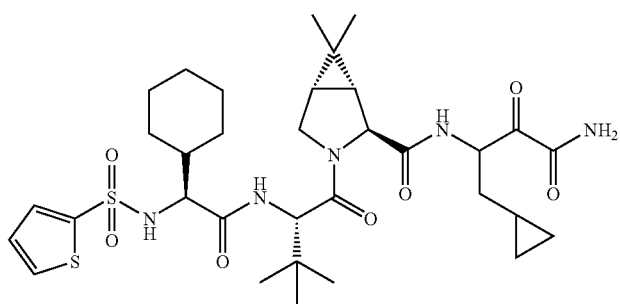 | A |
| 24 | 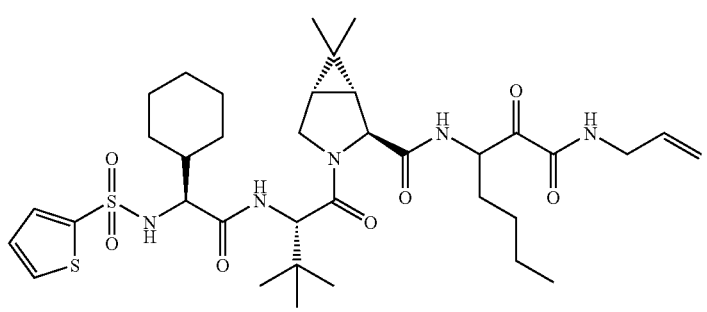 | B |
| 25 | 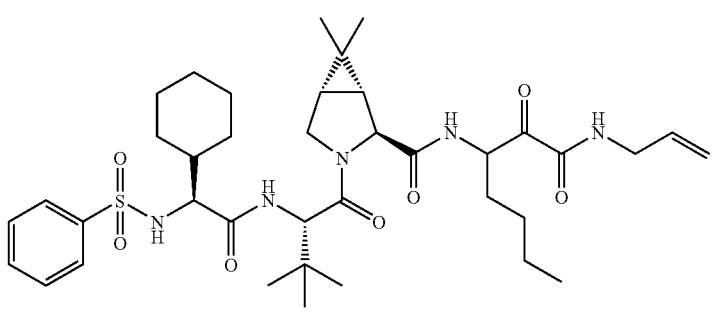 | B |
| 26 | 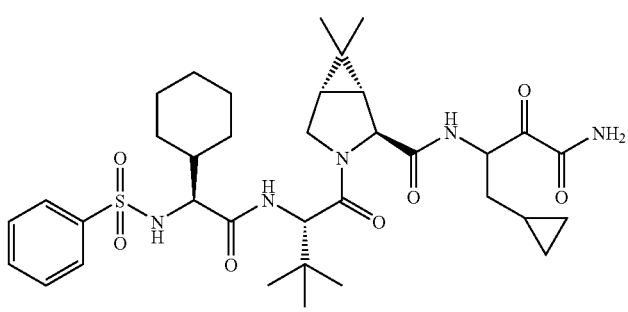 | A |

TABLE 2-continued
| Entry in Table | Structure | Ki* |
|---|---|---|
| 27 | 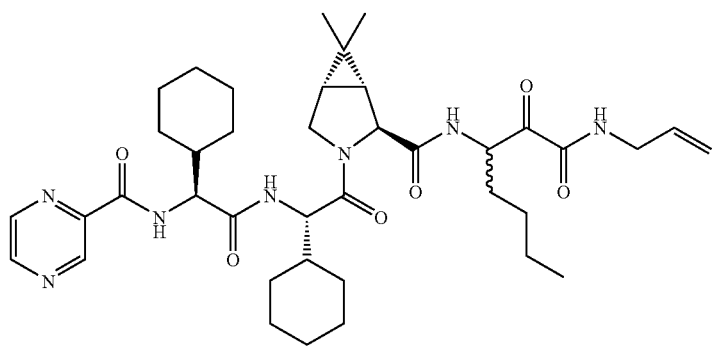 | A |
| 28 | 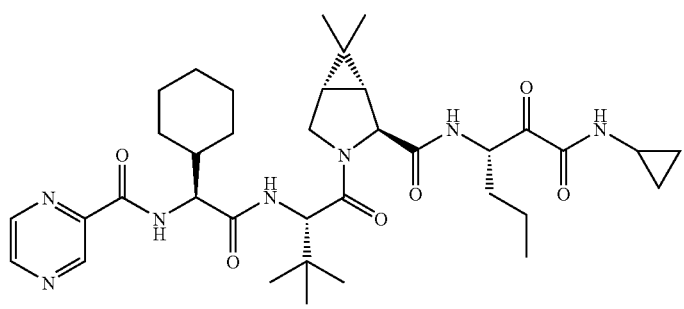 | A |
| 29 | 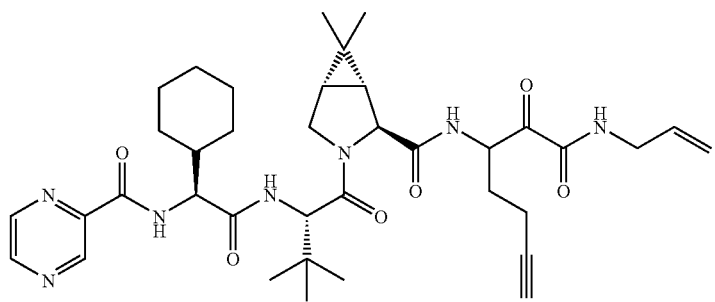 | A |
| 30 | 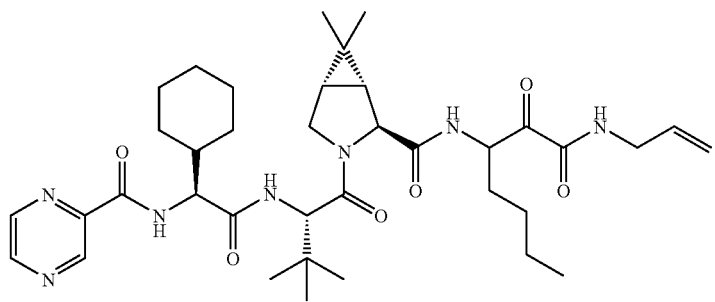 | A |

TABLE 2-continued

| Entry in Table | Structure | Ki* |
|---|---|---|
| 31 | 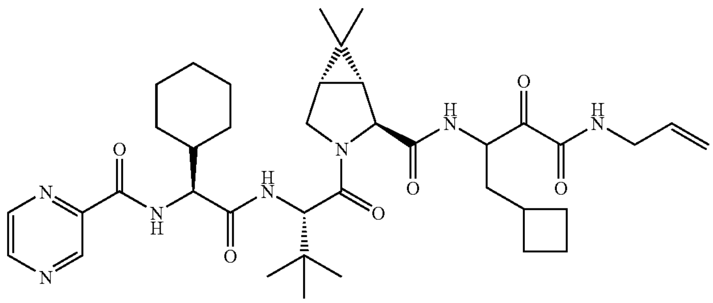 | A |
| 32 | 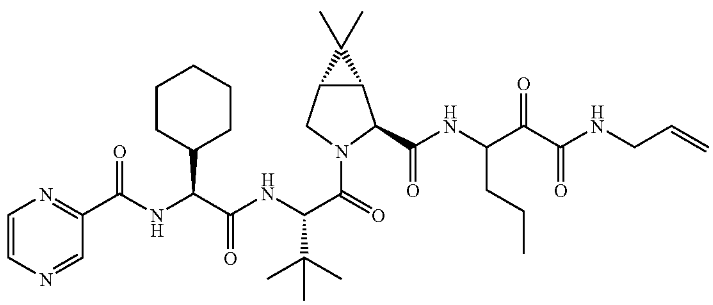 | A |
| 33 | 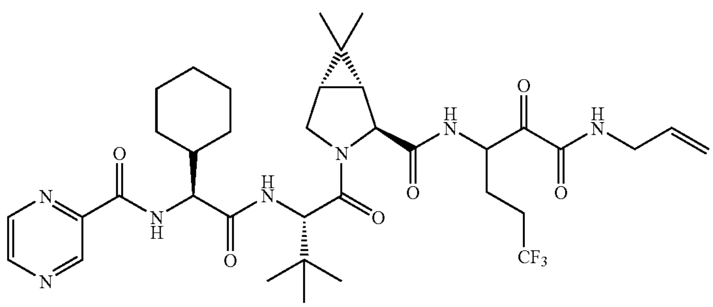 | A |
| 34 | 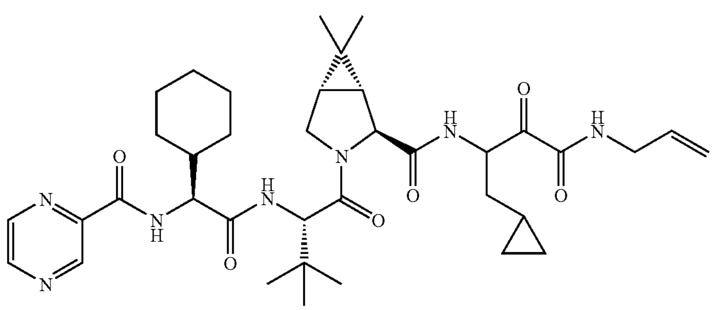 | A |
| 35 | 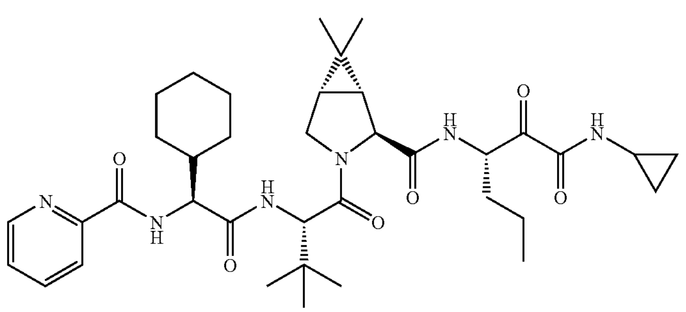 | A |

TABLE 2-continued
| Entry in Table | Structure | Ki* |
|---|---|---|
| 36 | 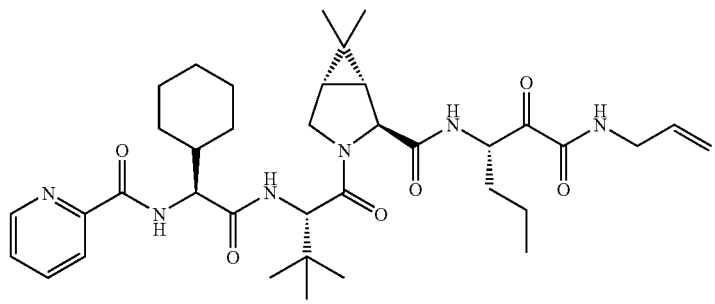 | A |
| 37 | 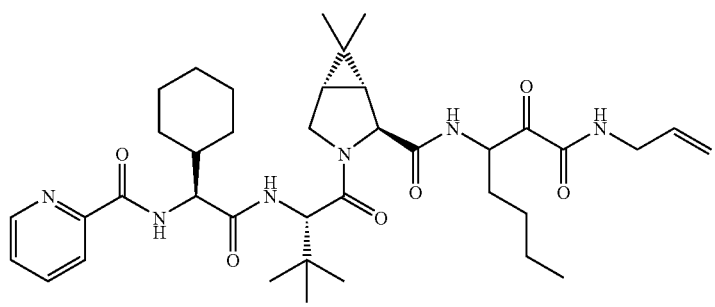 | A |
| 38 | 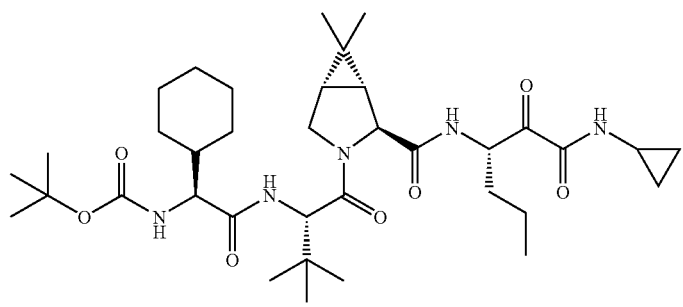 | B |
| 39 | 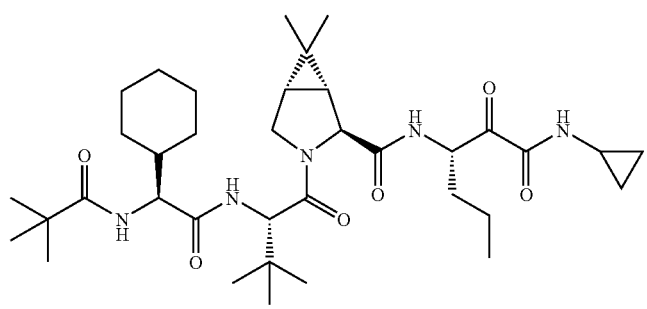 | A |

TABLE 2-continued
| Entry in Table | Structure | Ki* |
|---|---|---|
| 40 | 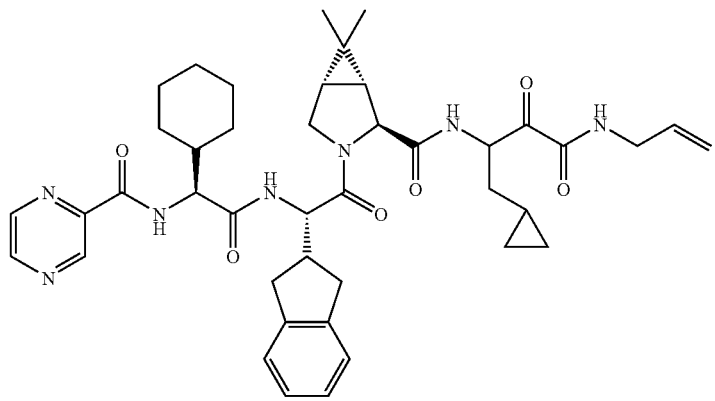 | A |
| 41 | 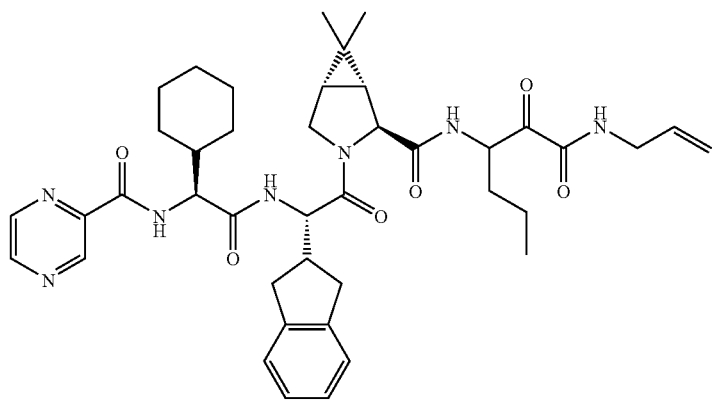 | A |
| 42 | 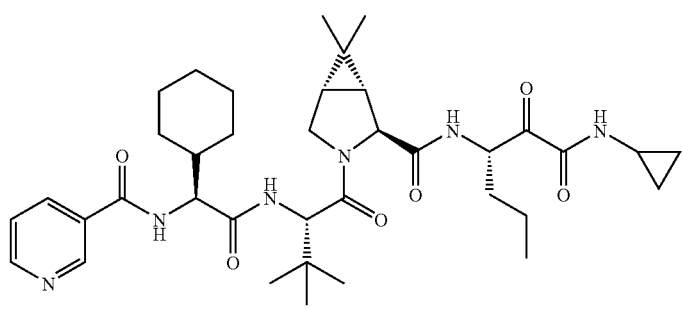 | A |
| 43 | 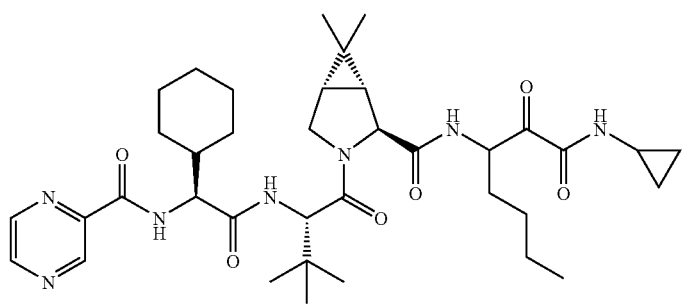 | A |

TABLE 2-continued
| Entry in Table | Structure | Ki* |
|---|---|---|
| 44 | 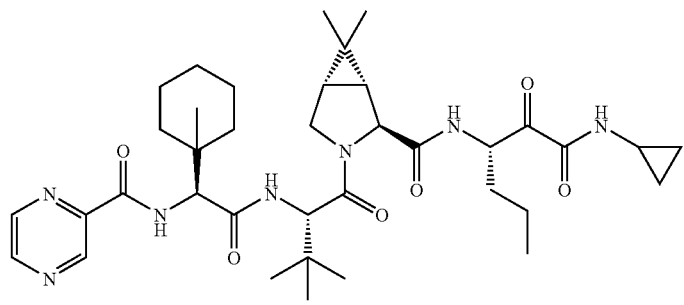 | A |
| 45 | 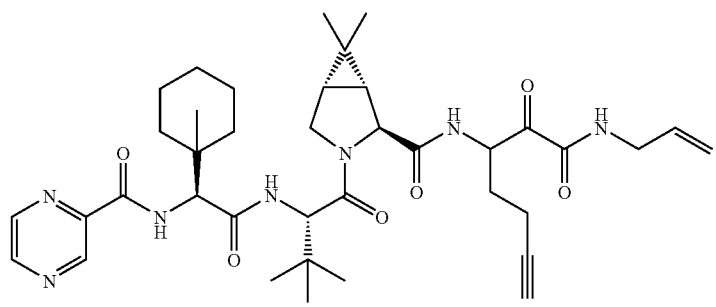 | A |
| 46 | 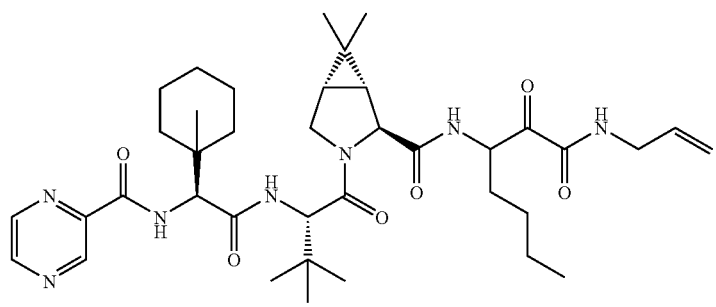 | A |
| 47 | 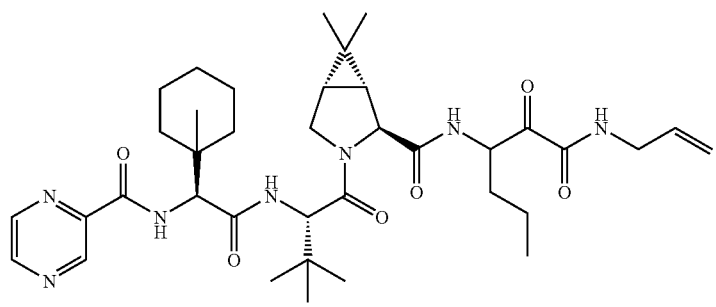 | A |

TABLE 2-continued
| Entry in Table | Structure | Ki* |
|---|---|---|
| 18 | 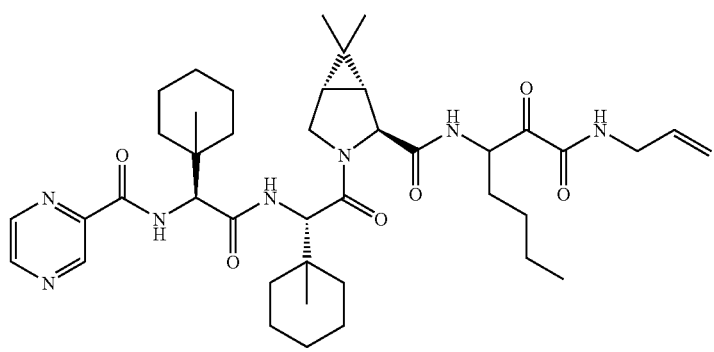 | A |
| 49 | 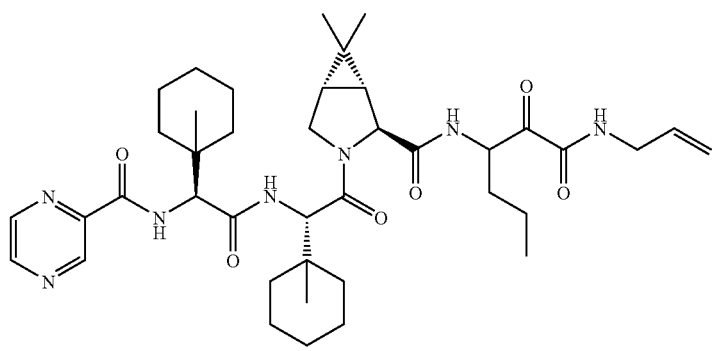 | A |
| 50 | 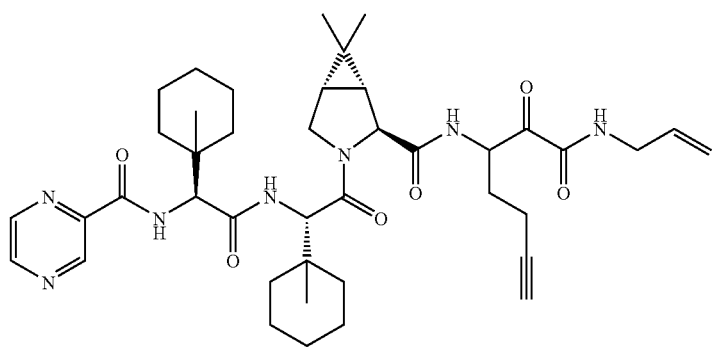 | A |
| 51 | 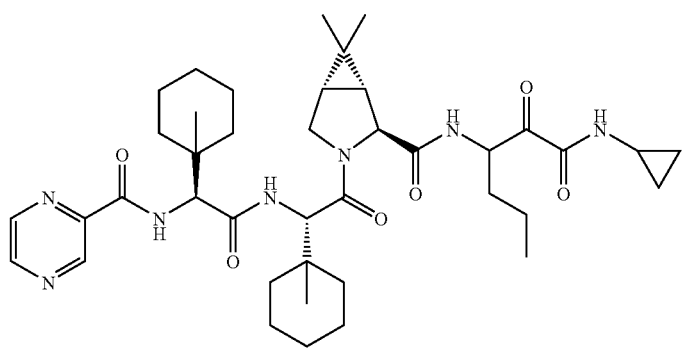 | A |
Range A ≦100 nM; B >100 nM ≦1000 nM; C >1000 nM.

TABLE 3

| Entry | Structure | Ki* (nM) |
|-------|-----------|----------|
| 1 | 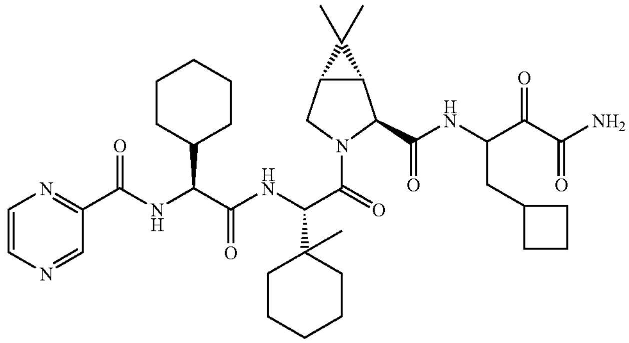 | 3.2 |
| 2 | 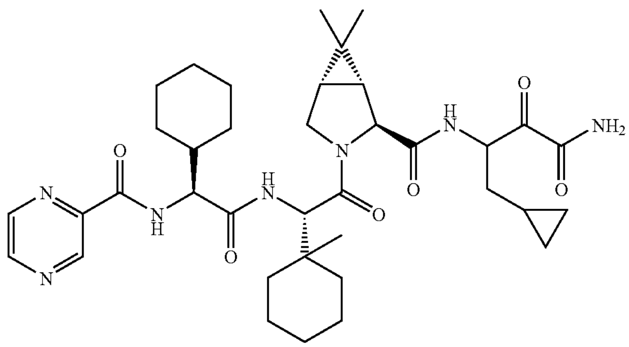 | 4 |
| 3 | 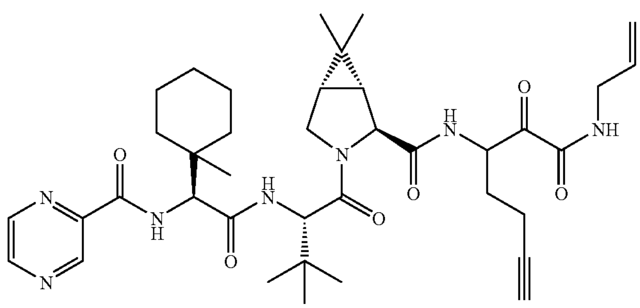 | 4 |
| 4 | 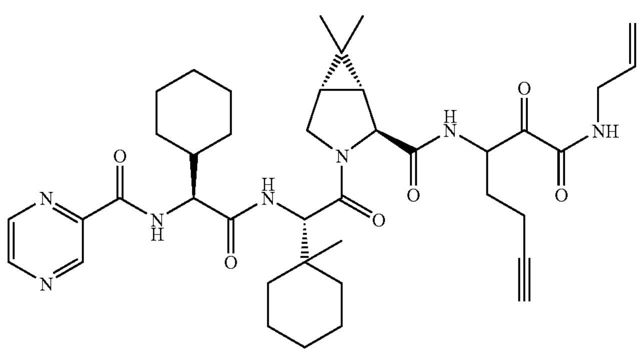 | 5 |

TABLE 3-continued

| Entry | Structure | Ki* (nM) |
|---|---|---|
| 5 | 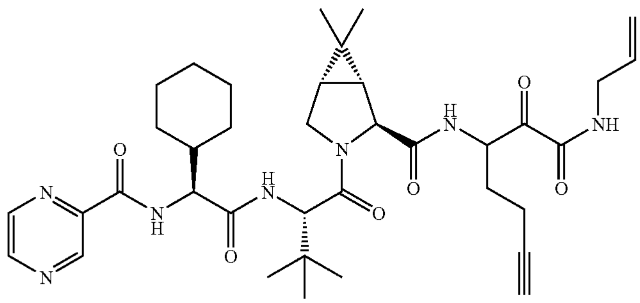 | 6 |
| 6 | 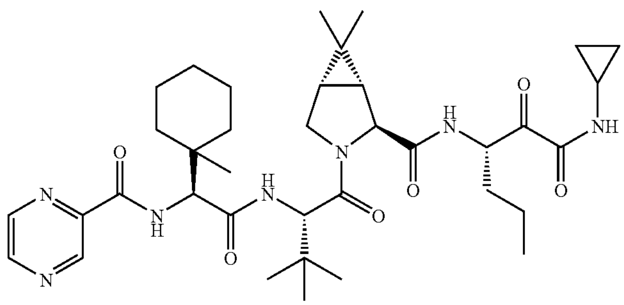 | 7 |
| 7 | 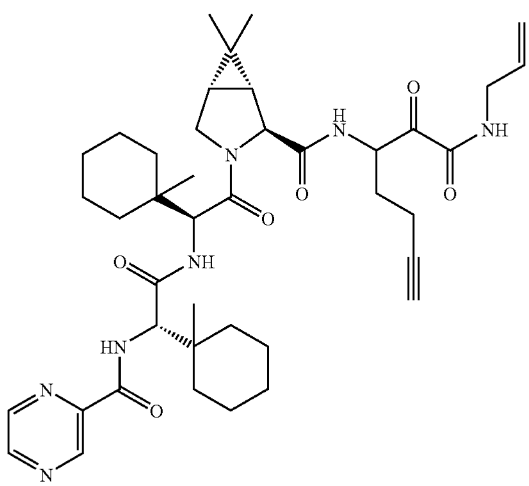 | 7 |
| 8 | 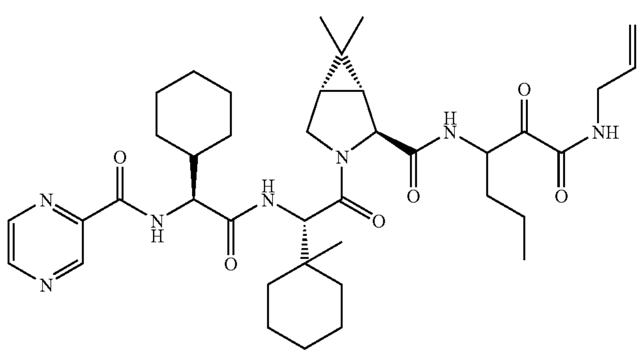 | 9 |

TABLE 3-continued

| Entry | Structure | Ki* (nM) |
|---|---|---|
| 9 | 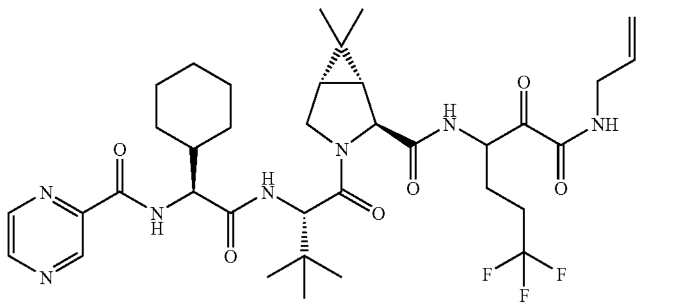 | 12 |
| 10 | 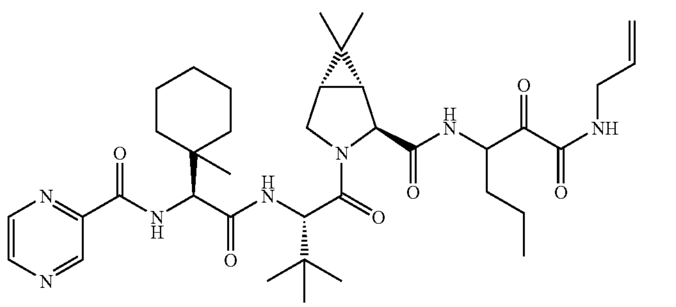 | 12 |
| 11 | 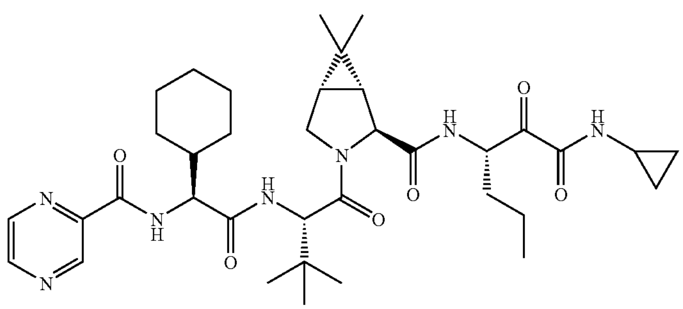 | 13 |
| 12 | 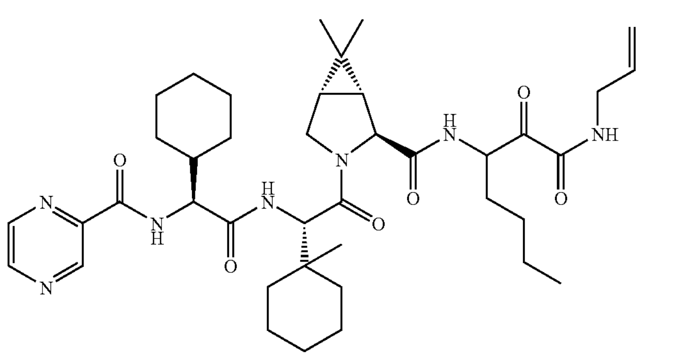 | 13 |

TABLE 3-continued

| Entry | Structure | Ki* (nM) |
|---|---|---|
| 13 | 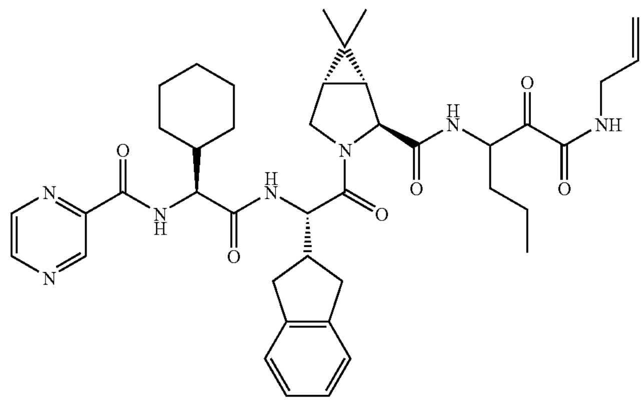 | 13 |
| 14 | 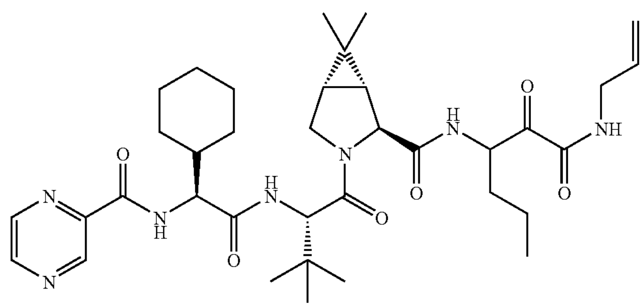 | 14 |
| 15 | 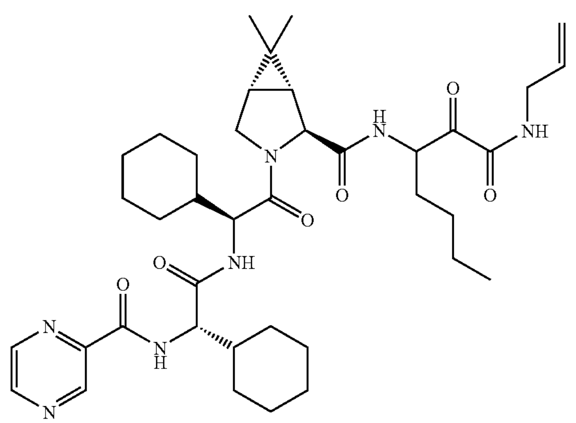 | 16 |
| 16 | 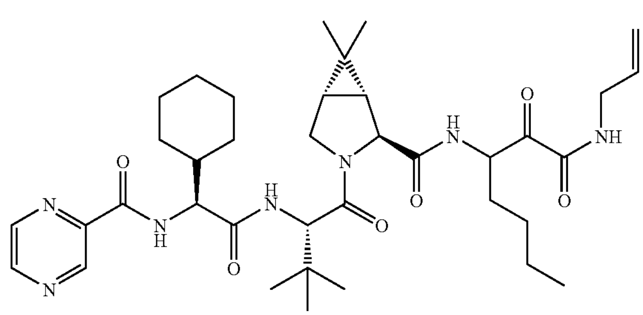 | 16 |

TABLE 3-continued

| Entry | Structure | Ki* (nM) |
|---|---|---|
| 17 | 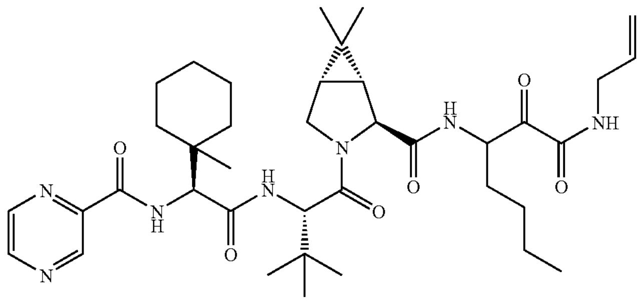 | 17 |
| 18 | 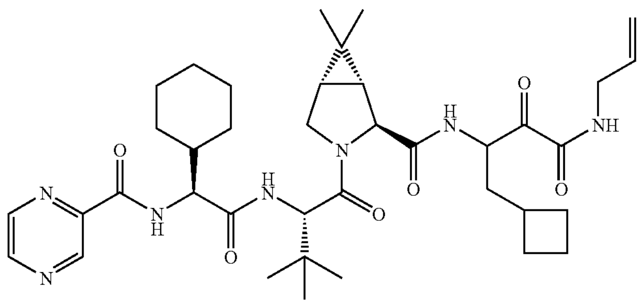 | 18 |
| 19 | 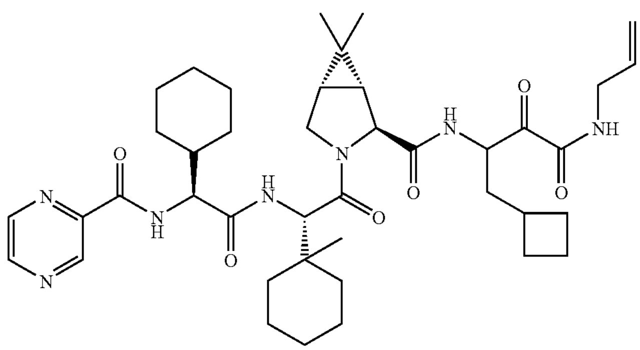 | 19 |
| 20 | 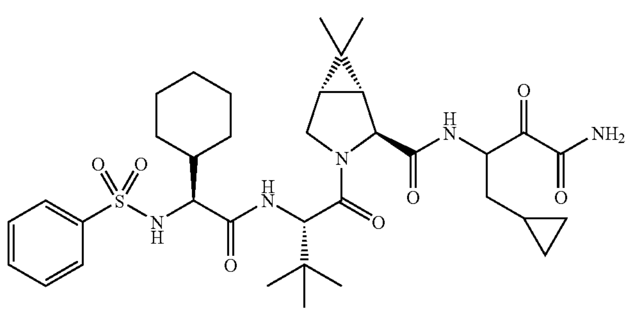 | 20 |

TABLE 3-continued

| Entry | Structure | Ki* (nM) |
|---|---|---|
| 21 | 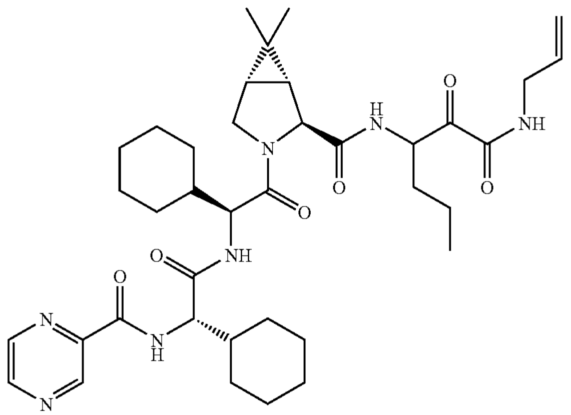 | 22 |
| 22 | 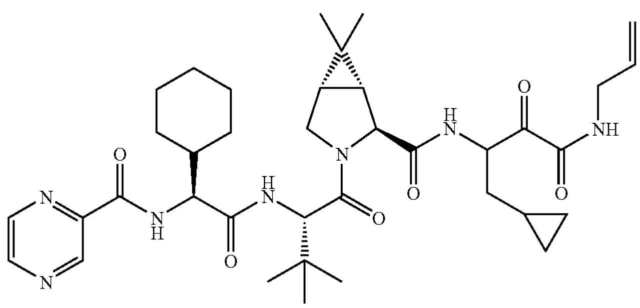 | 22 |
| 23 | 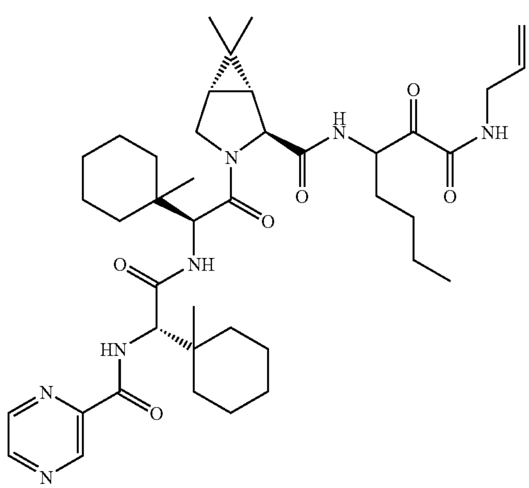 | 22 |

TABLE 3-continued

| Entry | Structure | Ki* (nM) |
|---|---|---|
| 24 | 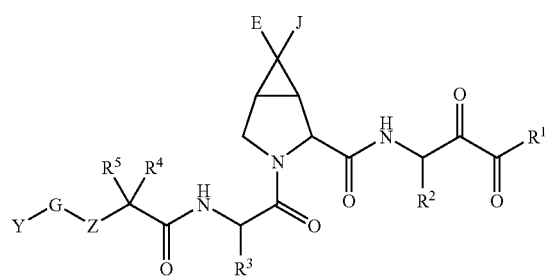 | 23 |

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound, or enantiomers, stereoisomers, rotamers, tautomers, diastereomers, or racemates of said compound, or a pharmaceutically acceptable salt, solvate or ester of said compound, said compound having the general structure shown in Formula I:

Formula I wherein:
- $R^1$ is H, $OR^8$, $NR^9R^{10}$, or $CHR^9R^{10}$, wherein $R^8$, $R^9$ and $R^{10}$ can be the same or different, each being independently selected from the group consisting of H, alkyl-, aryl-, heteroalkyl-, heteroaryl-, cycloalkyl-, cycloalkyl-, arylalkyl-, and heteroarylalkyl;
- E and J can be the same or different, each being independently selected from the group consisting of R, OR, NHR, $NRR^7$, SR, halo, and $S(O_2)R$, or E and J can be directly connected to each other to form either a three to eight-membered cycloalkyl, or a three to eight-membered heterocyclyl moiety;
- Z is N(H), N(R), or O;
- G is C(=O) or $S(O_2)$, with the proviso that when Z is O, G is not $S(O_2)$;
- Y is selected from the group consisting of:

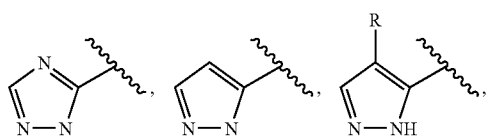

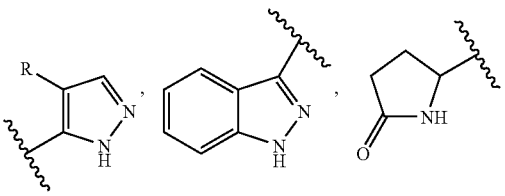

X = O, S, NH

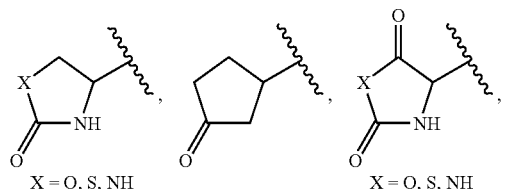

X = O, S, NH

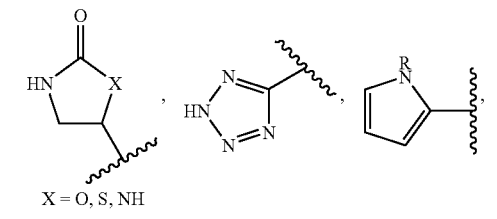

-continued

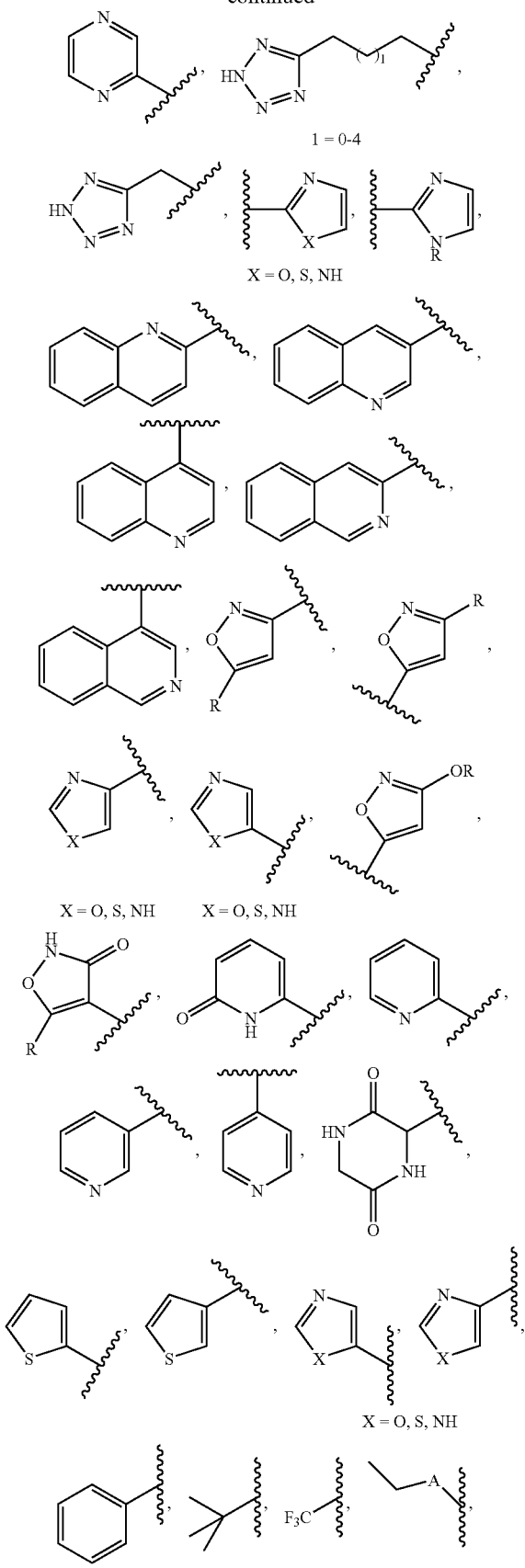

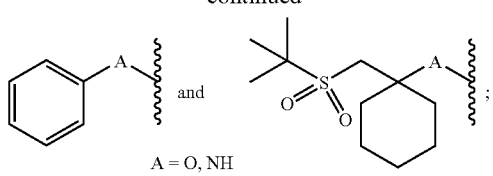

A = O, NH

R, R⁷, R², R³, R⁴ and R⁵ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-, wherein each of said heteroalkyl, heteroaryl and heterocyclyl independently has one to six oxygen, nitrogen, sulfur, or phosphorus atoms;

wherein each of said alkyl, heteroalkyl, alkenyl, alkynyl, aryl, heteroaryl, cycloalkyl and heterocyclyl moieties can be unsubstituted or optionally independently substituted with one or more moieties selected from the group consisting of alkyl, alkenyl, alkynyl, aryl, aralkyl, cycloalkyl, heterocyclyl, halo, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate.

2. The compound of claim 1, wherein $R^2$ is selected from the group consisting of the following moieties:

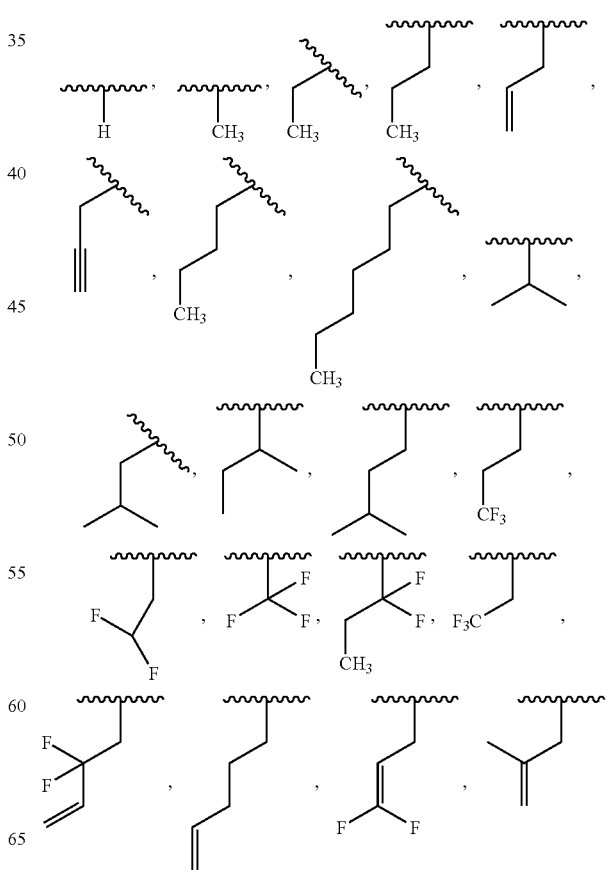

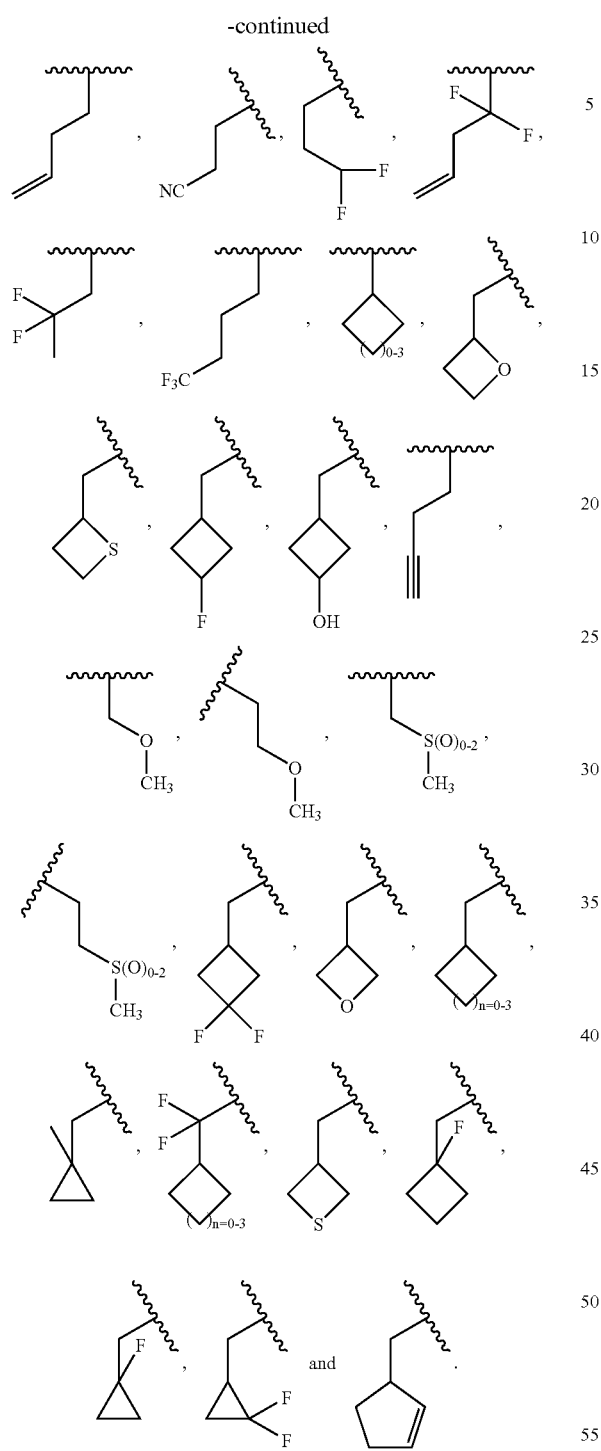
3. The compound of claim 1, wherein $R^3$ is selected from the group consisting of:
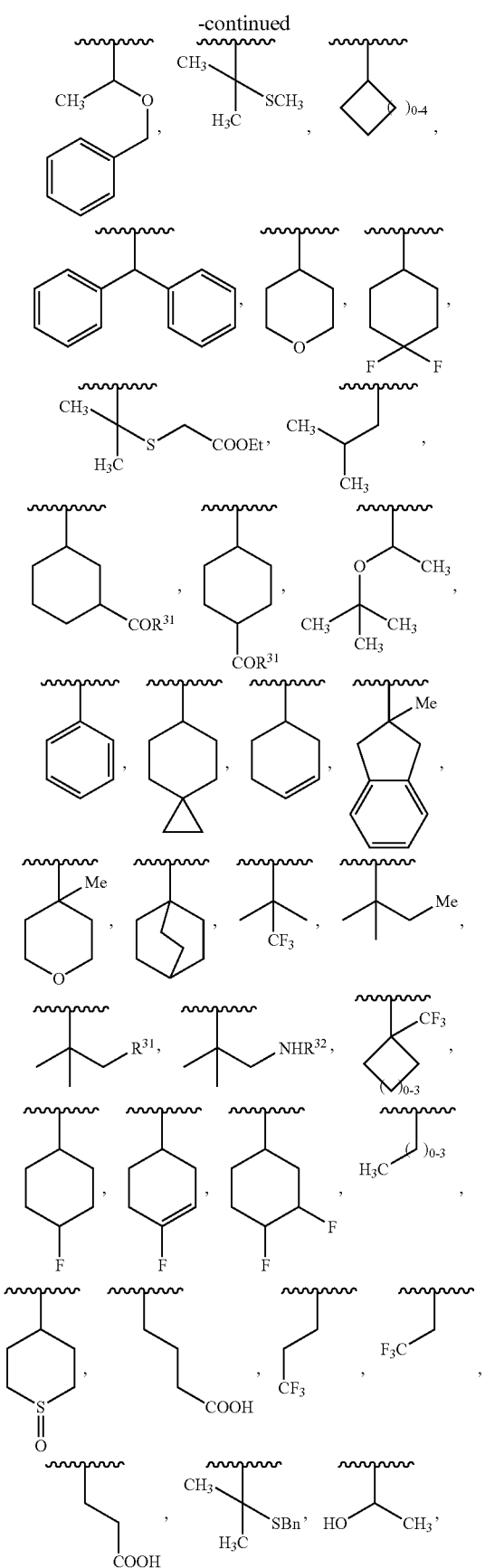

-continued
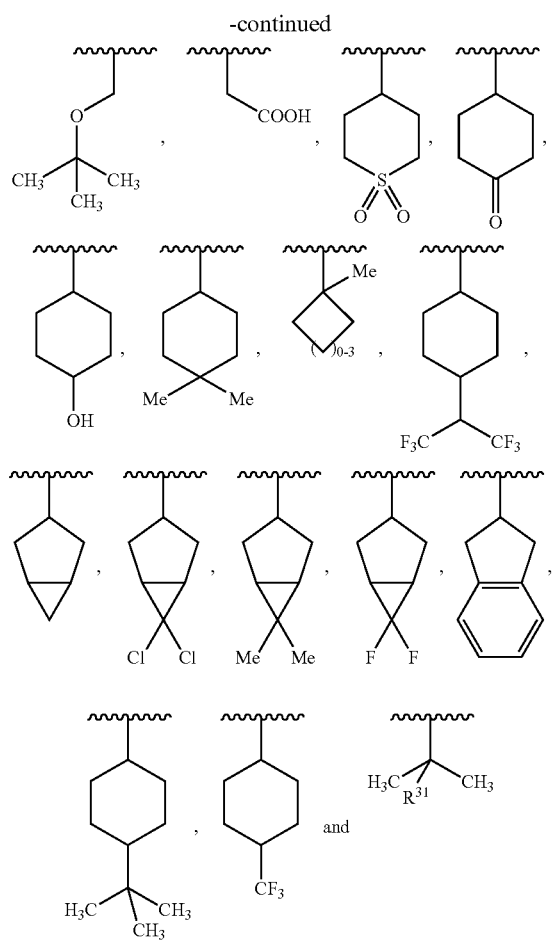
wherein R³¹ is OH or O-alkyl; and
R³² is H, C(O)CH₃, C(O)OtBu or C(O)N(H)tBu.
4. The compound of claim 3, wherein R³ is selected from the group consisting of:
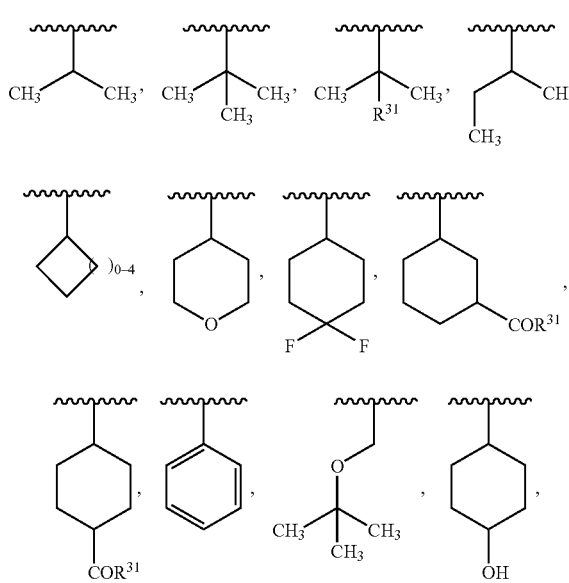
-continued
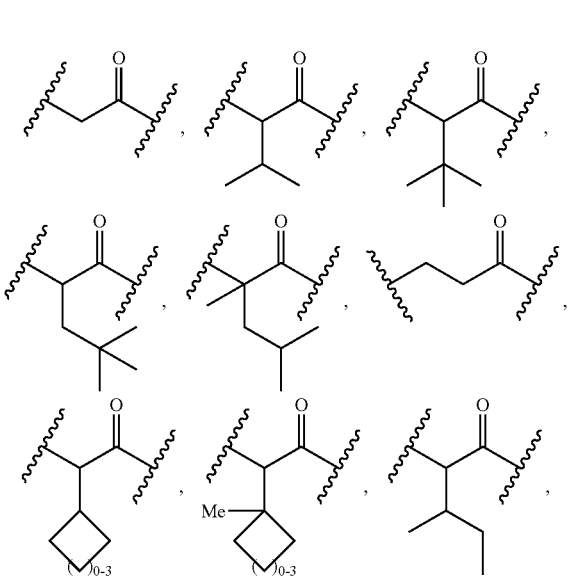
5. The compound of claim 1, wherein
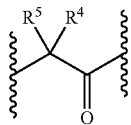
is selected from the group consisting of:

-continued

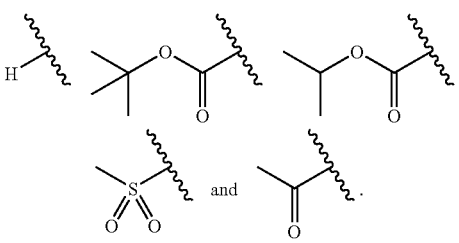

$Y^{32}$ is selected from the group consisting of:

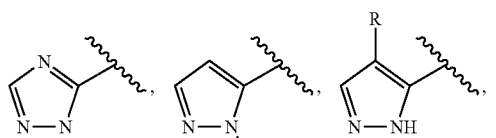

6. The compound of claim 1, wherein Z is NH.
7. The compound of claim 1, wherein Z is N(R).
8. The compound of claim 1, wherein Z is OG is C(=O).
9. The compound of claim 1, wherein G is present and is C(=O) or S(O$_2$).
10. The compound of claim 1, wherein Y is selected from the group consisting of:

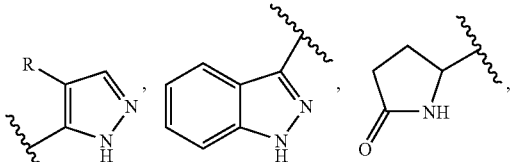

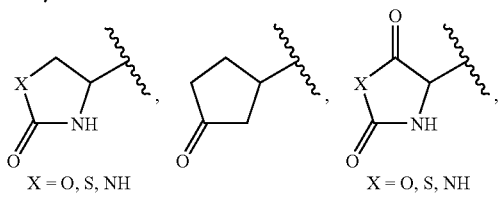

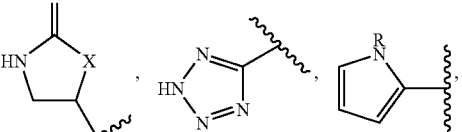

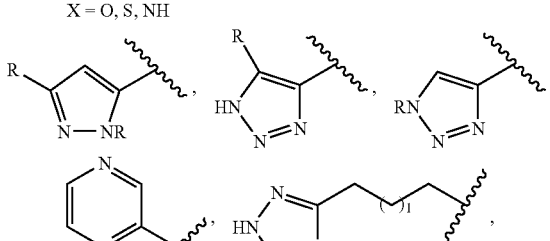

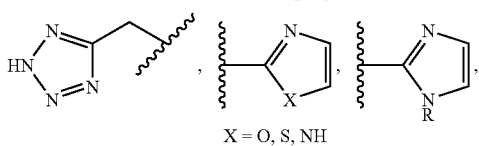

wherein
$Y^{31}$ is selected from the group consisting of: OR, NHR and NRR$^7$ and -continued

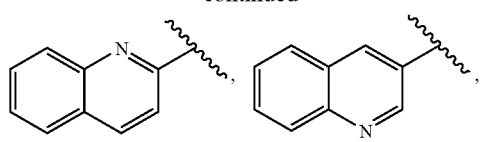

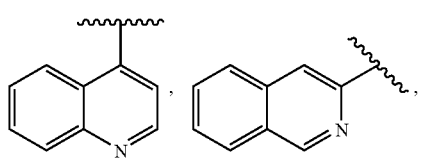

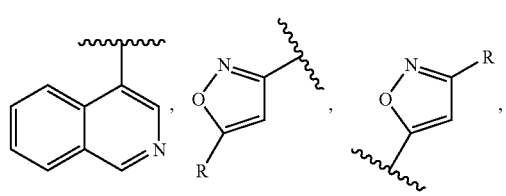

X = O, S, NH    X = O, S, NH

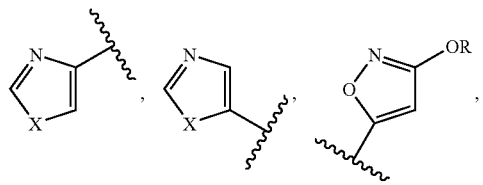

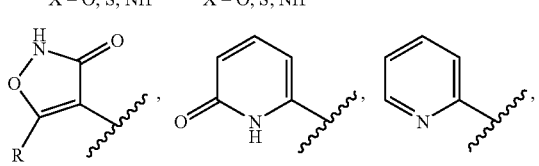

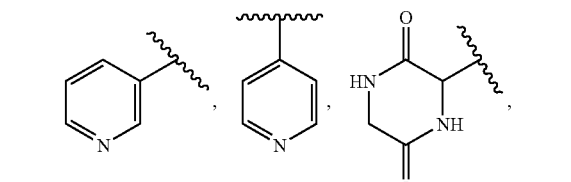

X = O, S, NH

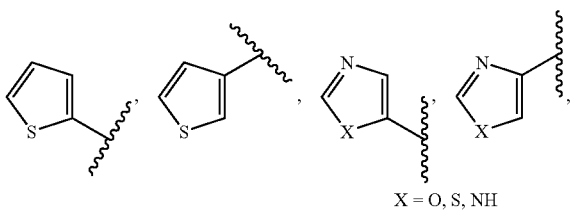

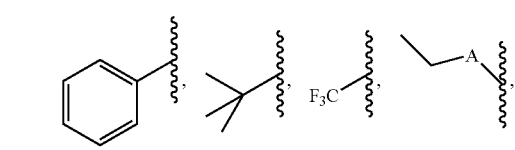

and

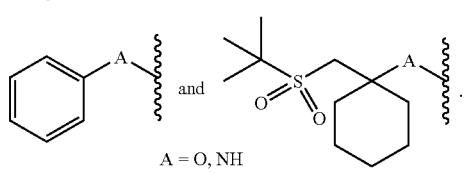

A = O, NH

11. The compound of claim 1, wherein:

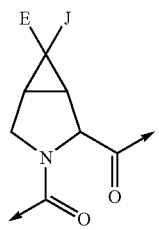

is selected from the group consisting of:

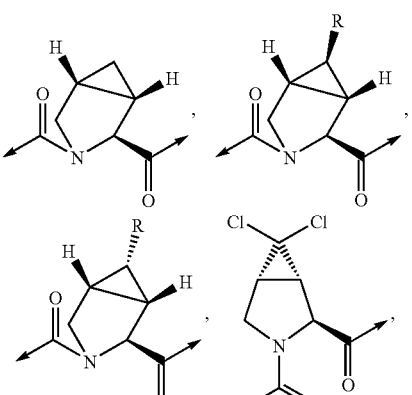

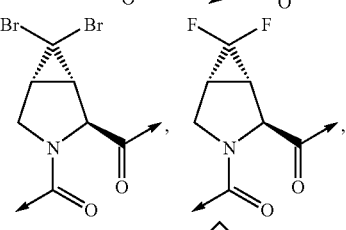

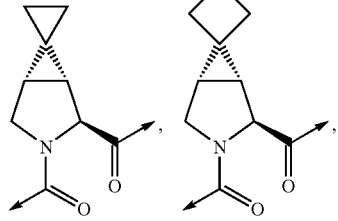

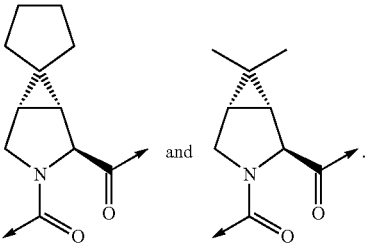

12. A pharmaceutical composition comprising as an active ingredient at least one compound of claim 1.

13. The pharmaceutical composition of claim 12 for use in treating disorders associated with HCV.

14. The pharmaceutical composition of claim 12 additionally comprising at least one pharmaceutically acceptable carrier.

15. The pharmaceutical composition of claim 14, additionally containing at least one antiviral agent.

16. The pharmaceutical composition of claim 15, still additionally containing at least one interferon.

17. The pharmaceutical composition of claim 16, wherein said at least one antiviral agent is ribavirin and said at least one interferon is α-interferon or pegylated interferon.

18. A method of treating disorders associated with the HCV, said method comprising administering to a patient in need of such treatment a pharmaceutical composition which comprises therapeutically effective amounts of at least one compound of claim 1.

19. The method of claim 18, wherein said administration is oral or subcutaneous.

20. A method of preparing a pharmaceutical composition for treating the disorders associated with the HCV, said method comprising bringing into intimate contact at least one compound of claim 1 and at least one pharmaceutically acceptable carrier.

21. A compound exhibiting HCV protease inhibitory activity, or enantiomers, stereoisomers, rotamers, tautomers, diastereomers, or racemates of said compound, or a pharmaceutically acceptable salt, solvate or ester of said compound, said compound being selected from the compounds of structures listed below:

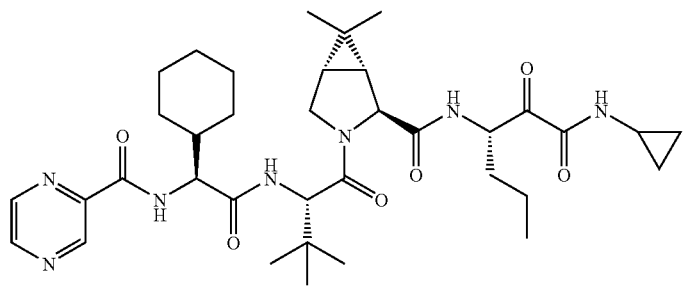

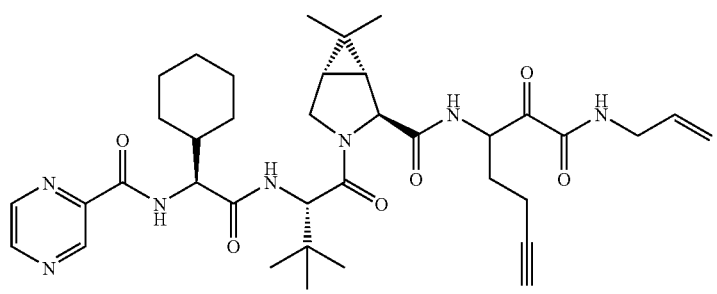

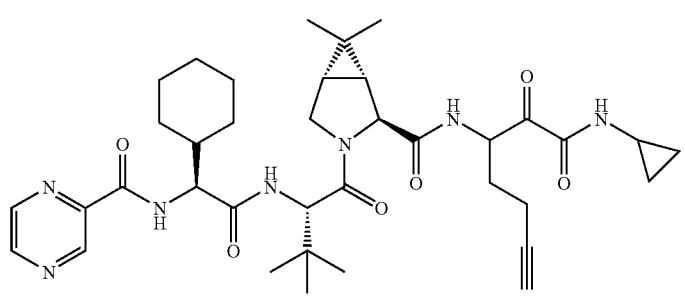

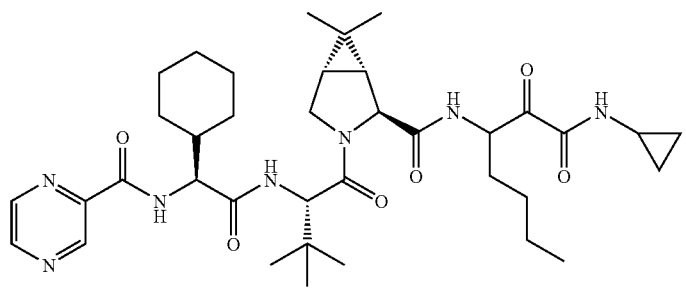

-continued
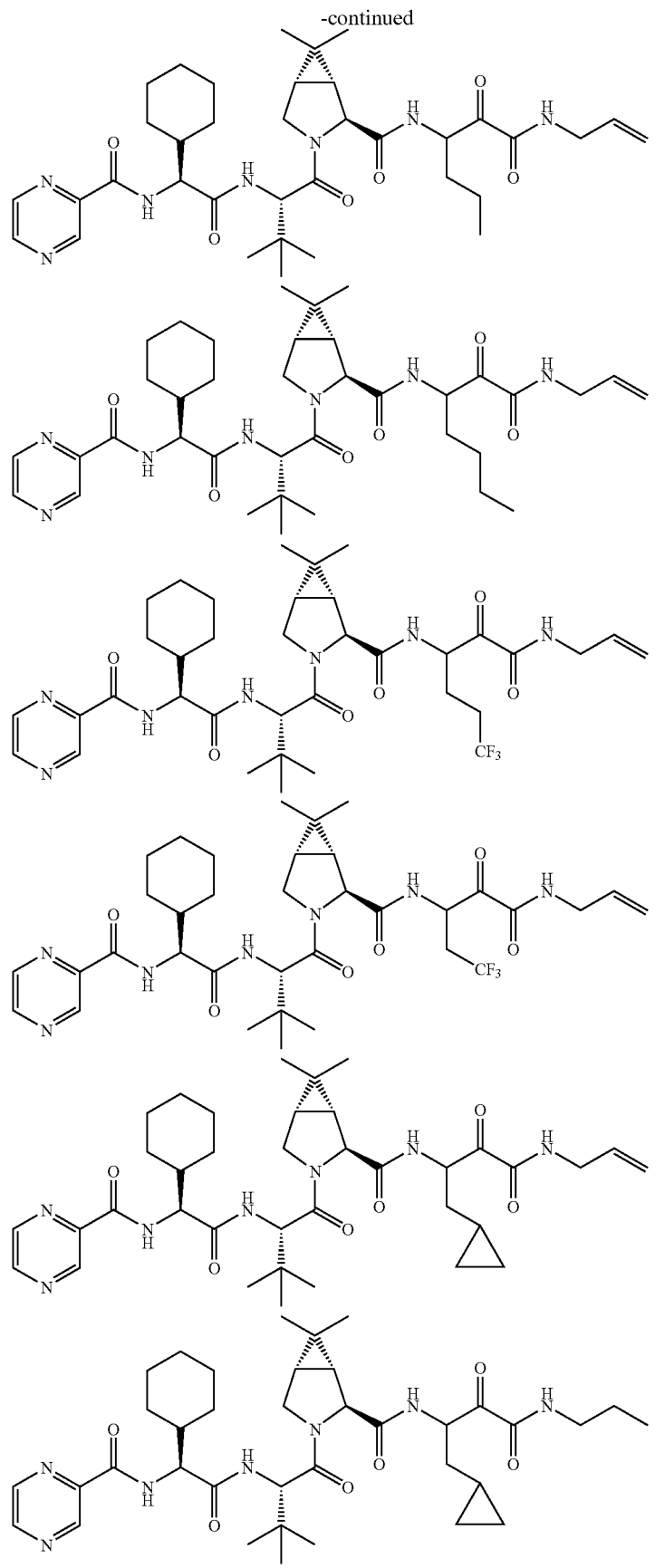

-continued
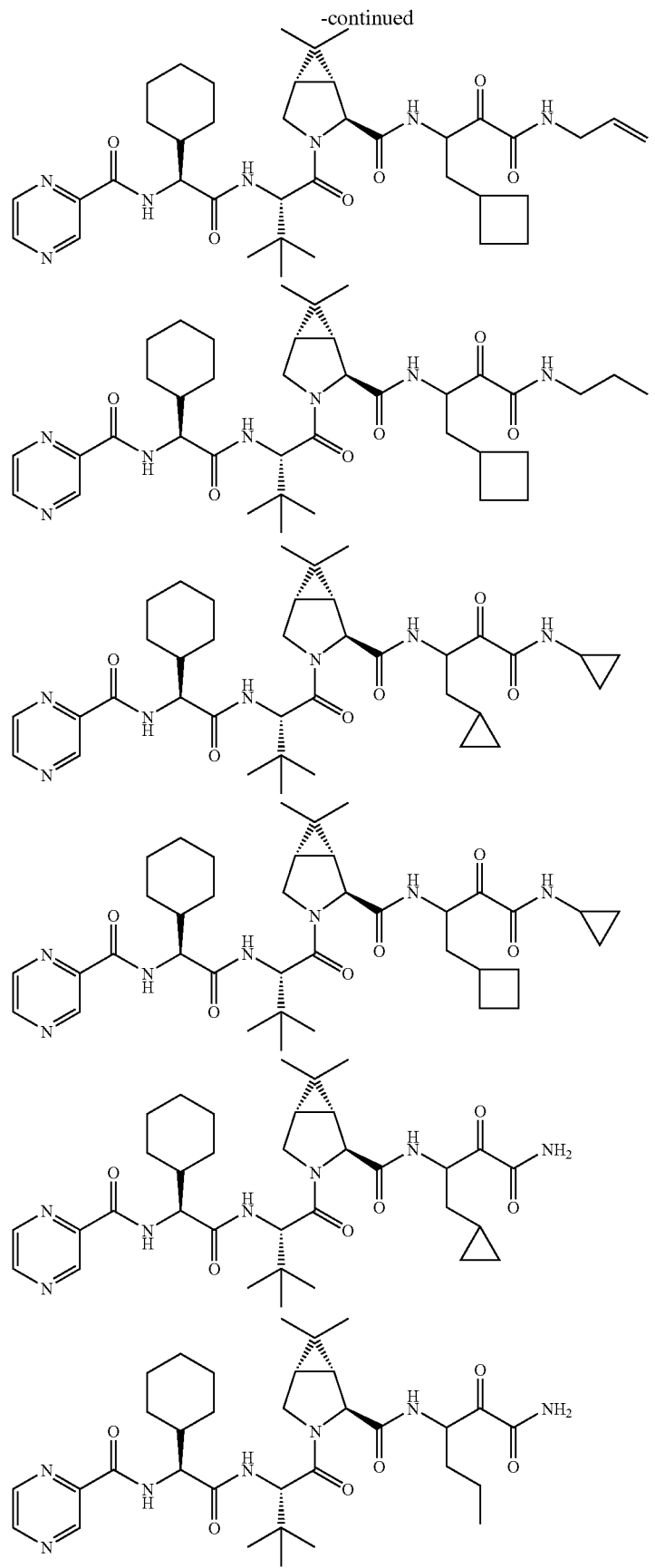

-continued
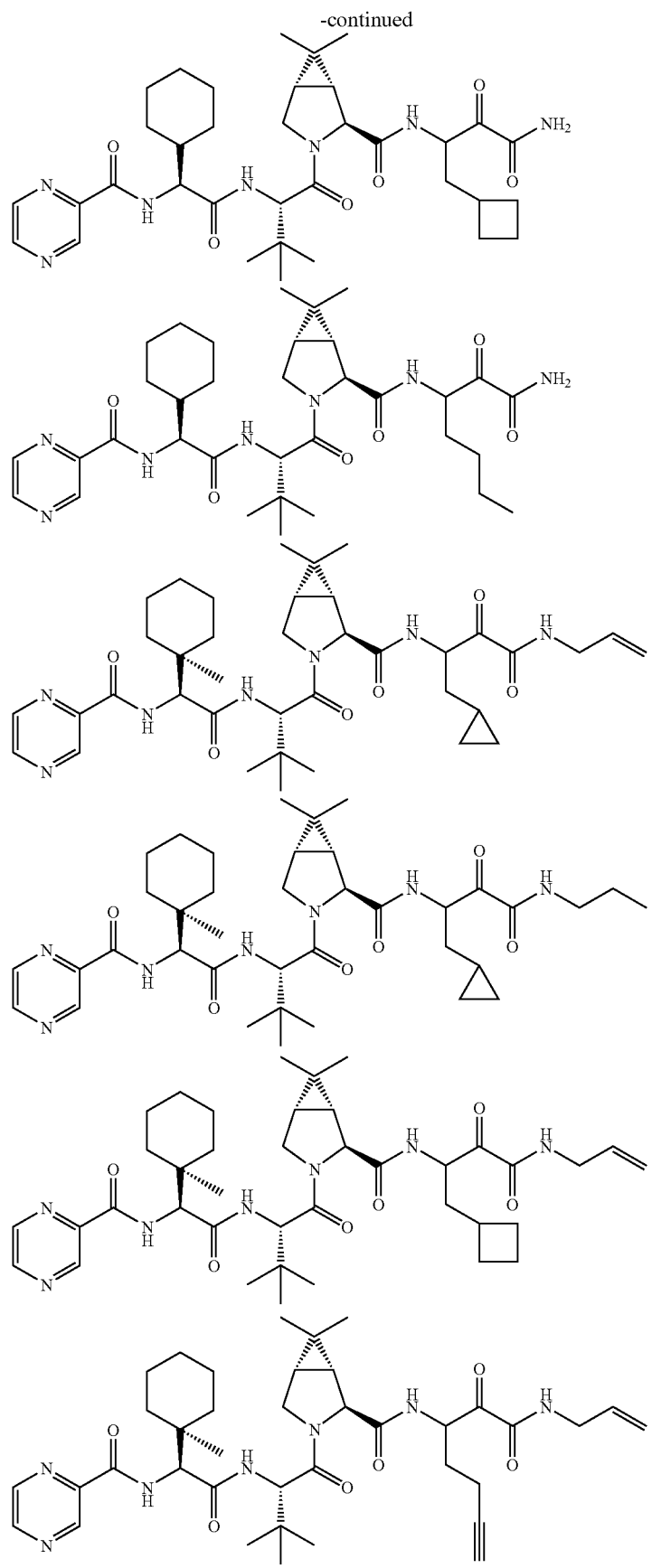

-continued
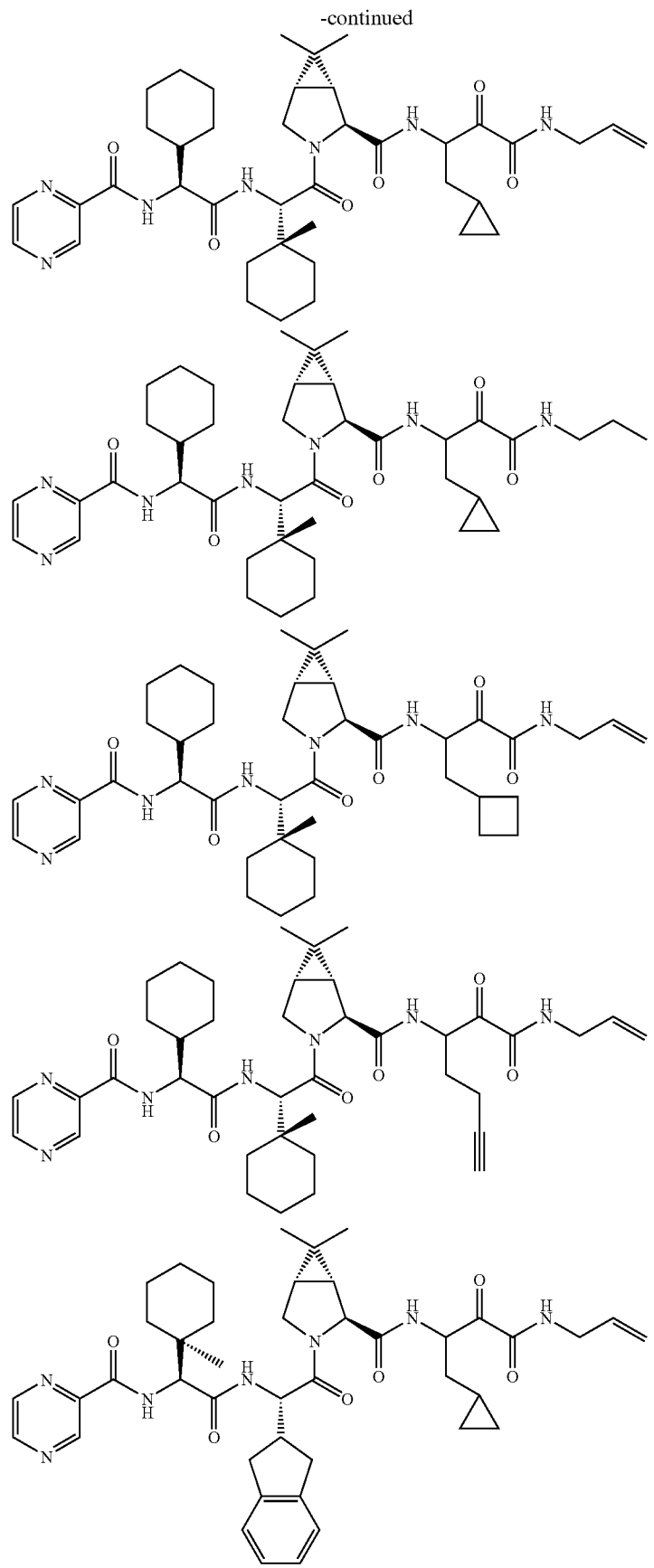

-continued
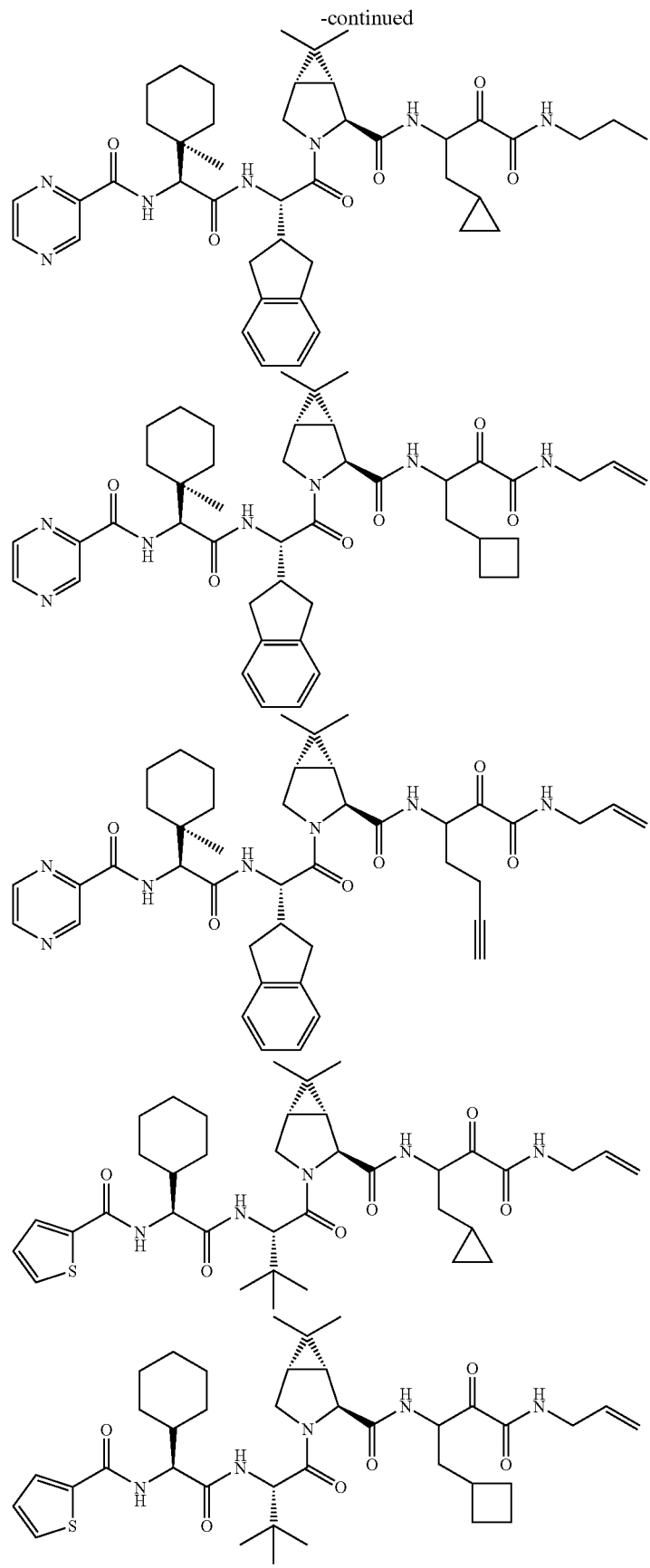

-continued
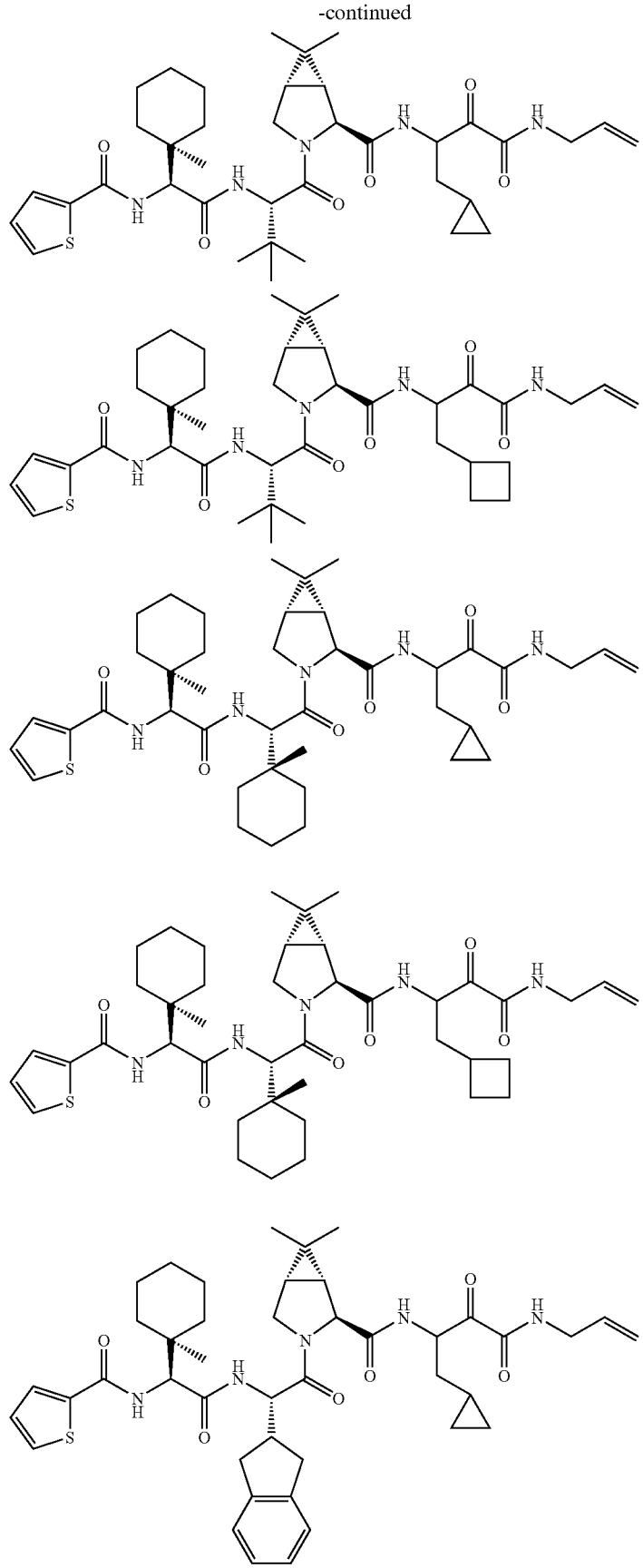

-continued
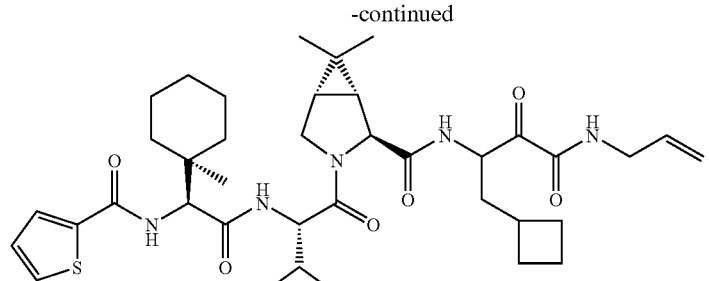
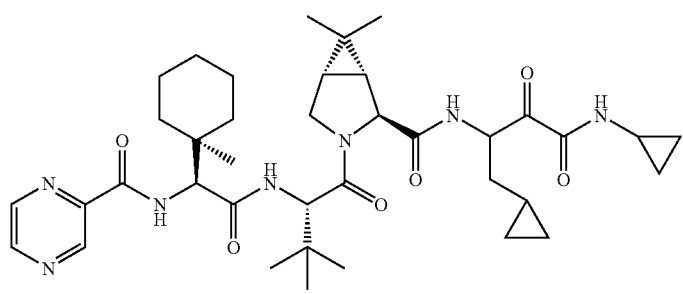
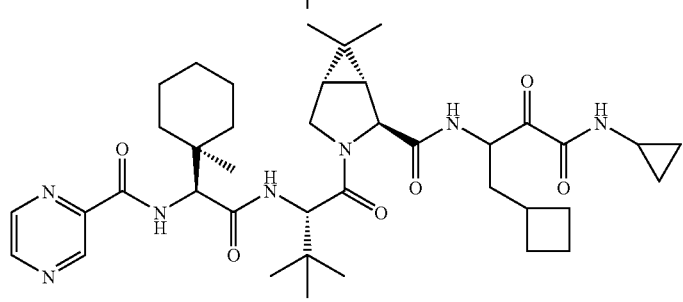
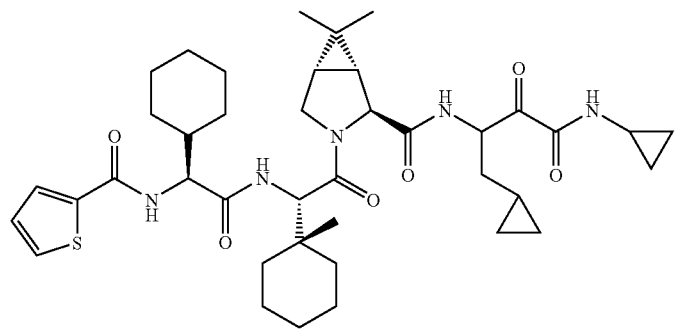
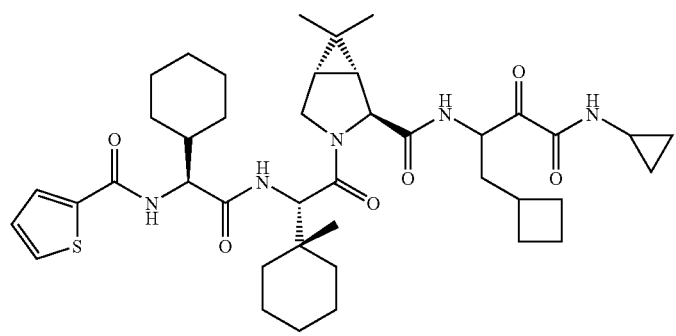

-continued
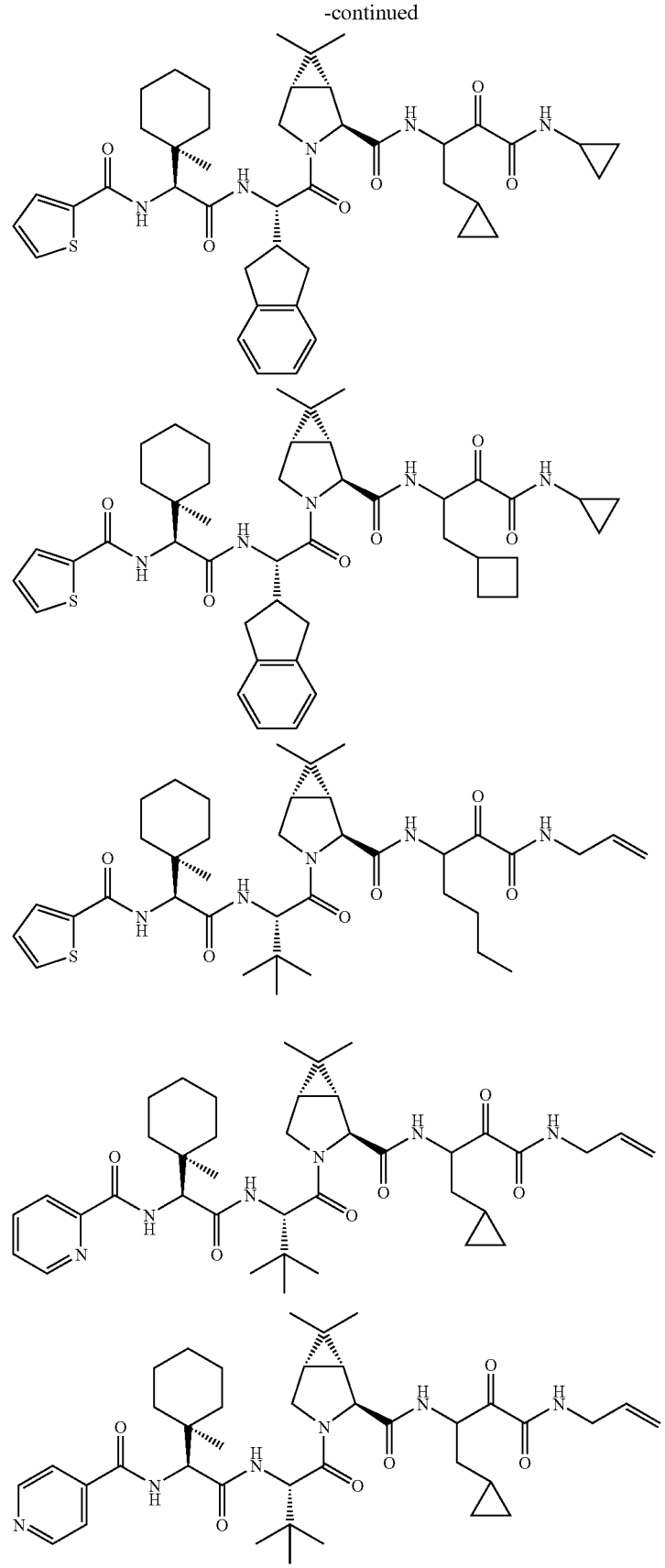

-continued
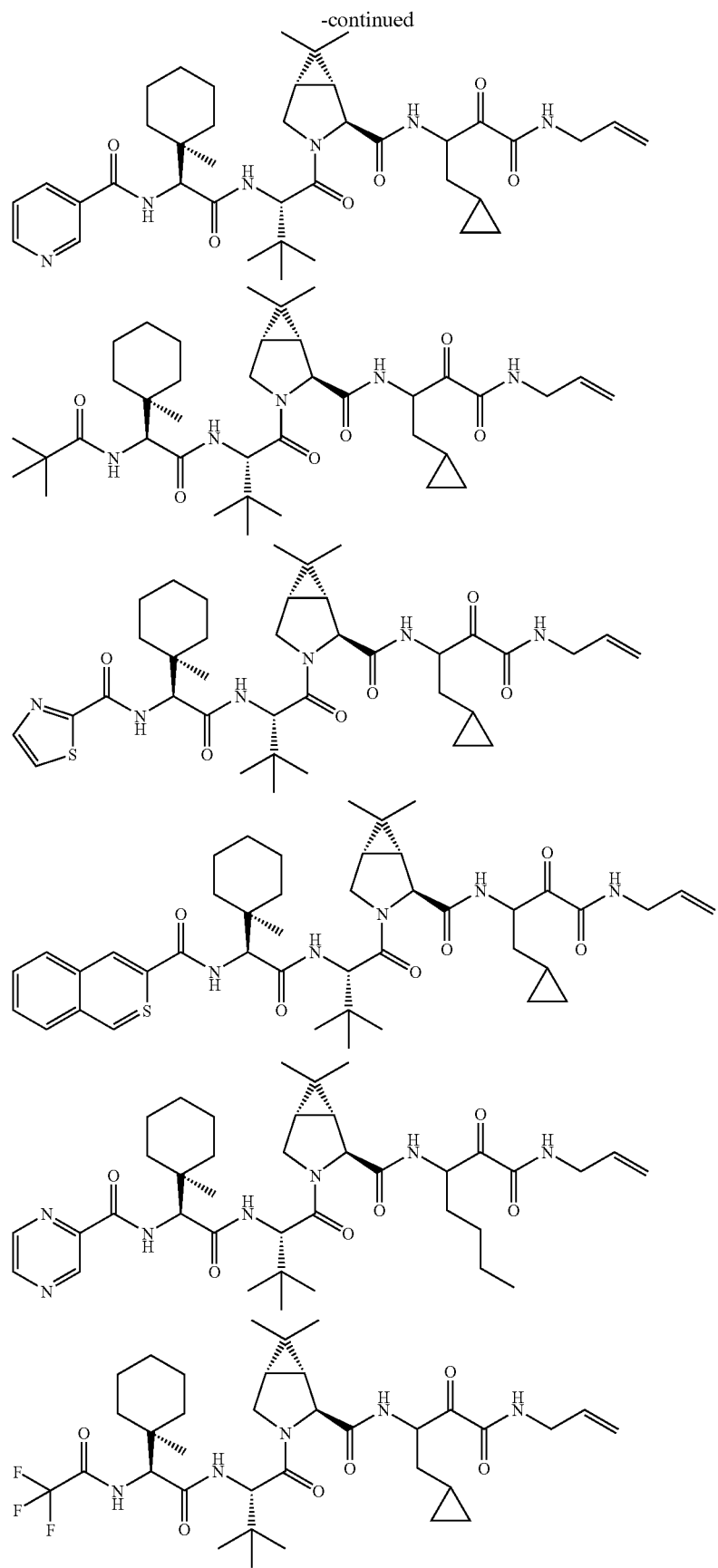

-continued
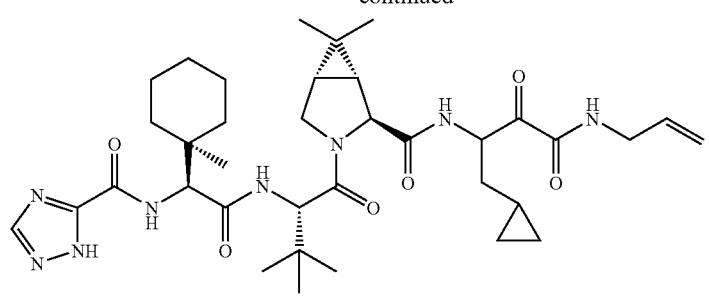
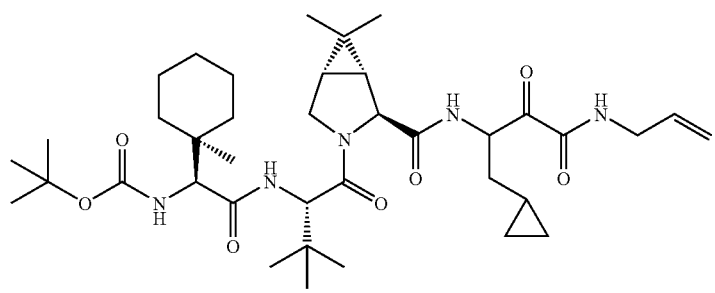
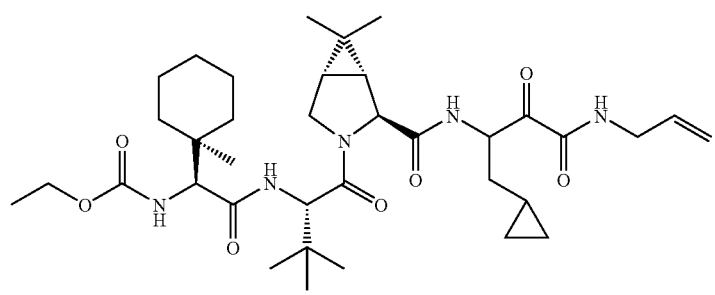
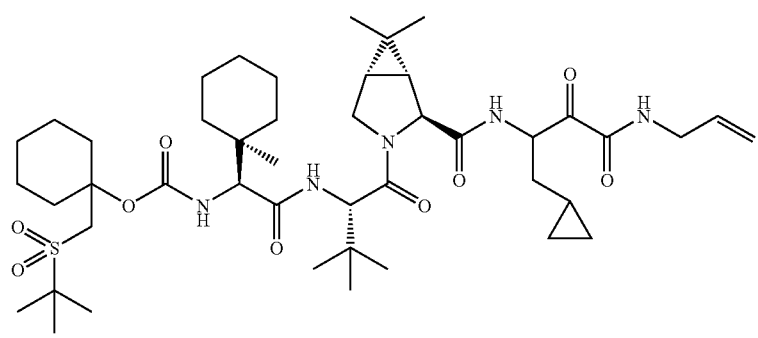
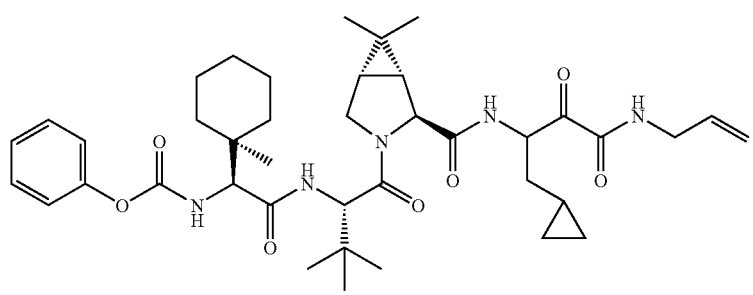

-continued
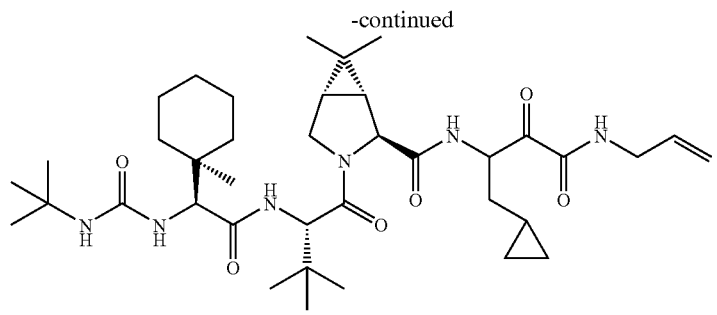
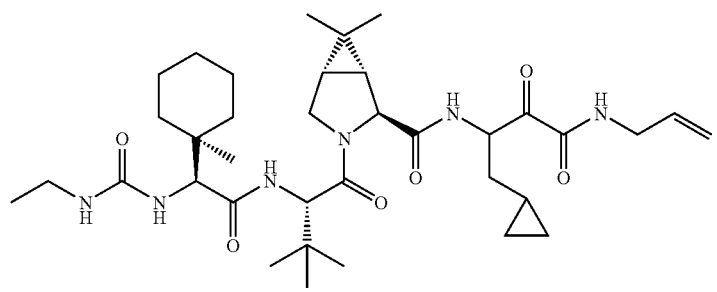
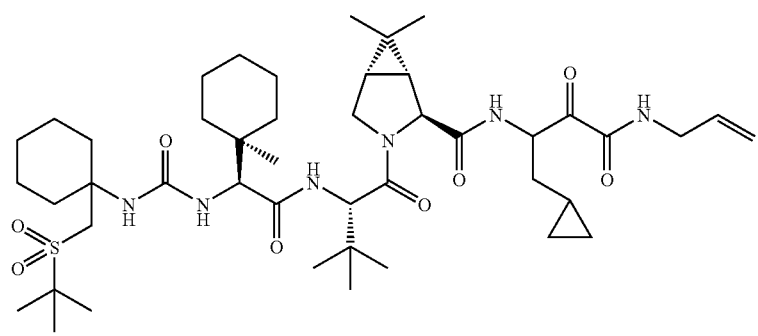
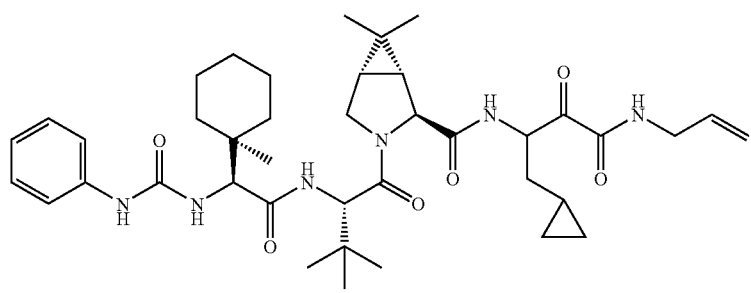
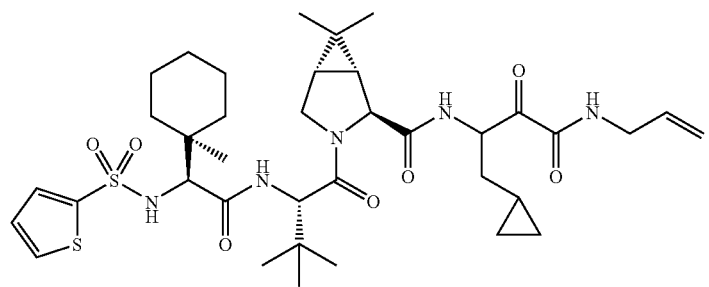

-continued
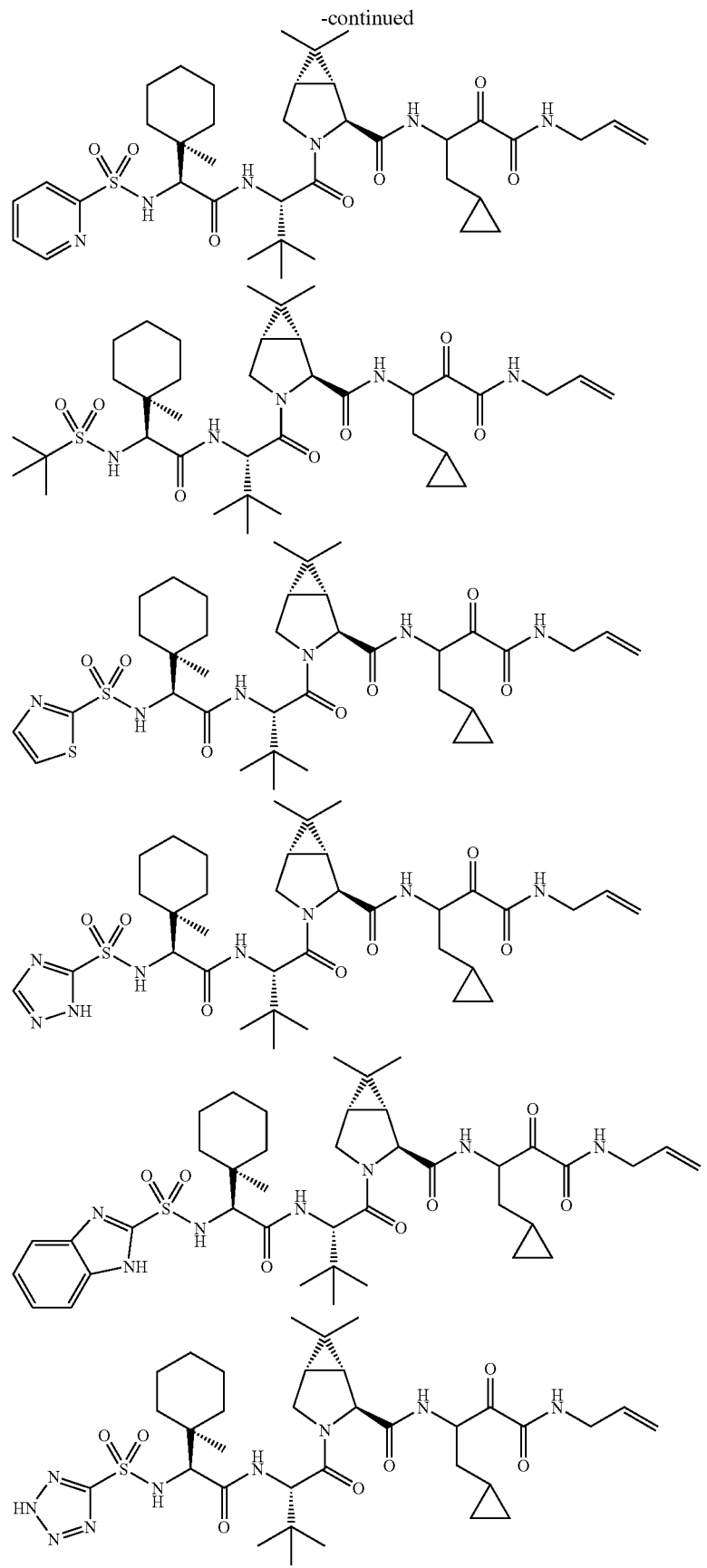

-continued
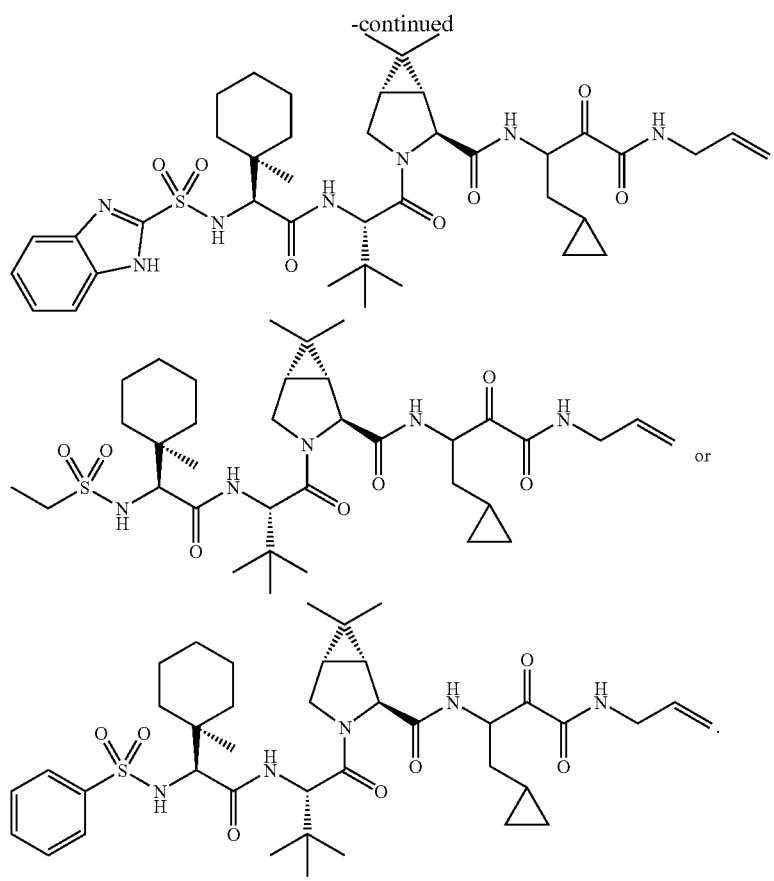
22. A compound, or enantiomers, stereoisomers, rotamers, tautomers, diastereomers, or racemates of said compound, or a pharmaceutically acceptable salt, solvate or ester of said compound, said compound being selected from the compounds of structures listed below:
-continued
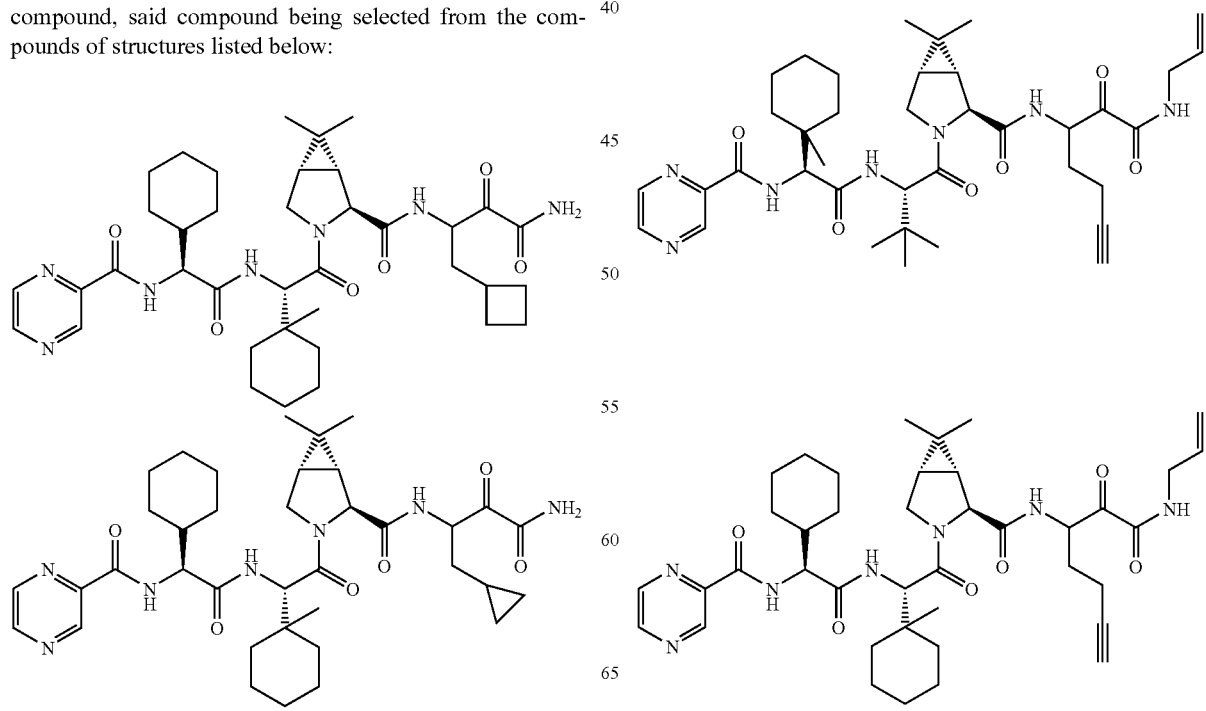

201
-continued
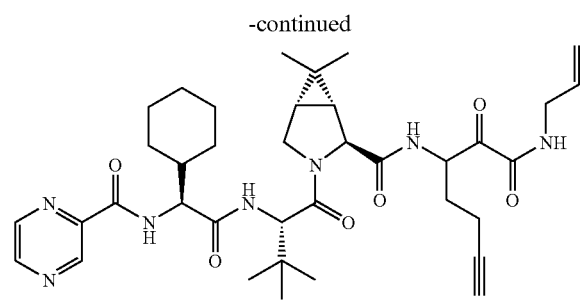
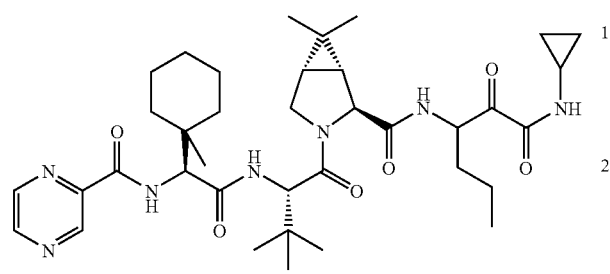
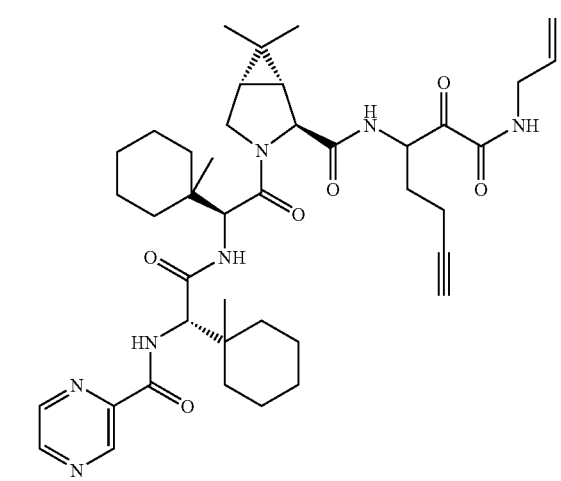
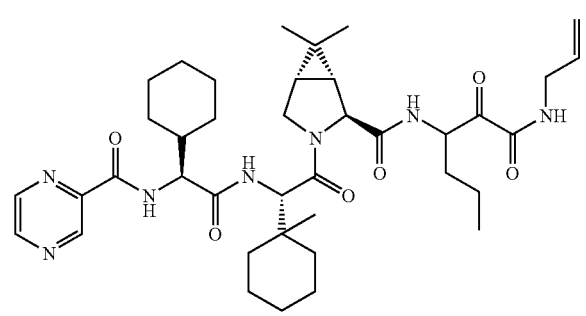
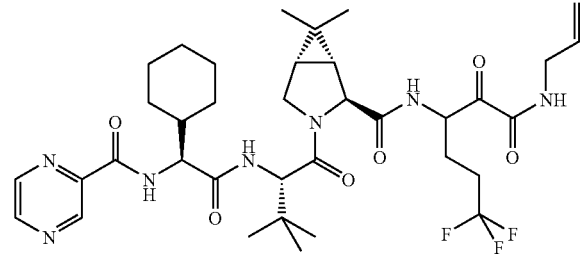
202
-continued
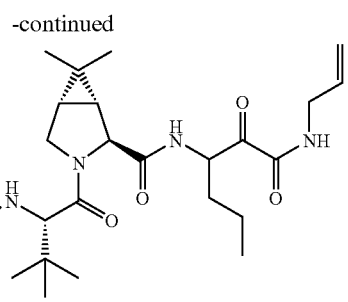
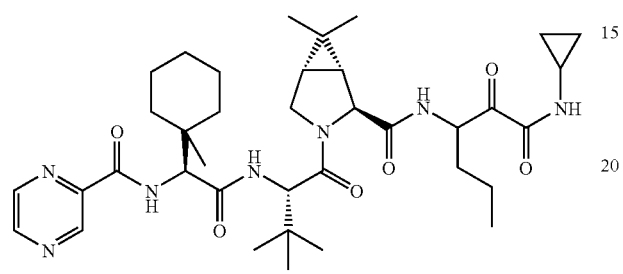
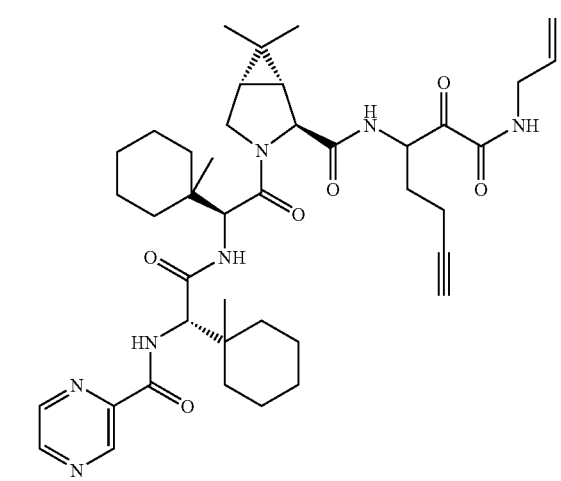
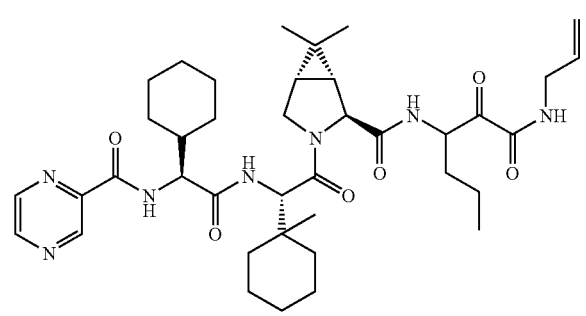
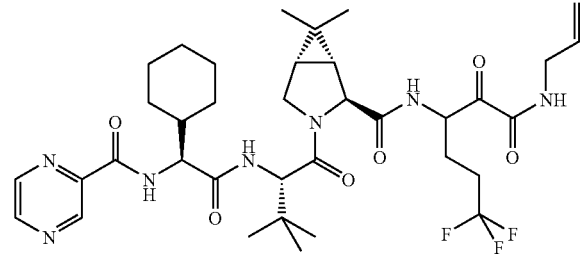

203
-continued
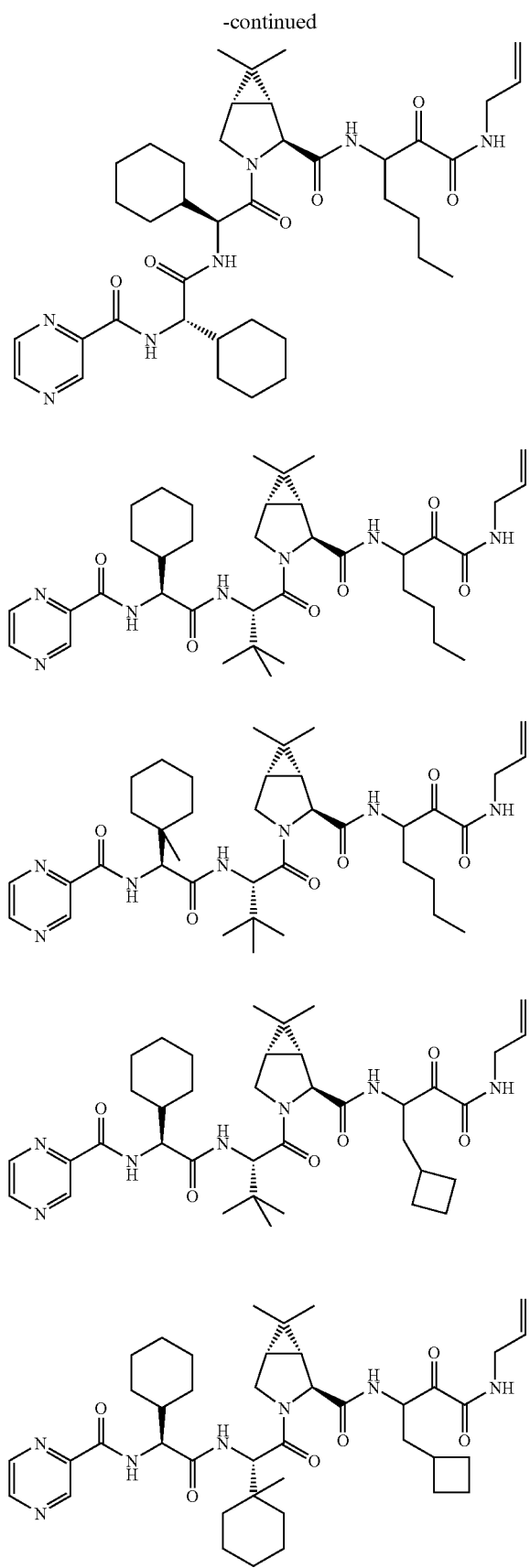
204
-continued
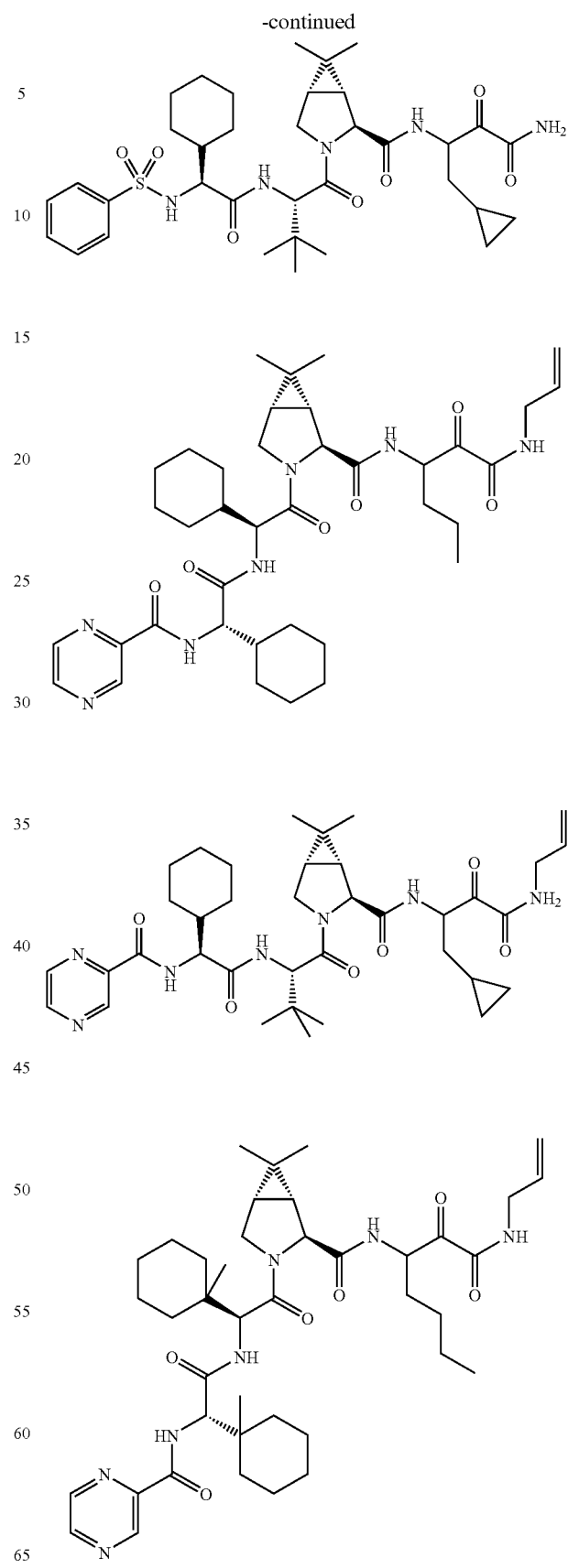

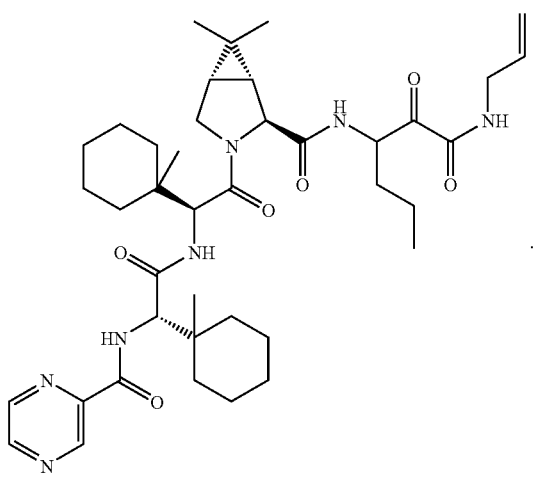

23. A pharmaceutical composition for treating disorders associated with the HCV, said composition comprising therapeutically effective amount of one or more compounds in claim 22 and a pharmaceutically acceptable carrier.

24. The pharmaceutical composition of claim 23, additionally containing at least one antiviral agent.

25. The pharmaceutical composition of claim 24, still additionally containing at least one interferon or PEG-interferon alpha conjugate.

26. The pharmaceutical composition of claim 25, wherein said at least one antiviral agent is ribavirin and said at least one interferon is α-interferon or pegylated interferon.

27. A method of treatment of a hepatitis C virus associated disorder, comprising administering an effective amount of one or more compounds of claim 22.

28. A method of modulating the activity of hepatitis C virus (HCV) protease, comprising contacting HCV protease with one or more compounds of claim 22.

29. A method of treating or ameliorating one or more symptoms of hepatitis C (HCV), comprising administering a therapeutically effective amount of one or more compounds of claim 22.

30. The method of claim 29, wherein the HCV protease is the NS3/NS4a protease.

31. The method of claim 29, wherein the compound or compounds inhibit HCV NS3/NS4a protease.

32. A method of modulating the processing of hepatitis C virus (HCV) polypeptide, comprising contacting a composition containing the HCV polypeptide under conditions in which said polypeptide is processed with one or more compounds of claim 22.

33. A compound of claim 1 in purified form.

34. A compound, or enantiomers, stereoisomers, rotamers, tautomers, diastereomers, or racemates of said compound, or a pharmaceutically acceptable salt, solvate or ester of said compound, said compound having the general structure shown in Formula I:

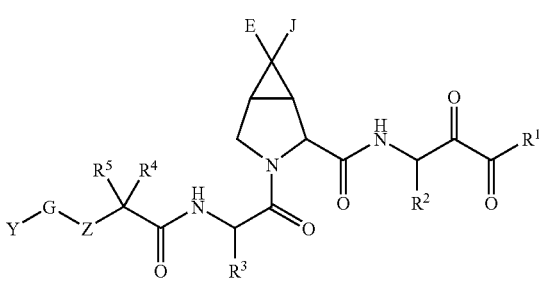

wherein:

R$^1$ is NR$^9$R$^{10}$, and R$^9$ is H, R$^{10}$ is H or R$^{14}$, wherein R$^{14}$ is alkyl, aryl, heteroalkyl, heteroaryl, cycloalkyl, alkyl-aryl-, alkyl-heteroaryl-, aryl-alkyl-, alkenyl, alkynyl or heteroaryl-alkyl-;

E and J can be the same or different, each being independently selected from the group consisting of R, OR, NHR, NRR$^7$, SR halo, and S(O$_2$)R, or E and J can be directly connected to each other to form either a three to eight-membered cycloalkyl, or a three to eight-membered heterocyclyl moiety;

Z is N(H), N(R), or O, G is C(=O) or S(O$_2$) with the proviso that when Z is O, G is not S(O$_2$) and;

Y is selected from the group consisting of

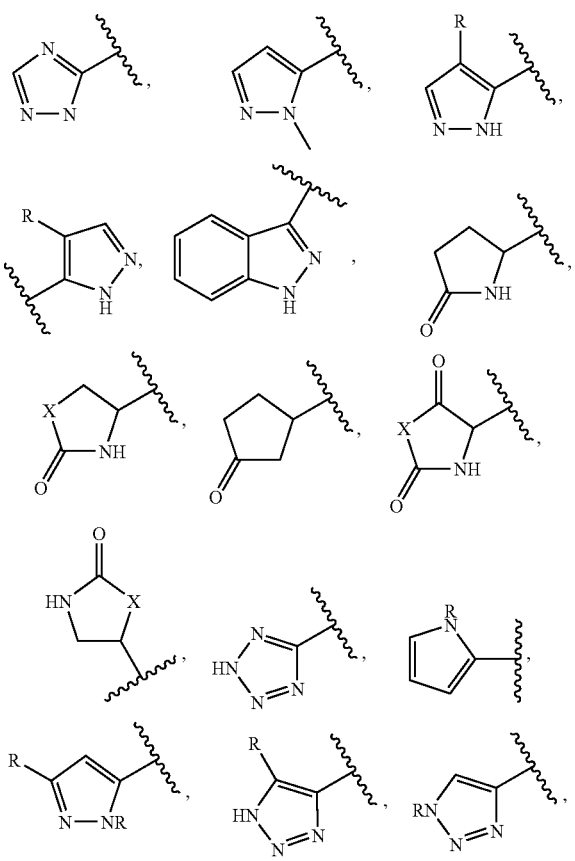

-continued

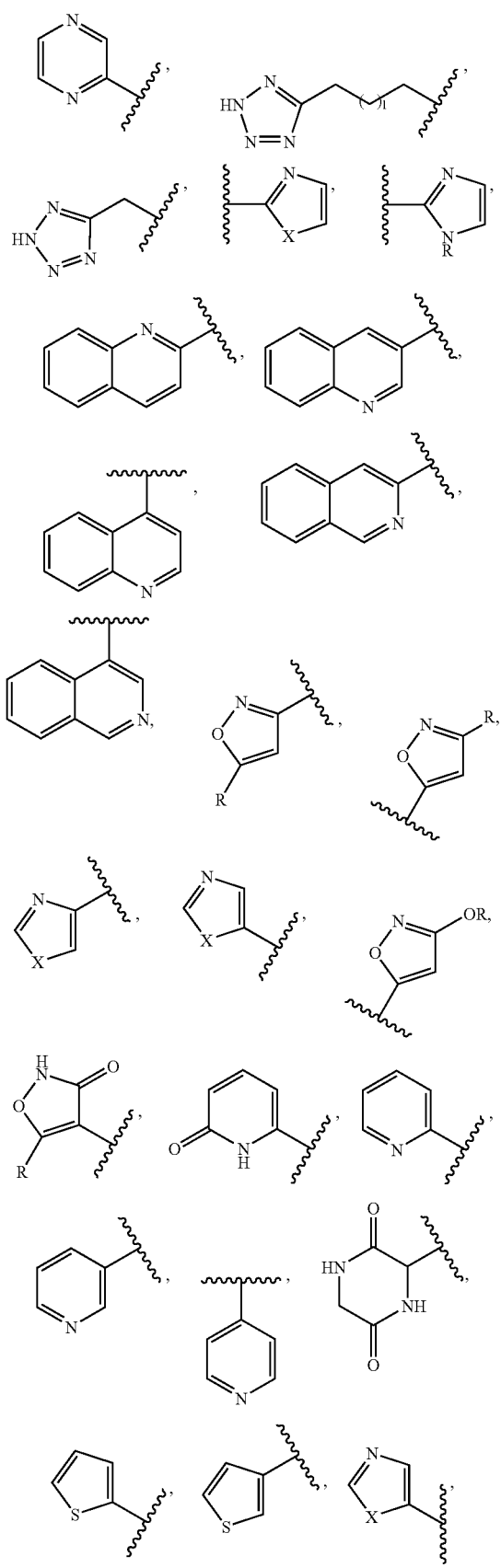

-continued

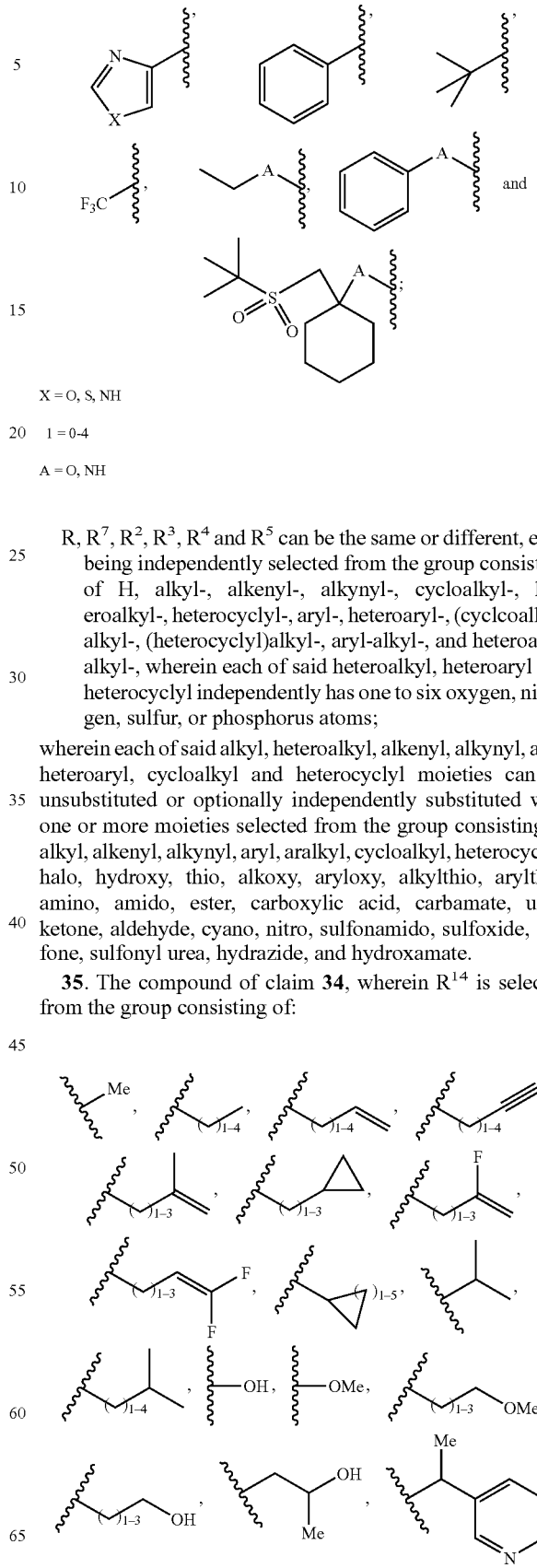

X = O, S, NH l = 0-4

A = O, NH

R, $R^7$, $R^2$, $R^3$, $R^4$ and $R^5$ can be the same or different, each being independently selected from the group consisting of H, alkyl-, alkenyl-, alkynyl-, cycloalkyl-, heteroalkyl-, heterocyclyl-, aryl-, heteroaryl-, (cyclcoalkyl)alkyl-, (heterocyclyl)alkyl-, aryl-alkyl-, and heteroaryl-alkyl-, wherein each of said heteroalkyl, heteroaryl and heterocyclyl independently has one to six oxygen, nitrogen, sulfur, or phosphorus atoms;

wherein each of said alkyl, heteroalkyl, alkenyl, alkynyl, aryl, heteroaryl, cycloalkyl and heterocyclyl moieties can be unsubstituted or optionally independently substituted with one or more moieties selected from the group consisting of alkyl, alkenyl, alkynyl, aryl, aralkyl, cycloalkyl, heterocyclyl, halo, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate.

35. The compound of claim 34, wherein $R^{14}$ is selected from the group consisting of:

-continued
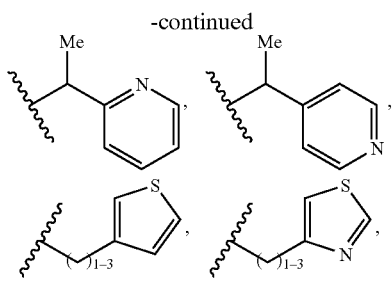
-continued
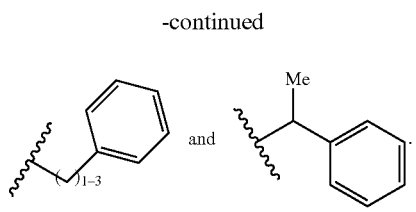
* * * * *